United States Patent
Kishino et al.

(10) Patent No.: US 7,504,412 B2
(45) Date of Patent: Mar. 17, 2009

(54) IMIDAZOPYRIDINE DERIVATIVES

(75) Inventors: Hiroyuki Kishino, Tsukuba-Gun (JP);
Minoru Moriya, Tsukuba (JP);
Toshihiro Sakamoto, Moriya (JP);
Hidekazu Takahashi, Tsukuba (JP);
Shunji Sakuraba, Tsukuba (JP); Takao Suzuki, Tsukuba (JP); Akio Kanatani, Ushiku (JP)

(73) Assignee: Banyu Pharmaceuticals, Co., Ltd., Tokyo (JP)

( * ) Notice: Subject to any disclaimer, the term of this patent is extended or adjusted under 35 U.S.C. 154(b) by 482 days.

(21) Appl. No.: 10/567,269

(22) PCT Filed: Aug. 13, 2004

(86) PCT No.: PCT/JP2004/011945

§ 371 (c)(1),
(2), (4) Date: Feb. 6, 2006

(87) PCT Pub. No.: WO2005/016928

PCT Pub. Date: Feb. 24, 2005

(65) Prior Publication Data

US 2008/0200494 A1    Aug. 21, 2008

(30) Foreign Application Priority Data

Aug. 15, 2003    (JP) .............................. 2003-207632

(51) Int. Cl.
*A61K 31/44*    (2006.01)
*C07D 471/02*    (2006.01)
*C07D 491/02*    (2006.01)
*C07D 498/02*    (2006.01)
*C07D 513/02*    (2006.01)
*C07D 515/02*    (2006.01)

(52) U.S. Cl. ..................................... 514/300; 546/121

(58) Field of Classification Search ................. 546/121; 514/300
See application file for complete search history.

(56) References Cited

U.S. PATENT DOCUMENTS

| 3,701,780 | A | * | 10/1972 | Fisher | ...................... 546/121 |
| 7,109,351 | B1 | * | 9/2006 | Albaugh et al. | ............. 548/492 |
| 2003/0212070 | A1 | | 11/2003 | Schwink et al. | |
| 2004/0077628 | A1 | | 4/2004 | Ishihara et al. | |
| 2005/0261303 | A1 | | 11/2005 | Taniguchi et al. | |

FOREIGN PATENT DOCUMENTS

| JP | 2001-226269 | | 8/2001 |
| JP | 2003-313126 | | 11/2003 |
| WO | 0116103 | * | 3/2001 |
| WO | WO 01/21577 | | 3/2001 |
| WO | WO 02/42273 | | 5/2002 |
| WO | WO 02/094799 | | 11/2002 |
| WO | WO03015769 A1 | | 2/2003 |
| WO | 2004007471 | * | 1/2004 |
| WO | WO 2004/007471 | | 1/2004 |
| WO | WO 2005/019240 | | 3/2005 |
| WO | WO 2005/035526 | | 4/2005 |
| WO | WO 2005/040157 | | 5/2005 |

OTHER PUBLICATIONS

Lembo et al., Nature Cell Biology (1999), 1(5), 267-271.*
Takahashi et al., Yakugaku Zasshi (1949), 69, 496-7.*
Fisher et al., Journal of Medicinal Chemistry (1972), 15(9), 982-5.*
Sundberg et al., Chemical Research in Toxicology (1993), 6(4), 506-10.*

* cited by examiner

*Primary Examiner*—D. Margaret Seaman
*Assistant Examiner*—Niloofar Rahmani
(74) *Attorney, Agent, or Firm*—Janet E. Fair; Catherine D. Fitch

(57) ABSTRACT

The invention provides imidazopyridine derivatives represented by the general formula [I] [in which $R^1$ and $R^2$ may be the same or different and stand for $C_{1-6}$ alkyl or the like, $R^3$ and $R^4$ stand for hydrogen atom, methyl group or the like, W stands for mono- or bi-cyclic 3- to 8-membered aromatic or aliphatic heterocycle or the like, and Ar stands for optionally substituted aromatic heterocycle or the like]. These compounds act as melanin-concentrating hormone receptor antagonist and are useful as medicines for central nervous system disorders, cardiovascular system disorders and metabolic disorders.

18 Claims, 1 Drawing Sheet

IMIDAZOPYRIDINE DERIVATIVES

CROSS-REFERENCE TO RELATED APPLICATIONS

This application is a U.S. National Phase application under 35 U.S.C. §371 of PCT Application No. PCT/JP2004/011945, filed Aug. 13, 2004, which claims priority under 35 U.S.C. §365(b) from Japanese patent application No. JP2003-207632, filed Aug. 15, 2003.

TECHNICAL FIELD

This invention relates to imidazopyridine derivatives which are useful in the field of medicines. Said compounds act as antagonists to melanin concentrating hormone receptor, and are useful as preventing or treating agents of various diseases of cardiovascular system, nervous system, metabolic systems, reproductive system, respiratory system, digestive system and the like.

BACKGROUND ART

Melanin concentrating hormone (hereafter abbreviated as "MCH") is a cyclic peptide hormone/neuro-peptide, which was for the first time isolated by Kawauchi, et al. in 1983 from sermon hypophysis [Nature, Vol. 305, 321 (1983)]. The hormone is known to functionally antagonize to melanin cell stimulating hormone in fishes, to cause concentration of melanin granules in melanophore and participate in body color change [International Review of Cytology, Vol. 126, 1(1991); Trends in Endocrinology and Metabolism, Vol. 5, 120 (1994)]. Also in mammals, MCH-containing neuron nerve cells are localized in the hypothalamus lateral field and uncertain zone, but their nerve fibers are projecting over a very wide scope in the brain [The Journal of Comparative Neurology, Vol. 319, 218 (1992)], and MCH is considered to preside over various central functions in living bodies.

Hypothalamus lateral field is known of old as feeding center, and furthermore, recently molecular biological and pharmacological knowledges suggesting participation of MCH in controlling energetic homeostasis are being accumulated. That is, it has been reported that expression of mRNA, which is a MCH precursor, was accelerated in brains of ob/ob mouse, db/db mouse, $A^y$/a mouse, Zucker fatty rat or the like which are model animals of hereditary obesity, or in brains of fasted mice [Nature, Vol. 380, 243 (1996); Diabetes, Vol. 47, 294 (1998); Biochemical and Biophysical Research Communications, Vol. 268, 88 (2000); Molecular Brain Research, Vol. 92, 43 (2001)].

Acute ventricular administration of MCH to rats was observed to induce accelerated feeding activity [Nature, Vol. 380, 243 (1996)] and chronic administration invites obesity accompanied by polyphagy [Proceedings of the National Academy of Science of the United States of America, Vol. 99, 3240, (2002)]. Moreover, MCH precursor gene-deficient mouse shows reduced food ingestion or rise in oxygen consumption per body weight compared to wild type mice. Its low body weight due to decrease in body fat was observed [Nature, Vol. 396, 670 (1998)].

On the contrary, transgenic mouse which expresses excessive MCH precursor develops obesity accompanied by polyphagy and insulin resistance [The Journal of Clinical Investigation, Vol. 107, 379 (2001)]. Consequently, it is suggested that MCH is an important factor for developing obesity and participates in diseases induced by metabolic disorder or respiratory diseases of which one of risk factors is obesity.

Besides, MCH is known to participate also in anxiety-causing action, epilepsy, memory, learning, diuretic action, excretory action of sodium and potassium, oxytocin secreting action, reproduction and reproductive function [Peptides, Vol. 17, 171 (1996); Peptides, Vol. 18, 1095 (1997), Peptides, Vol. 15, 757 (1994); Journal of Neuroendocrinology, Vol. 8, 57 (1996); Critical Reviews in Neurobiology, Vol. 8, 221, (1994)].

MCH causes versatile pharmacological actions through MCH receptors which are present mainly in the central nervous system. As receptors of MCH, at least two types of type 1 receptors (MCH-1R or SLC-1) and type 2 receptors (MCH-2R or SLT) are known [Nature, Vol. 400, 261 (1999); Nature, Vol. 400, 265 (1999); Biochemical and Biophysical Research Communications, Vol. 261, 622 (1999); Nature Cell Biology, Vol. 1, 267 (1999); FEBS Letters, Vol. 457, 522 (1999); Biochemical and Physical Research Communications, Vol. 283, 1013 (2001); The Journal of Biological Chemistry, Vol. 276, 20125 (2001); Proceedings of the National Academy of Sciences of the United States of America, Vol. 98, 7564 (2001); Proceedings of the National Academy of Sciences of the United States of America, Vol. 98, 7576 (2001); The Journal of Biological Chemistry, Vol. 276, 34664 (2001); and Molecular Pharmacology, Vol. 60, 632 (2001)].

Of those, the pharmacological action observed on rodents is induced mainly via MCH-1R [Genomics, Vol. 79, 785 (2002)]. Because MCH-1R gene-deficient mice chronically administered with MCH do not develop polyphagy or obesity, it is known that controlling of energy exchange by MCH is induced via MCH-1R. Furthermore, deficiency of MCH-1R promotes activity amount of mouse [Proceedings of the National Academy of Sciences of the United States of America, Vol. 99, 3240 (2002)], and its participation in central diseases accompanied by behavioral disorder, for example, attention-deficit hyperactivity disorder, schizophrenia and the like also is strongly suggested [Molecular Medicine Today, Vol. 6, 43 (2000); Trends in Neuroscience, Vol. 24, 527 (2001)].

It is also reported that autoantibody to MCH-1R is present in serum of vitiligo vulgaris patient [The Journal of Clinical Investigation, Vol. 109, 923 (2002)]. Furthermore, expression of MCH-1R in certain species of cancer cells was reported, and in vivo expression sites of MCH and MCH-1R also suggest their participation in cancer, sleep, vigil, drug dependence and digestive disorders [Biochemical and Biophysical Research Communications, Vol. 289, 44 (2001); Neuroendocrinology, Vol. 61, 348 (1995); Endocrinology, Vol. 137, 561 (1996); The Journal of Comparative Neurology, Vol. 435, 26 (2001)].

Functions of MCH are expressed upon its binding to MCH receptors. Therefore, when its binding to MCH receptor is inhibited, expression of MCH action can be inhibited. In consequence, substances which are antagonists to binding of MCH to its receptor are useful as preventing or treating agent of those various diseases in which MCH participates, for example, metabolic disorders represented by obesity, diabetes, hormone disorder, hyperlipidemia, gout, fatty liver, hepatitis and cirrhosis; cardiovascular disorders, represented by stenocardia, acute or congestive heart failure, myocardial infarction, coronary atherosclerosis, hypertension, renal diseases and electrolyte abnormality; central nervous system or peripheral nervous system disorders represented by bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence and alcoholism;

reproductive disorders represented by infertility, preterm labor and sexual dysfunction; digestive disorders; respiratory disorders; cancer or pigmentation.

As compounds analogous to the compounds of the present invention, for example, JP Tokuhyo (public announcement) Hei 10(1998)-500960A shows the following:

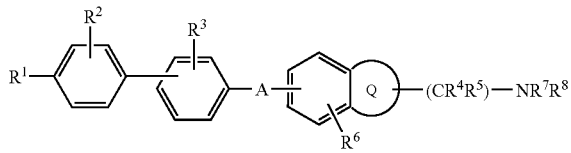

These compounds exhibit 5HT1D-antagonistic activity and include indole skeleton, indoline skeleton and the like but do not include imidazopyridine skeleton, and are different from the compounds of the present invention in mechanism of the action and utility.

On the other hand, as known antagonist to melanin concentrating hormone receptor, there are those described in, for example, International Publications WO 01/21577 Pamphlet and WO 01/82925 Pamphlet. In particular, WO 01/82925 shows the following compounds as melanin concentrating hormone receptor antagonist:

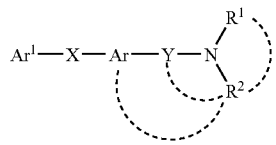

This reference does neither refer to imidazopyridine ring as Ar nor contain any specific disclosure on compounds having specific substituents at specific sites of imidazopyridine ring or on production process of such compounds. Hence no person skilled in the art who read WO 01/82925 Pamphlet could easily anticipate that the imidazopyridine derivatives of the present invention exhibit excellent action as melanin concentrating hormone receptor antagonist.

Patent literature 1: WO 01/21577
Patent literature 2: WO 01/82925

This invention aims at provision of piperidine derivatives having the action to inhibit binding of MCH to MCH-1R and also to provide preventing or treating agents for cardiovascular disorders, nervous disorders, metabolic disorders, reproductive disorders, respiratory disorders, digestive disorders and the like.

DISCLOSURE OF THE INVENTION

We have engaged in concentrative studies with the view to develop compounds which inhibit binding of MCH to MCH-1R, to discover that those compounds of imidazopyridine skeletal structure characterized by having specific substituents at 2-, 3- and 6-positions of the structure are novel substances not described in prior art literature and are effective as MCH-1R antagonist, and have completed the present invention based on that discovery.

Accordingly, therefore, the present invention relates to:

(1) imidazopyridine derivatives represented by a general formula [I]

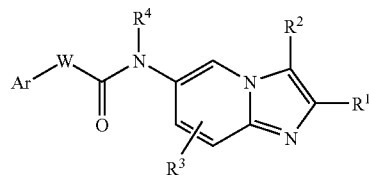

[in which
$R^1$ and $R^2$ stand for same or different substituents selected from the group consisting of
1) hydrogen
2) halogen
3) $C_{1-6}$ alkyl
4) $C_{3-8}$ cycloalkyl-$C_{0-4}$ alkyl
5) $C_{1-6}$ alkylamino
6) di-$C_{1-6}$ alkylamino
7) $C_{1-6}$ alkylcarbonylamino
8) $C_{1-6}$ alkylcarbonyl-($C_{1-6}$ alkyl)amino, and
9) 3 to 8-membered heterocycloalkyl-$C_{0-4}$ alkyl, wherein $C_{1-6}$ alkyl moiety may be substituted with $R^5$, cycloalkyl or heterocycloalkyl moiety may be substituted with $R^6$, and $R^1$ and $R^2$ are not hydrogen at the same time, or $R^1$ and $R^2$ may together form —$(CH_2)m$-, m standing for an integer of 3-6, wherein 1 or 2 hydrogen atoms constituting methylene may be substituted with $R^6$, $R^3$ stands for hydrogen, halogen, $C_{1-6}$ alkyl or $C_{1-6}$ alkyloxy, $R^4$ stands for hydrogen or $C_{1-6}$ alkyl, $R^5$ stands for a substituent selected from the group consisting of halogen, cyano, hydroxyl, amino, optionally fluorine- or hydroxyl-substituted $C_{1-6}$ alkyl, mono-$C_{1-6}$ alkylamino, di-$C_{1-6}$ alkylamino, optionally fluorine-substituted $C_{1-6}$ alkyloxy, $C_{1-6}$ alkyloxy-$C_{1-6}$ alkyl, $C_{1-6}$ alkyloxycarbonyl, $C_{1-6}$ alkyloxycarbonylamino, $C_{1-6}$ alkyloxycarbonyl-($C_{1-6}$ alkyl)amino, $C_{1-6}$ alkylcarbonyl, $C_{1-6}$ alkylcarbonyloxy, $C_{1-6}$ alkylcarbonylamino, $C_{1-6}$ alkylcarbonyl-($C_{1-6}$ alkyl)amino, carbamoyl, mono-$C_{1-6}$ alkylcarbamoyl, di-$C_{1-6}$ alkylcarbamoyl, carbamoylamino, mono-$C_{1-6}$ alkylcarbamoylamino, di-$C_{1-6}$ alkylcarbamoylamino, mono-$C_{1-6}$ alkylcarbamoyl-($C_{1-6}$ alkyl)amino, di-$C_{1-6}$ alkylcarbamoyl-($C_{1-6}$ alkyl)amino, carbamoyloxy, mono-$C_{1-6}$ alkylcarbamoyloxy, di-$C_{1-6}$ alkylcarbamoyloxy, $C_{1-6}$ alkylsulfonyl, $C_{1-6}$ alkylsulfonylamino, $C_{1-6}$ alkylsulfonyl-($C_{1-6}$ alkyl)amino, sulfamoyl, mono-$C_{1-6}$ alkylsulfamoyl, di-$C_{1-6}$ alkylsulfamoyl, sulfamoylamino, mono-$C_{1-6}$ alkylsulfamoylamino, di-$C_{1-6}$ alkylsulfamoylamino, mono-$C_{1-6}$ alkylsulfamoyl-($C_{1-6}$ alkyl)amino, di-$C_{1-6}$ alkylsulfamoyl-($C_{1-6}$ alkyl)amino and pyridone, $R^6$ stands for $R^5$ or oxo, W stands for
1) linker (single bond)
2) mono- or bi-cyclic, 3 to 8-membered aromatic or aliphatic heterocyclic group,
3) mono- or bi-cyclic, 3 to 8 membered aromatic or aliphatic carbocyclic group,
4) $C_{2-4}$ alkylene in which the carbon in the main chain may be substituted with oxygen, or
5) $C_{2-4}$ alkenylene in which the carbon in the main chain may be substituted with oxygen, those substituents in above 2) through 5) being optionally substituted with $R^5$, Ar stands for optionally R⁷-substituted aromatic carbocyclic group or aromatic heterocyclic group, said aromatic carbocyclic group or aromatic heterocyclic group standing for a substituent selected from the group consisting of
1) phenyl,
2) naphthyl,
3) pyridinyl,
4) pyrimidinyl,
5) pyridazinyl,
6) pyrazyl,
7) pyrazole,
8) pyrrolyl,
9) imidazolyl,
10) triazolyl,
11) oxazolyl,
12) isoxazolyl
13) oxadiazolyl,
14) thiazolyl,
15) isothiazolyl,
16) thiadiazolyl, and
17) tetrazolyl and
$R^7$ is same as $R^5$]
or their pharmaceutically acceptable salts;
(2) imidazopyridine derivatives represented by a general formula [I-1]

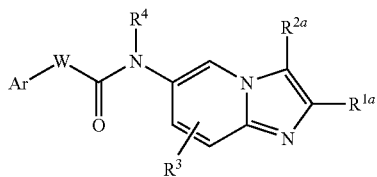

[in which
$R^{1a}$ and $R^{2a}$ stand for same or different substituents selected from the group consisting of
1) hydrogen
2) halogen
3) $C_{1-6}$ alkyl
4) $C_{3-8}$ cycloalkyl-$C_{0-4}$ alkyl
5) $C_{1-6}$ alkylamino
6) di-$C_{1-6}$ alkylamino
7) $C_{1-6}$ alkylcarbonylamino
8) $C_{1-6}$ alkylcarbonyl-($C_{1-6}$ alkyl)amino, and
9) 3 to 8-membered heterocycloalkyl, wherein $C_{1-6}$ alkyl moiety may be substituted with $R^{5a}$, cycloalkyl or heterocycloalkyl moiety may be substituted with $R^6$, and $R^{1a}$ and $R^{2a}$ are not hydrogen at the same time, or
$R^{1a}$ and $R^{2a}$ may together form —(CH₂)m-, m standing for an integer of 3-6, wherein 1 or 2 hydrogen atoms constituting methylene may be substituted with $R^6$, $R^{5a}$ stands for a substituent selected from the group consisting of halogen, cyano, hydroxyl, optionally fluorine- or hydroxyl-substituted $C_{1-6}$ alkyl, optionally fluorine-substituted $C_{1-6}$ alkyloxy, $C_{1-6}$ alkyloxy-$C_{1-16}$ alkyl, $C_{1-6}$ alkyloxycarbonyl, $C_{1-6}$ alkyloxycarbonylamino, $C_{1-6}$ alkyloxycarbonyl-($C_{1-6}$ alkyl)amino, $C_{1-6}$ alkylcarbonyl, $C_{1-6}$ alkylcarbonyloxy, $C_{1-6}$ alkylcarbonylamino, $C_{1-6}$ alkylcarbonyl-($C_{1-6}$ alkyl)amino, carbamoyl, mono-$C_{1-6}$ alkylcarbamoyl, di-$C_{1-6}$ alkylcarbamoyl, carbamoylamino, mono-$C_{1-6}$ alkylcarbamoylamino, di-$C_{1-6}$ alkylcarbamoylamino, mono-$C_{1-6}$ alkylcarbamoyl-($C_{1-6}$ alkyl)amino, di-$C_{1-6}$ alkylcarbamoyl-($C_{1-6}$ alkyl)amino, carbamoyloxy, mono-$C_{1-6}$ alkylcarbamoyloxy, di-$C_{1-6}$ alkylcarbamoyloxy, $C_{1-6}$ alkylsulfonyl, $C_{1-6}$ alkylsulfonylamino, $C_{1-6}$ alkylsulfonyl-($C_{1-6}$ alkyl) amino, sulfamoyl, mono-$C_{1-6}$ alkylsulfamoyl, di-$C_{1-6}$ alkylsulfamoyl, sulfamoylamino, mono-$C_{1-6}$ alkylsulfamoylamino, di-$C_{1-6}$ alkylsulfamoylamino, mono-$C_{1-6}$ alkylsulfamoyl-($C_{1-6}$ alkyl)amino, di-$C_{1-6}$ alkylsulfamoyl-($C_{1-6}$ alkyl)amino and pyridone, and
$R^3$, $R^4$, $R^6$, W and Ar have the same significations to those given in (1)] or their pharmaceutically acceptable salts;
(3) a method for producing a compound represented by the general formula [I] which comprises
1) a step of amidating a compound represented by a general formula [II]

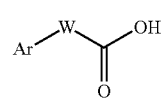

[in which Ar and W have the previously given significations]

with a compound represented by a general formula [III]

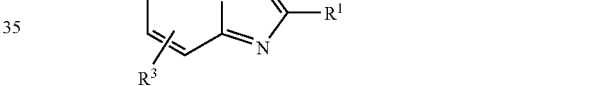

[in which $R^1$, $R^2$ and $R^3$ have the previously given significations]

and
2) a step of condensing, where $R^4$ is not hydrogen, the compound as obtained in the above step with a compound represented by a general formula [IV]

$$R^4-X_1 \qquad [IV]$$

[in which $X_1$ stands for a leaving group and $R^4$ has the previously given signification];
(4) melanin concentrating hormone receptor antagonists which contain the compounds as described in above (1) or (2) as the active ingredient;
(5) medical compositions containing the compounds as described in (1) or (2) or their pharmaceutically acceptable salts, and pharmaceutically acceptable carriers; and
(6) preventing or treating agents containing the compounds described in (1) or (2) as the active ingredient, of metabolic disorders represented by obesity, diabetes, hormone disorder, hyperlipidemia, gout, fatty liver, hepatitis and cirrhosis; cardiovascular disorders represented by stenocardia, acute or congestive heart failure, myocardial infarction, coronary atherosclerosis, hypertension, renal diseases and electrolyte abnormality; central nervous system or peripheral nervous system disorders represented by bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence and alcoholism; reproductive disorders represented by infertility, preterm labor and sexual dysfunction; digestive disorders; respiratory disorders; cancer or pigmentation.

Hereinafter the codes and terms used in the present specification are explained.

As "halogen", fluorine, chlorine, bromine and iodine can be named.

"$C_{1-6}$ alkyl" signify $C_1$-$C_6$ alkyl, i.e., $C_1$-$C_6$ straight chain or $C_3$-$C_6$ branched chain alkyl, specific examples being methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl and the like.

"$C_{3-6}$ cycloalkyl" includes $C_3$-$C_6$ cycloalkyl, specific examples being cyclopropyl, cyclobutyl, cyclopentyl and cyclohexyl.

"Oxo" signifies a group which forms carbonyl group with carbon atom in an organic compound. For example, as to $R^5$, it refers to the case where two $R^{5s}$ and the carbon atom to which they bind form carbonyl group.

"Optionally fluorine-substituted $C_{1-6}$ alkyl" includes $C_{1-6}$ alkyl and $C_{1-6}$ alkyl a part or all of whose hydrogen atoms are substituted with fluorine, specific examples of the latter fluorine-substituted $C_{1-6}$ alkyl being fluoromethyl, difluoromethyl, trifluoromethyl, 1,2-difluoroethyl and the like.

"Optionally hydroxyl-substituted $C_{1-6}$ alkyl" includes $C_{1-6}$ alkyl and $C_{1-6}$ alkyl a part of whose hydrogen atoms is(are) substituted with hydroxyl, specific examples of the latter hydroxyl-substituted $C_{1-6}$ alkyl being hydroxymethyl, 2-hydroxyethyl, 3-hydroxypropyl and the like.

"Optionally fluorine-substituted $C_{1-6}$ alkyloxy" includes those groups in which $C_{1-6}$ alkyl or fluorine-substituted $C_{1-6}$ alkyl binds to oxygen, specific examples being: as $C_{1-6}$ alkyloxy, methoxy, ethoxy, n-propyloxy, isopropyloxy, n-butyloxy, isobutoxy, tert-butoxy, n-pentyloxy and the like; and as fluorine-substituted $C_{1-6}$ alkyloxy, fluoromethoxy, difluoromethoxy, trifluoromethoxy, 1,2-difluoroethoxy and the like.

"Mono-$C_{1-6}$ alkylamino" is amino in which one of its hydrogen atoms is substituted with $C_{1-6}$ alkyl, specific examples being methylamino, ethylamino, n-propylamino, isopropylamino, n-butylamino, sec-butylamino, tert-butylamino and the like.

"Di-$C_{1-6}$ alkylamino" signifies amino whose two hydrogen atoms are substituted with $C_{1-6}$ alkyl, specific examples being dimethylamino, diethylamino, ethylmethylamino, di(n-propyl)amino, methylpropylamino, diisopropylamino and the like.

"$C_{1-6}$ alkyloxy-$C_{1-6}$ alkyl" signifies $C_{1-6}$ alkyl group one of whose hydrogen atoms is substituted with $C_{1-6}$ alkyloxy, specific examples being methoxymethyl, ethoxymethyl, n-propyloxymethyl, ethoxymethyl, ethoxyethyl and the like.

"$C_{1-6}$ alkyloxycarbonyl" is carbonyl to which $C_{1-6}$ alkyloxy is bound, specific examples being methoxycarbonyl, ethoxycarbonyl, n-propyloxycarbonyl, isopropyloxycarbonyl, n-butyloxycarbonyl, isobutoxycarbonyl, tert-butoxycarbonyl, n-pentyloxycarbonyl and the like.

"($C_{1-6}$ alkyloxycarbonyl)amino" is amino to which $C_{1-6}$ alkyloxycarbonyl is bound, specific examples being methoxycarbonylamino, ethoxycarbonylamino, n-propyloxycarbonylamino, isopropyloxycarbonylamino, n-butoxycarbonylamino, isobutoxycarbonylamino, tert-butoxycarbonylamino, n-pentyloxycarbonylamino and the like.

"($C_{1-6}$ alkyloxycarbonyl)-$C_{1-6}$ alkylamino" is a mono-$C_{1-6}$ alkylamino whose hydrogen on the nitrogen atom is substituted with $C_{1-6}$ alkyloxycarbonyl, specific examples being (methoxycarbonyl)-methylamino, (ethoxycarbonyl)methylamino, (n-propyloxycarbonyl)-methylamino and the like.

"$C_{1-6}$ alkylcarbonyl" is carbonyl to which $C_{1-6}$ alkyl is bound, specific examples being acetyl, propionyl, butyryl, isobutyryl, valeryl, isovaleryl, pivaloyl and the like.

"$C_{1-6}$ alkylcarbonyloxy" is a group formed of $C_{1-6}$ alkylcarbonyl binding to oxygen atom, specific examples being acetoxy, propionyloxy, valeryloxy, isovaleryloxy, pivaloyloxy and the like.

"$C_{1-6}$ alkylcarbonylamino" is amino whose one of hydrogen atoms is substituted with $C_{1-6}$ alkylcarbonyl, specific examples being acetamido, propionylamino, isobutyrylamino, valerylamino, isovalerylamino, pivaloylamino and the like.

"($C_{1-6}$ alkylcarbonyl)-$C_{1-6}$ alkylamino" is mono-$C_{1-6}$ alkylamino in which the hydrogen on its nitrogen atom is substituted with $C_{1-6}$ alkylcarbonyl, specific examples including (methylcarbonyl)-methylamino, (ethylcarbonyl)methylamino, (n-propylcarbonyl)-methylamino and the like.

"Mono-$C_{1-6}$ alkylcarbamoyl" is a carbamoyl one of whose hydrogen atoms is substituted with $C_{1-6}$ alkyl, specific examples including methylcarbamoyl, ethylcarbamoyl, n-propylcarbamoyl, isopropylcarbamoyl, n-butylcarbamoyl, sec-butylcarbamoyl, tert-butylcarbamoyl and the like.

"Di-$C_{1-6}$ alkylcarbamoyl" is a carbamoyl whose two hydrogen atoms are substituted with $C_{1-6}$ alkyl, specific examples including dimethylcarbamoyl, diethylcarbamoyl, ethylmethylcarbamoyl, di(n-propyl)carbamoyl, methylpropylcarbamoyl, diisopropylcarbamoyl and the like.

"Mono-$C_{1-6}$ alkylcarbamoylamino" is an amino one of whose hydrogen atoms is substituted with $C_{1-6}$ alkylcarbamoyl, specific examples including methylcarbamoylamino, ethylcarbamoylamino, n-propylcarbamoylamino, isopropylcarbamoylamino, n-butylcarbamoylamino, sec-butylcarbamoylamino, tert-butylcarbamoylamino and the like.

"Di-$C_{1-6}$ alkylcarbamoylamino" is an amino one of whose hydrogen atoms is substituted with di-$C_{1-6}$ alkylcarbamoyl, specific examples including dimethylcarbamoylamino, diethylcarbamoylamino, di(n-propyl)carbamoylamino, diisopropylcarbamoylamino, di(n-butyl)carbamoylamino, di(sec-butyl)carbamoylamino, di(tert-butyl)carbamoylamino and the like.

"(Mono-$C_{1-6}$ alkylcarbamoyl)-$C_{1-6}$ alkylamino" is a mono-$C_{1-6}$ alkylamino whose hydrogen on the nitrogen atom is substituted with mono-$C_{1-6}$ alkylcarbamoyl, specific examples including (monomethylcarbamoyl)methylamino, (monoethylcarbamoyl)methylamino, [mono(n-propyl)carbamoyl]methylamino and the like.

"(Di-$C_{1-6}$ alkylcarbamoyl)-$C_{1-6}$ alkylamino" is a mono-$C_{1-6}$ alkylamino whose hydrogen atom on the nitrogen atom is substituted with di-$C_{1-6}$ alkylcarbamoyl, specific examples including (dimethylcarbamoyl)methylamino, (diethylcarbamoyl)methylamino, [di(n-propyl)carbamoyl]methylamino and the like.

"Mono-$C_{1-6}$ alkylcarbamoyloxy" is a group in which $C_{1-6}$ alkylcarbamoyl binds to oxygen, specific examples including methylcarbamoyloxy, ethylcarbamoyloxy, n-propylcarbamoyloxy, isopropylcarbamoyloxy, n-butylcarbamoyloxy, sec-butylcarbamoyloxy, tert-butylcarbamoyloxy and the like.

"Di-$C_{1-6}$ alkylcarbamoyloxy" is a group in which di-$C_{1-6}$ alkylcarbamoyl binds to oxygen, specific examples including dimethylcarbamoyloxy, diethylcarbamoyloxy, ethylmethylcarbamoyloxy, di(n-propyl)carbamoyloxy, methylpropylcarbamoyloxy, diisopropylcarbamoyloxy and the like.

"$C_{1-6}$ alkylsulfonyl" is a group in which $C_{1-6}$ alkyl binds to sulfonyl, specific examples including methylsulfonyl, ethylsulfonyl, n-propylsulfonyl, isopropylsulfonyl, n-butylsulfonyl, sec-butylsulfonyl, tert-butylsulfonyl and the like.

"$C_{1-6}$ alkylsulfonylamino" is an amino one of whose hydrogen atoms is substituted with $C_{1-6}$ alkylsulfonyl, specific examples including methylsulfonylamino, ethylsulfonylamino, n-propylsulfonylamino, isopropylsulfonylamino, n-butylsulfonylamino, sec-butylsulfonylamino, tert-butylsulfonylamino and the like.

"$C_{1-6}$ alkylsulfonyl-($C_{1-6}$ alkyl)amino" is a group in which hydrogen on the nitrogen atom of "$C_{1-6}$ alkylamino" is substituted with $C_{1-6}$ alkylsulfonyl, specific examples including methylsulfonyl(methyl)amino, ethylsulfonyl(methyl)amino, (n-propyl)sulfonyl(methyl)amino and the like.

"Mono-$C_{1-6}$ alkylsulfamoyl" is a group in which $C_{1-6}$ alkyl binds to sulfamoyl, specific examples including monomethyl-sulfamoyl, monoethylsulfamoyl, mono(n-propyl)sulfamoyl, monoisopropylsulfamoyl, mono(n-butyl)sulfamoyl, mono(sec-butyl)sulfamoyl, mono(tert-butyl)sulfamoyl and the like.

"Di-$C_{1-6}$ alkylsulfamoyl" is a group in which di-$C_{1-6}$ alkyl binds to sulfamoyl, specific examples including dimethylsulfamoyl, diethylsulfamoyl, di(n-propyl)sulfamoyl, diisopropylsulfamoyl, di(n-butyl)sulfamoyl, di(sec-butyl)sulfamoyl, di(tert-butyl)sulfamoyl and the like.

"(Mono-$C_{1-6}$ alkylsulfamoyl)amino" is an amino one of whose hydrogen atoms is substituted with $C_{1-6}$ alkylsulfamoyl, specific examples including (monomethylsulfamoyl)amino, (monoethylsulfamoyl)amino, [mono(n-propyl)sulfamoyl]amino, (monoisopropylsulfamoyl)amino, [mono(n-butyl)sulfamoyl]amino, [mono(sec-butyl)sulfamoyl]amino, (tert-butylsulfamoyl)amino and the like.

"(Di-$C_{1-6}$ alkylsulfamoyl)amino" is an amino one of whose hydrogen atoms is substituted with di-$C_{1-6}$ alkylsulfamoyl, specific examples including (dimethylsulfamoyl)amino, (diethylsulfamoyl)amino, (ethylmethylsulfamoyl)amino, [di(n-propyl)sulfamoyl]amino, (methylpropylsulfamoyl)amino, (diisopropylsulfamoyl)amino and the like.

"Mono-$C_{1-6}$ alkylsulfamoyl-($C_{1-6}$ alkyl)amino" is a "mono-$C_{1-6}$ alkylamino" whose hydrogen on the nitrogen atom is substituted with mono-$C_{1-6}$ alkylsulfamoyl, specific examples including monomethylsulfamoyl(methyl)amino, monoethylsulfamoyl(methyl)amino, mono(n-propyl)sulfamoyl(methyl)amino and the like.

"Di-$C_{1-6}$ alkylsulfamoyl-($C_{1-6}$ alkyl)amino" is a "mono-$C_{1-6}$ alkylamino" whose hydrogen on the nitrogen atom is substituted with di-$C_{1-6}$ alkylsulfamoyl, specific examples including dimethylsulfamoyl(methyl)amino, diethylsulfamoyl(methyl)amino, di(n-propyl)sulfamoyl(methyl)amino and the like.

As "3 to 8-membered heterocycloalkyl", azetidinyl, pyrrolidinyl, piperidinyl, piperazinyl, imidazolidinyl, tetrahydrofuranyl, tetrahydropyranyl, morpholinyl, 1-thia-4-azocyclohexyl, 2,5-diazabicyclo[2.2.2]octanyl and the like can be named.

"Pharmaceutically acceptable salts" of the compounds which are represented by the general formula [I] signify those customarily used, medically acceptable salts, specific examples including acid addition salts at amino, acid addition salts at nitrogen-containing heterocycle or, where the compounds have carboxyl groups, base addition salts at the carboxyl.

As such acid addition salts, inorganic acid salts such as hydrochloride, sulfate, nitrate, phosphate, perchlorate and the like; organic acid salts such as maleate, fumarate, tartarate, citrate, ascorbate, trifluoroacetate and the like; and sulfonic acid salts such as methanesulfonate, isethionate, benzenesulfonate, p-toluenesulfonate and the like can be named.

As the base addition salts, alkali metal salts such as sodium salt, potassium salt and the like; alkaline earth metal salts such as calcium salt, magnesium salt and the like; and organic amine salts such as ammonium salt, trimethylamine salt, triethylamine salt, dicyclohexylamine salt, ethanolamine salt, diethanolamine salt, triethanolamine salt, procaine salts, N,N'-dibenzylethylenediamine salt and the like can be named.

For disclosing the imidazolidine derivatives of the present invention still more specifically, those various codes used in the formula [I] are hereinafter explained in further details, citing specific examples. The position numbers of imidazolidine skeletal structure are as follows.

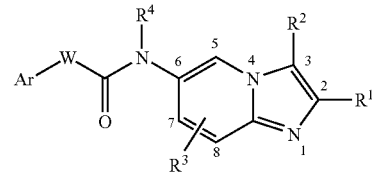

[I]

Compounds Represented by the General Formula [I]

In the compounds represented by the general formula [I], $R^1$ and $R^2$ stand for same or different substituents selected from the group consisting of
1) hydrogen
2) halogen
3) $C_{1-6}$ alkyl
4) $C_{3-8}$ cycloalkyl-$C_{0-4}$ alkyl
5) $C_{1-6}$ alkylamino
6) di-$C_{1-6}$ alkylamino
7) $C_{1-6}$ alkylcarbonylamino
8) $C_{1-6}$ alkylcarbonyl-($C_{1-6}$ alkyl)amino, and 9) 3 to 8-membered heterocycloalkyl-$C_{0-4}$ alkyl, wherein $C_{1-6}$ alkyl moiety may be substituted with $R^5$, cycloalkyl or heterocycloalkyl moiety may be substituted with $R^6$, and $R^1$ and $R^2$ are not hydrogen at the same time, or $R^1$ and $R^2$ may together form —$(CH_2)m$-, m standing for an integer of 3-6, wherein 1 or 2 hydrogen atoms constituting methylene may be substituted with $R^6$.

Also referring to the general formula [I-1], $R^{1a}$ and $R^{2a}$ stand for same or different substituents selected from the group consisting of
1) hydrogen
2) halogen
3) $C_{1-6}$ alkyl
4) $C_{3-8}$ cycloalkyl-$C_{0-4}$ alkyl
5) $C_{1-6}$ alkylamino
6) di-$C_{1-6}$ alkylamino
7) $C_{1-6}$ alkylcarbonylamino
8) $C_{1-6}$ alkylcarbonyl-($C_{1-6}$ alkyl)amino, and 9) 3 to 8-membered heterocycloalkyl, wherein $C_{1-6}$ alkyl moiety may be substituted with $R^{5a}$, cycloalkyl or heterocycloalkyl moiety may be substituted with $R^6$, and $R^{1a}$ and $R^{2a}$ are not hydrogen at the same time, or $R^{1a}$ and $R^{2a}$ may together form —$(CH_2)_m$—, m standing for an integer of 3-6, wherein 1 or 2 hydrogen atoms constituting methylene may be substituted with $R^6$.

As $R^5$, halogen, cyano, hydroxyl, amino, optionally fluorine- or hydroxyl-substituted $C_{1-6}$ alkyl, mono-$C_{1-6}$ alkylamino, di-$C_{1-6}$ alkylamino, optionally fluorine-substituted $C_{1-6}$ alkyloxy, $C_{1-6}$ alkyloxy-$C_{1-6}$ alkyl, $C_{1-6}$ alkyloxycarbonylamino, $C_{1-6}$ alkyloxycarbonyl-($C_{1-6}$ alkyl)amino, $C_{1-6}$ alkylcarbonyl, $C_{1-6}$ alkylcarbonyloxy, $C_{1-6}$ alkylcarbonylamino, $C_{1-6}$ alkylcarbonyl-($C_{1-6}$ alkyl)amino, carbamoyl, mono-$C_{1-6}$ alkylcarbamoyl, di-$C_{1-6}$ alkylcarbamoyl, carbamoylamino, mono-$C_{1-6}$ alkylcarbamoylamino, di-$C_{1-6}$ alkylcarbamoylamino, mono-$C_{1-6}$ alkylcarbamoyl-($C_{1-6}$ alkyl)amino, di-$C_{1-6}$ alkylcarbamoyl-($C_{1-6}$ alkyl)amino, carbamoyloxy, mono-$C_{1-6}$ alkylcarbamoyloxy, di-$C_{1-6}$ alkylcarbamoyloxy, $C_{1-6}$ alkylsulfonyl, $C_{1-6}$ alkylsulfonylamino, $C_{1-6}$ alkylsulfonyl-($C_{1-6}$ alkyl)amino, sulfamoyl, mono-$C_{1-6}$ alkylsulfamoyl, di-$C_{1-6}$ alkylsulfamoyl, sulfamoylamino, mono-$C_{1-6}$ alkylsulfamoylamino, di-$C_{1-6}$ alkylsulfamoylamino, mono-$C_{1-6}$ alkylsulfamoyl-($C_{1-6}$ alkyl)amino, di-$C_{1-6}$ alkylsulfamoyl-($C_{1-6}$ alkyl)amino, pyridone and the like can be named.

As $R^{5a}$, halogen, cyano, hydroxyl, optionally fluorine- or hydroxyl-substituted $C_{1-6}$ alkyl, optionally fluorine-substituted $C_{1-6}$ alkyloxy, $C_{1-6}$ alkyloxy-$C_{1-6}$ alkyl, $C_{1-6}$ alkyloxycarbonyl, $C_{1-6}$ alkyloxycarbonylamino, $C_{1-6}$ alkyloxycarbonyl-($C_{1-6}$ alkyl)amino, $C_{1-6}$ alkylcarbonyl, $C_{1-6}$ alkylcarbonyloxy, $C_{1-6}$ alkylcarbonylamino, $C_{1-6}$ alkylcarbonyl-($C_{1-6}$ alkyl)amino, carbamoyl, mono-$C_{1-6}$ alkylcarbamoyl, di-$C_{1-6}$ alkylcarbamoyl, carbamoylamino, mono-$C_{1-6}$ alkylcarbamoylamino, di-$C_{1-6}$ alkylcarbamoylamino, mono-$C_{1-6}$ alkylcarbamoyl-($C_{1-6}$ alkyl)amino, di-$C_{1-6}$ alkylcarbamoyl-($C_{1-6}$ alkyl)amino, carbamoyloxy, mono-$C_{1-6}$ alkylcarbamoyloxy, di-$C_{1-6}$ alkylcarbamoyloxy, $C_{1-6}$ alkylsulfonyl, $C_{1-6}$ alkylsulfonylamino, $C_{1-6}$ alkylsulfonyl-($C_{1-6}$ alkyl) amino, sulfamoyl, mono-$C_{1-6}$ alkylsulfamoyl, di-$C_{1-6}$ alkylsulfamoyl, sulfamoylamino, mono-$C_{1-6}$ alkylsulfamoylamino, di-$C_{1-6}$ alkylsulfamoylamino, mono-$C_{1-6}$ alkylsulfamoyl-($C_{1-6}$ alkyl)amino, di-$C_{1-6}$ alkylsulfamoyl-($C_{1-6}$ alkyl)amino, pyridine and the like can be named.

As $R^5$ or $R^{5a}$ which may substitute on $R^1$ or $R^{1a}$, in particular, hydroxyl, methoxycarbonyl and ethoxycarbonyl are recommended.

As $R^6$, $R^5$ or oxo can be named for example, in particular, hydroxyl, methoxycarbonyl, ethoxycarbonyl and oxo are recommended.

In $R^1$, $R^2$, $R^{1a}$ or $R^{2a}$, as the heteroalkyl moiety in 3 to 8-membered heteroalkyl-$C_{0-4}$-alkyl or 3 to 8-membered heterocycloalkyl, tetrahydrofuranyl, tetrahydropyranyl, pyrrolidinyl or piperidinyl can be named for example.

As preferred $R^1$ (or $R^{1a}$), $C_{1-6}$ alkyl, $C_{3-8}$ cycloalkyl-$C_{0-4}$ alkyl, $C_{1-6}$ alkylamino, di-$C_{1-6}$ alkylamino, $C_{1-6}$ alkylcarbonyl-($C_{1-6}$ alkyl)amino and the like are named for example, in which optional hydrogen in the alkyl moiety may be substituted with $R^5$ (or $R^{5a}$) and optional hydrogen in the cycloalkyl moiety may be substituted with $R^6$. Specific examples of $R^1$ (or $R^{1a}$) include methyl, ethyl, n-propyl, isopropyl, n-butyl, t-butyl, hydroxymethyl, 1-hydroxyethyl, 1-methyl-1-hydroxyethyl, cyclopropyl, N-methylacetaminomethyl, 2-ethoxycarbonyl-2-propyl, 1H-pyridin-2-on-ylmethyl, pyrrolidon-2-on-ylmethyl, N-methyl-methylsulfonylaminomethyl and the like, in particular, methyl, ethyl, isopropyl, t-butyl, hydroxymethyl, 1-methyl-1-hydroxyethyl and cyclopropyl being recommended.

As preferred $R^2$ (or $R^{2a}$), hydrogen, optionally $R^5$ (or $R^{5a}$)-substituted $C_{1-6}$ alkyl and optionally $R^6$-substituted $C_{3-6}$ cycloalkyl can be named for example. As specific examples, hydrogen, methyl, ethyl, hydroxymethyl, 1-hydroxyethyl, cyclopropyl, methoxymethyl, cyanomethyl and the like can be named, in particular, hydrogen, methyl and hydroxymethyl being recommended.

Furthermore, as —$(CH_2)_m$— which is formed by $R^1$ and $R^2$ (or $R^{1a}$ and $R^{2a}$) together, for example the following can be named:

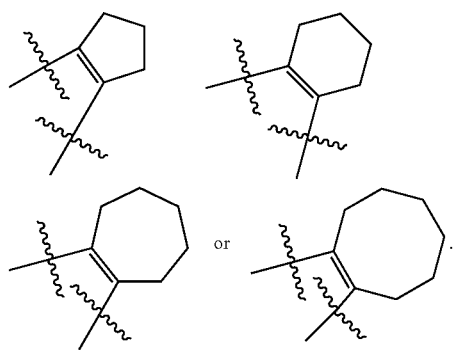

As $R^3$, hydrogen, halogen, $C_{1-6}$ alkyl or $C_{1-6}$ alkyloxy can be named for example, specific examples including hydrogen, fluorine, chlorine, methyl, ethyl, n-propyl, isopropyl, n-butyl, t-butyl, methoxy, ethoxy, n-propyloxy, isopropyloxy, n-butyloxy and the like. Preferably, hydrogen, methyl and methoxy are recommended.

$R^4$ stands for hydrogen or $C_{1-6}$ alkyl, specific examples including hydrogen, methyl, ethyl, n-propyl, isopropyl, n-butyl and the like. Preferably, hydrogen and methyl are recommended.

As W,
1) linker (single bond)
2) mono- or bi-cyclic, 3 to 8-membered aromatic or aliphatic heterocyclic group,
3) mono- or bi-cyclic, 3 to 8 membered aromatic or aliphatic carbocyclic group,
4) $C_{2-4}$ alkylene in which the carbon in the main chain may be substituted with oxygen, or
5) $C_{2-4}$ alkenylene in which the carbon in the main chain may be substituted with oxygen,
those substituents in above 2) through 5) being optionally substituted with $R^5$ Specific examples of W include, besides linker,
1) pyrrol-di-yl, pyridazin-di-yl, 1,2,4-triazin-di-yl, oxazol-di-yl, isoxazol-di-yl, 1,2,4-oxadiazol-di-yl, 1,3,4-oxadiazol-di-yl, 1,2,4-triazol-di-yl, 1,2,3-triazol-di-yl, pyrazol-di-yl, 5-methylpyrazol-di-yl, 1-methylpyrazol-di-yl, tetrazol-di-yl, thiazol-di-yl, isothiazol-di-yl, thiadiazol-di-yl, imidazol-di-yl, indol-di-yl, benzimidazol-di-yl, benzoxazol-di-yl, benzoisoxazol-di-yl, benzothiazol-di-yl, benzoisothiazol-di-yl, indazolin-di-yl, prinin-di-yl, quinolin-di-yl, isoquinolin-di-yl, phthaladin-di-yl, naphthyridin-di-yl, quinoxalin-di-yl, quinazolin-di-yl, cinnolin-di-yl, pteridin-di-yl, aziridin-di-yl, pyrrolidin-di-yl, piperazin-di-yl, piperazin-2-on-di-yl, piperidin-di-yl and the like;
2) pyridin-2,5-di-yl, pyrimidin-2,5-di-yl, pyrazin-2,5-di-yl, 1,4-piperidin-di-yl, 1,2,4-triazol-1,3-di-yl and the like;

3) 1,3-phenylene, 1,4-phenylene, 2-fluoro-1,4-phenylene, 2,6-naphthalen-di-yl, 1,4-cyclohexylene, 1,2-cyclohexylene, 1,2-cyclopropylene, 1,3-cyclobutylene, 1,3-cyclopentylene and the like; and 4) 1,2-dimethylene (—CH$_2$CH$_2$—), 1,3-trimethylene (—CH$_2$CH$_2$CH$_2$—), 1-methyl-1,2-dimethylene [—CH$_2$CH(CH$_3$)—], oxymethylene (—O—CH$_2$), tetramethylene (—CH$_2$CH$_2$CH$_2$CH$_2$—) and the like.

As preferred W, 1,2-dimethylene, 1,4-phenylene, 2-fluoro-1,4-phenylene, pyridin-2,5-di-yl, pyrimidin-2,5-di-yl, pyrazin-2,5-di-yl, 1,4-piperidin-di-yl, 1,2,4-triazol-1,3-di-yl, 1,4-cyclohexylene or oxymethylene can be named. In particular, 1,2-dimethylene, 1,4-phenylene, 2-fluoro-1,4-phenylene, pyridine-2,5-di-yl, pyrimidin-2,5-di-yl, pyrazin-2,5-di-yl, 1,2,4-triazol-1,3-di-yl and 1,4-cyclohexylene are recommended.

Ar is an aromatic carbocyclic group or aromatic heterocyclic group, which may be substituted with R$^7$. The aromatic carbocyclic or heterocyclic group is selected from the group consisting of 1) phenyl,
2) naphthyl,
3) pyridinyl,
4) pyrimidinyl,
5) pyridazinyl,
6) pyrazyl,
7) pyrazole,
8) pyrrolyl,
9) imidazolyl,
10) triazolyl,
11) oxazolyl,
12) isoxazolyl
13) oxadiazolyl,
14) thiazolyl,
15) isothiazolyl,
16) thiadiazolyl, and
17) tetrazolyl and R$^7$ is same as R$^5$.

Specific examples of R$^7$ include chloro, fluoro, methyl, difluoromethyl, trifluoromethyl, methoxy, difluoromethoxy, trifluoromethoxy, methanesulfonyl and the like.

Specific examples of Ar include phenyl, 2-fluorophenyl, 3-fluorophenyl, 4-fluorophenyl, 4-chlorophenyl, 3,4-difluorophenyl, 2,4-difluorophenyl, 2-trifluoromethylphenyl, 3-trifluoromethylphenyl, 4-trifluoromethylphenyl, 4-methoxyphenyl, 4-methanesulfonylphenyl, 3-fluoro-4-methoxyphenyl, naphthyl, pyridinyl, 3-trifluoromethylpyridin-6-yl, 2-trifluoromethylpyridin-5-yl, 2-fluoropyridin-5-yl, 3-fluoropyridin-6-yl, 3-chloropyridin-6-yl, 2-methoxypyridin-5-yl, 3-methoxypyridin-6-yl, 2-difluoromethoxypyridin-5-yl, 3-difluoromethoxypyridin-6-yl, 2-pyrazinyl, 2-pyrimidinyl, 5-trifluoromethylpyrimidin-2-yl, 2-trifluoromethylpyrimidin-5-yl, 3-trifluoromethyl-6-pyridinyl, 3-pyridazinyl, pyrrol-1-yl, 2-imidazolyl, 1-imidazoyl, triazolyl, 3-isoxazolyl, 1,3,4-oxadiazol-2-yl, 5-methyl-1,3,4-oxadiazol-2-yl, 2-thiazolyl, thiadiazolyl, tetrazolyl, 2-methylpyridin-5-yl, 3-methylpyridin-6-yl, 2-difluoromethylpyridin-5-yl, 3-difluoromethylpyridin-6-yl, 2-trifluoromethoxypyridin-5-yl, 3-trifluoromethoxypyridin-6-yl and the like.

As preferred Ar, pyrrol-1-yl, phenyl, 2-fluorophenyl, 3-fluorophenyl, 4-fluorophenyl, 4-chlorophenyl, 3,4-difluorophenyl, 2,4-difluorophenyl, 2-trifluoromethylphenyl, 3-trifluoromethylphenyl, 4-trifluoromethylphenyl, 4-methoxyphenyl, 4-methanesulfonylphenyl, pyridin-2-yl, 3-methylpyridin-6-yl, 2-difluoromethylpyridin-5-yl, 3-difluoromethylpyridin-6-yl, 2-fluoropyridin-5-yl, 3-fluoropyridin-6-yl, 3-chloropyridin-6-yl, 2-methoxypyridin-5-yl, 2-methoxypyridin-6-yl, 3-methoxypyridin-6-yl, 2-difluoromethoxypyridin-5-yl, 3-difluoromethoxypyridin-6-yl, 3-trifluoromethylpyridin-6-yl, 2-trifluoromethylpyridin-5-yl, 2-pyrimidinyl, 2-pyrazinyl and 3-pyridazinyl can be named for example.

In particular, 3-difluoromethoxypyridin-6-yl, 4-fluorophenyl, 4-chlorophenyl, 4-trifluoromethylphenyl, 4-methoxyphenyl, 4-methanesulfonylphenyl, pyridin-2-yl, 2-fluoropyridin-5-yl, 3-fluoropyridin-6-yl, 3-chloropyridin-6-yl, 2-methoxypyridin-5-yl, 3-methoxypyridin-6-yl, 3-trifluoromethylpyridin-6-yl and 2-trifluoromethylpyridin-5-yl are recommended.

Specific examples of the compounds represented by the general formula [I] are shown in the following Tables 1-3.

TABLE 1

| No | Formula |
|----|---------|
| 1 |  |

TABLE 1-continued

| No | Formula |
|---|---|
| 2 | 4'-fluoro-N-(2-isopropylimidazo[1,2-a]pyridin-6-yl)biphenyl-4-carboxamide |
| 3 | N-(2,3-dimethylimidazo[1,2-a]pyridin-6-yl)-4'-(trifluoromethyl)biphenyl-4-carboxamide |
| 4 | N-(3-methylimidazo[1,2-a]pyridin-6-yl)-4'-(trifluoromethyl)biphenyl-4-carboxamide |
| 5 | N-(2-tert-butylimidazo[1,2-a]pyridin-6-yl)-4'-(trifluoromethyl)biphenyl-4-carboxamide |
| 6 | N-(2-cyclopropyl-3-methylimidazo[1,2-a]pyridin-6-yl)-4'-(trifluoromethyl)biphenyl-4-carboxamide hydrochloride |

TABLE 1-continued
| No | Formula |
|---|---|
| 7 | 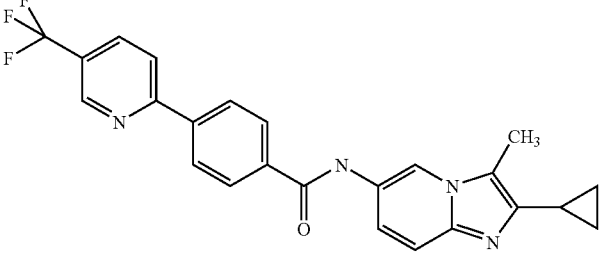 H—Cl |
| 8 | 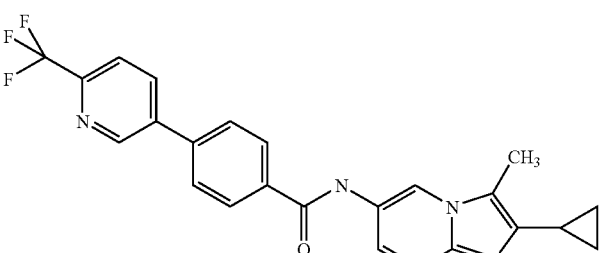 ClH |
| 9 | 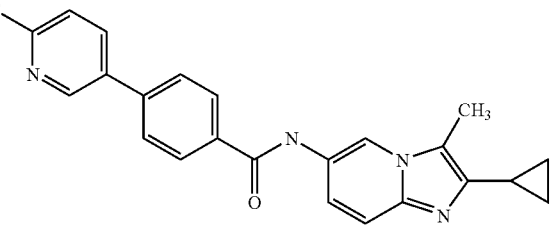 ClH |
| 10 | 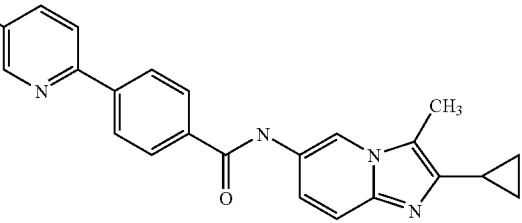 |
| 11 | 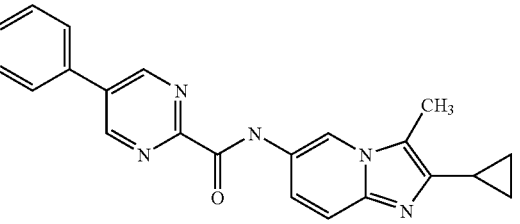 ClH |

TABLE 1-continued

| No | Formula |
|---|---|
| 12 | (3-fluorophenyl)-pyrimidine-carboxamide-N-(3-methyl-2-cyclopropyl-imidazo[1,2-a]pyridin-6-yl), ClH |
| 13 | (4-fluorophenyl)-pyrazine-carboxamide-N-(3-methyl-2-cyclopropyl-imidazo[1,2-a]pyridin-6-yl), ClH |
| 14 | (4-fluorophenyl)-pyridine-carboxamide-N-(3-methyl-2-cyclopropyl-imidazo[1,2-a]pyridin-6-yl), ClH |
| 15 | (4-fluorophenyl)-pyridine-carboxamide-N-(3-methyl-2-cyclopropyl-imidazo[1,2-a]pyridin-6-yl), ClH·ClH |
| 16 | [5-(trifluoromethyl)pyridin-2-yl]-phenyl-carboxamide-N-[3-methyl-2-(tetrahydrofuran-3-yl)-imidazo[1,2-a]pyridin-6-yl] |

TABLE 2
| No | Formula |
|---|---|
| 17 | 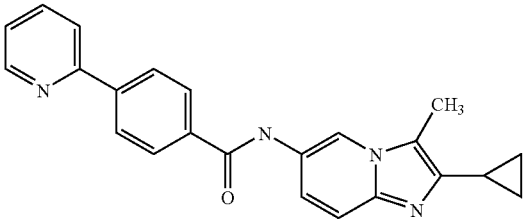 |
| 18 | 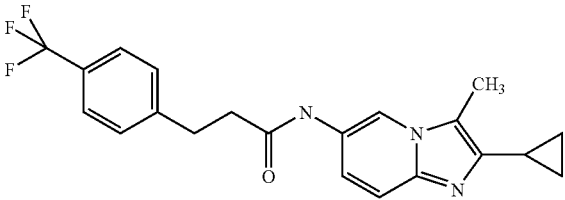 |
| 19 | 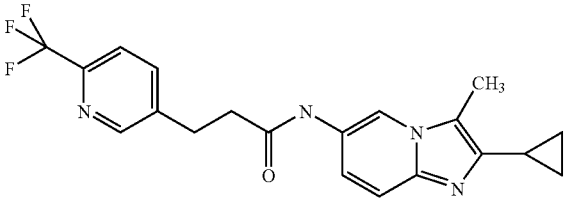 |
| 20 | 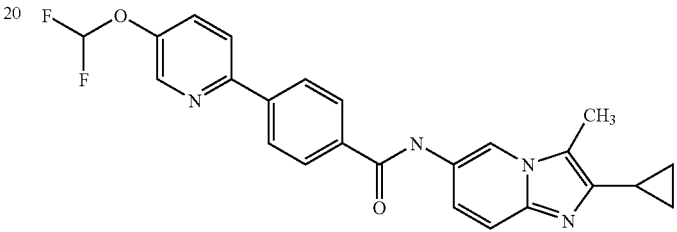 |
| 21 | 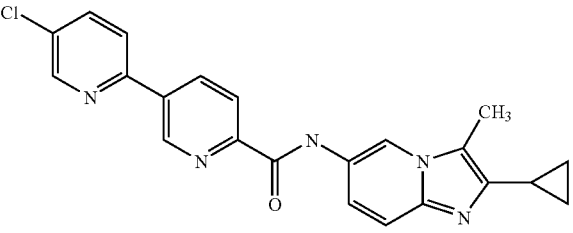 |
| 22 | 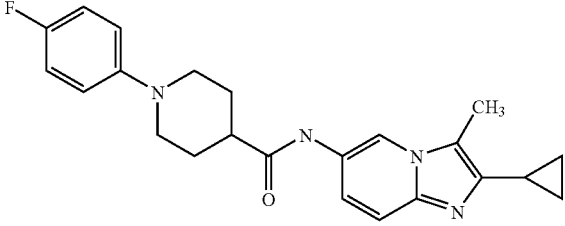 |

TABLE 2-continued

| No | Formula |
| --- | --- |
| 23 | (structure) |
| 24 | (structure) |
| 25 | (structure) |
| 26 | (structure) |
| 27 | (structure) |
| 28 | (structure) |

TABLE 2-continued

| No | Formula |
|---|---|
| 29 | 4-(5-methoxypyridin-2-yl)-N-(2-cyclopropyl-3-methylimidazo[1,2-a]pyridin-6-yl)benzamide |
| 30 | 4-(5-methylpyridin-2-yl)-N-(2-cyclopropyl-3-methylimidazo[1,2-a]pyridin-6-yl)benzamide |
| 31 | 4'-(trifluoromethyl)-N-(2-(2-hydroxypropan-2-yl)imidazo[1,2-a]pyridin-6-yl)-[1,1'-biphenyl]-4-carboxamide |
| 32 | 4-(5-(trifluoromethyl)pyridin-2-yl)-N-(2-(2-hydroxypropan-2-yl)-3-methylimidazo[1,2-a]pyridin-6-yl)benzamide |

TABLE 3

| No | Formula |
|---|---|
| 33 | 4-(5-chloropyridin-2-yl)-N-(2-(2-hydroxypropan-2-yl)-3-methylimidazo[1,2-a]pyridin-6-yl)benzamide |

TABLE 3-continued
| No | Formula |
|---|---|
| 34 | 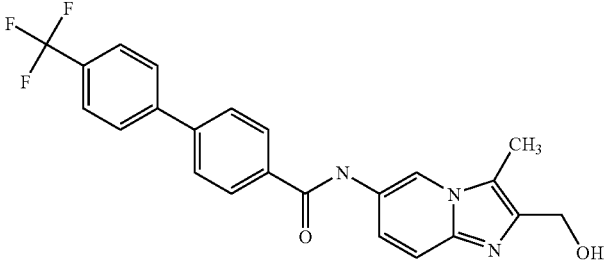 |
| 35 | 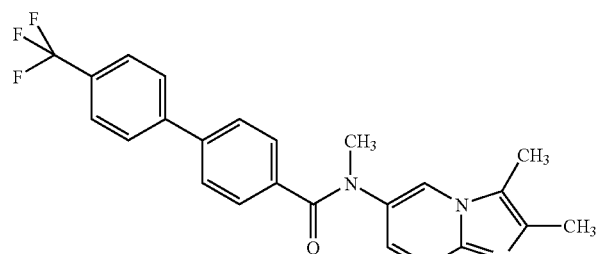 |
| 36 | 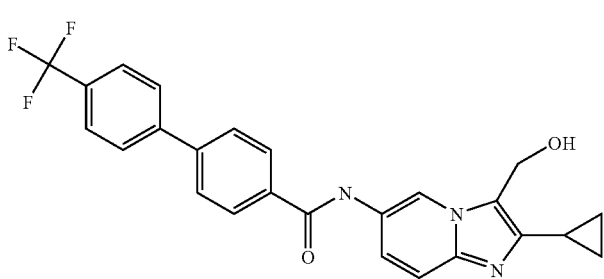 |
| 37 | 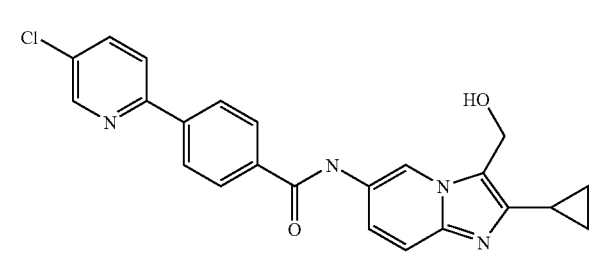 |
| 38 | 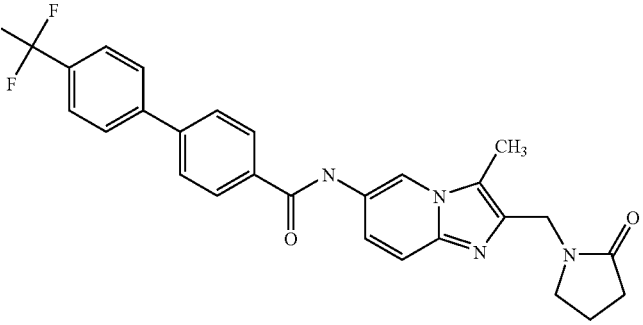 |

TABLE 3-continued

| No | Formula |
|---|---|
| 39 | (structure) |
| 40 | (structure) |
| 41 | (structure) |
| 42 | (structure) |

Of those compounds represented by the general formula [I], particularly the compounds represented by the following general formula [I-1]

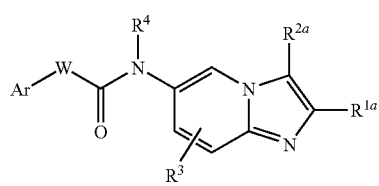

[I-1]

[in the formula, $R^{1a}$, $R^{2a}$, $R^3$. $R^4$, W and Ar have the previously given significations]

are recommended. Inter alia, N-(2,3-dimethylimidazo-[1,2-a]pyridin-6-yl)-4'-(trifluoromethyl)[1,1'-biphenyl]-4-carboxamide, N-(2-cyclopropyl-3-methylimidazo[1,2-a]pyridin-6-yl)-4-(2-pyridyl)-benzamide, N-(2-cyclopropyl-3-methylimidazo[1,2-a]pyridin-6-yl)-4-(1H-pyrrol-1-yl) benzamide and the like are recommended.

Preparation Methods of the Compounds Represented by the General Formula [I]

Those compounds represented by the general formula [I] can be prepared by, for example, suitably combining the following preparation processes.

Preparation Process 1

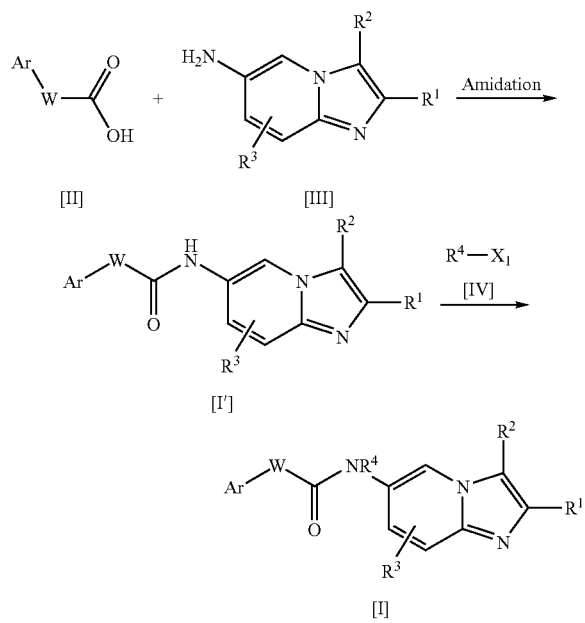

[in which $X_1$ stands for a leaving group such as halogen, e.g., chlorine, bromine, iodine and the like; arylsulfonyloxy, e.g., p-toluenesulfonyloxy, benzenesulfonyloxy; and alkanesulfonyloxy, e.g., methanesulfonyloxy, trifluoromethanesulfonyloxy or the like, and $R^1$, $R^2$, $R^3$, $R^4$, W and Ar are the same to the previously given significations].

This process comprises

Step 1-1: a step for amidating a compound represented by the general formula [II] and a compound represented by the general formula [III] in a solvent to form a compound represented by the general formula [I'], and Step 1-2: a step for condensing, where necessary, the compound represented by the general formula [I'] with a compound represented by the general formula [IV] to form a compound of the general formula [I].

Step 1-1: The amidative condensation reaction can be conducted by heretofore known amidation methods which are used in peptide synthesis, for example, those taught in "Fundamentals and Experiments of Peptide Synthesis", (Nobuo IZUMIYA, et al., Maruzen Publishing Co., 1983).

This reaction is usually conducted in an inert solvent, for example, halogenated hydrocarbon such as methylene chloride, chloroform and the like; ether such as diethyl ether, tetrahydrofuran ("THF"), 1,4-dioxane ("dioxane") and the like; acetonitrile, dimethylformamide ("DMF"), dimethylsulfoxide ("DMSO"), pyridine and the like, or their mixed solvent.

Preferably, the amidation reaction is carried out in the presence of a condensing agent. As the condensing agent, for example, N,N'-dicyclohexylcarbodiimide, 2-chloro-1,3-dimethyl-2-imidazolium chloride, N,N'-diisopropylcarbodiimide, 1-(3-dimethylaminopropyl)-3-ethylcarbodiimide, 1-(3-dimethylaminopropyl)-3-ethylcarbodiimide hydrochloride ("WSC-HCl"), benzotriazol-1-yloxy-tris-(dimethylamino)-phosphoniumhexafluorophosphate, benzotriazol-1-yloxy-tris-pyrrolidinophosphoniumhexafluorophosphate, bromot-ris-(dimethylamino)phosphoniumhexafluorophosphate, diphenylphosphoric acid azide, 1,1'-carbonyldiimidazole, O-(7-azabenzotriazol-1-yl)-1,1,3,3-tetramethyluronium-hexafluorophosphate ("HATU") and the like can be named.

As the use rate of the condensing agent, it can be normally from 1 mole to molar excess, preferably 1 mole-1.5 moles, per mole of the compound of general formula [II].

The reaction temperature normally ranges, for example, −50° C.-100° C., preferably −20° C.-50° C.

The reaction time normally ranges, for example, 30 minutes-7 days, preferably 1 hour-24 hours.

Compounds represented by the general formula [1] can also be prepared through the above reaction in which a carboxylic acid represented by the general formula [II] is replaced with a reactive derivative of the carboxylic acid and reacted with a compound of the general formula [III].

As such reactive derivatives of a carboxylic acid of the general formula [II], for example, acid halides, mixed acid anhydrides, active esters, active amides and the like can be used. These reactive derivatives can be readily prepared, referring to the earlier cited "Fundamentals and Experiments of Peptide Synthesis" (Nobuo IZUMIYA, et al., Maruzen Publishing Co., 1983).

Acid halides of the compounds represented by the general formula [II] can be obtained by reacting the compounds with halogenating agent following heretofore known methods. As the halogenating agent, for example, thionyl chloride, phosphorus trichloride, phosphorus pentachloride, phosphorus oxychloride, phosphorus tribromide, oxalyl chloride, phosgene and the like can be named.

Mixed acid anhydrides of the compounds represented by the general formula [II] can be obtained, following heretofore known methods, by reacting the compounds of the general formula [II] with alkyl chlorocarbonate such as ethyl chlorocarbonate, isobutyl chlorocarbonate and the like; or aliphatic carboxylic acid chloride such as pivaloyl chloride and the like, in the presence of an amine such as triethylamine.

Active esters of the compounds represented by the general formula [II] can be obtained by reacting the compounds of the general formula [II], following heretofore known methods, for example, with N-hydroxy compound such as N-hydroxysuccinimide, N-hydroxyphthalimide, 1-hydroxy benzotriazole ("HOBt") and the like; or phenolic compound such as 4-nitrophenol, 2,4-dinitrophenol, 2,4,5-trichlorophenol, pentachlorophenol and the like; in the presence of a condensing agent such as N,N'dicyclohexylcarbodiimide, 1-(3-dimethylaminopropyl)-3-ethylcarbodiimide and the like.

Active amides of the compounds represented by the general formula [II] can be obtained, for example, by reacting the compounds of the general formula [II] with, following heretofore known methods, an equivalent amount of 1,1'-carbonyldiimidazole or 1,1'-carbonylbis(2-methylimidazole) and the like.

As the use rate of such a reactive derivative of a compound of the general formula [II], normally 0.5 mole to molar excess, preferably 1-1.5 moles, of the derivative per mole of a compound of the general formula [III] is recommended.

The amidation reaction can progress in the absence of base, but presence of base is preferred for smooth progress of the reaction.

In particular, in the reaction using the acid halide or mixed acid anhydride, for example, organic base such as triethylamine, diisopropylethylamine, pyridine and the like, or inorganic base such as sodium hydroxide, potassium hydroxide, sodium carbonate, potassium carbonate, sodium hydrogen-carbonate and the like can be used.

As the use rate of such a base, normally 1 mole to molar excess, preferably 1-4 moles, of the base per mole of the compound of the general formula [III] is recommended. Where the base is liquid, it can be used to serve also as solvent.

Furthermore, in the reactions using any of those reactive derivatives, a basic catalyst such as dimethylaminopyridine can be used as catalyst for promoting the reaction. As the use rate of the catalyst, normally 0.1-5 moles, preferably 0.1-0.5 mole, per mole of the reactive derivative is recommended.

The reactions using such reactive derivatives can normally be conducted at temperatures ranging −50° C.-100° C., and preferably −20° C.-50° C. are recommended.

The time adequate for the reactions using such reactive derivatives is normally 5 minutes-7 days, preferably 30 minutes-24 hours.

Step 1-2: Where $R^4$ is other than hydrogen, compounds represented by the general formula [I'] can be converted to those represented by the general formula [I], by reacting them with the compounds represented by the general formula [IV] in solvent, in the presence of base. More specifically, a compound of the general formula [I'] and base are stirred in a solvent for around 10-60 minutes under cooling with ice, and to the resulting reaction liquid a compound of the general formula [IV] is added and reacted for 1-20 hours.

As the solvent, for example, ether such as diethyl ether, THF, dioxane or the like, DMF, DMSO or the like can be named.

As the base, for example, sodium hydride, potassium hydride and the like can be used, and as the compound of the general formula [IV], methyl iodide, ethyl iodide, methyl p-toluenesulfonate and the like can be named.

Furthermore, as those compounds represented by the general formula [II], reagents available at the market can be used. Besides, they can be prepared following the methods as described in "Synlett", 6, 829 (2000), "Journal of Medicinal Chemistry", 41, 1855 (1998), ibid 44, 703 (2001), "Heterocycles" 35, 1551 (1994), "Synthesis", 609 (1975) and "Journal of Heterocyclic Chemistry, 32, 1563 (1995).

Production Process 2

Those compounds represented by the general formula [III] can be prepared by the following production process 2:

Reaction Scheme 2

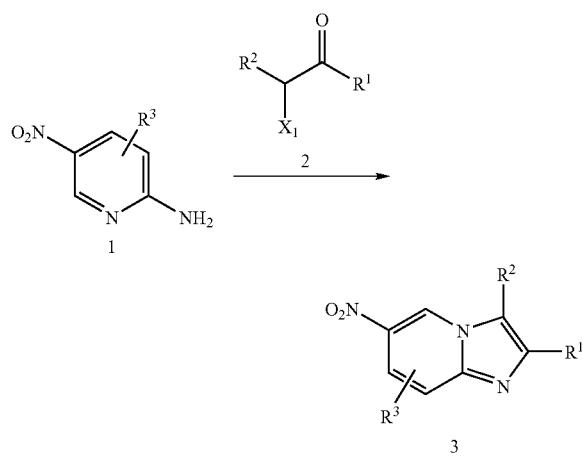

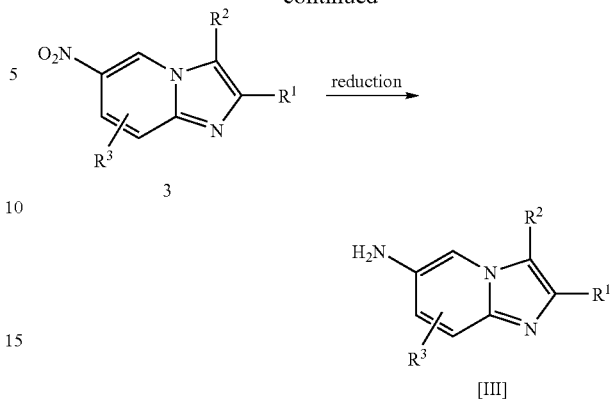

[in which $X^1$, $R^1$, $R^2$ and $R^3$ have the previously given significations].

Step 2-1:

Compound 1 and Compound 2 are heated at 10° C.-200° C., preferably 80° C.-150° C., for 10 minutes-48 hours, preferably 1-24 hours, in optional presence, preferably in the presence, of solvent, to provide Compound 3.

As the solvent, for example, alcohols such as methanol, ethanol, propanol and the like; ethers such as dioxane, THF, diethyl ether and the like; and halogenated hydrocarbon such as methylene chloride, chloroform, carbon tetrachloride and the like can be named.

Use rate of Compound 2 ranges, for example, 1-10 moles, preferably 1-5 moles, per mole of Compound 1.

Step 2-2:

The nitro group of Compound 3 is reduced to provide a compound represented by the general formula [III]. As the reduction method, for example, the one described in WO 02/40019 can be used.

As Compound 1 or Compound 2, reagents available at the market can be used. They can also be prepared by those methods shown in Production Examples.

Production Process 3

Production process 3 is for producing the compounds represented by the general formula [II] wherein W stands for aromatic heterocyclic group.

Reaction scheme 3

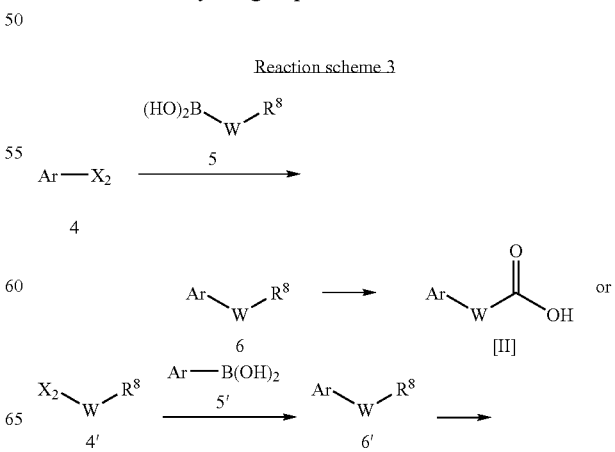

-continued

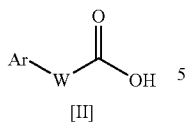

[II]

[in which $R^8$ stands for carboxyl, $COOR^9$ or cyano; $R^9$ standing for $C_{1-6}$ alkyl; $X_2$ is same as $X_1$; and Ar and W have the previously given significations].

That is, a compound of general formula [II] can be prepared by reacting Compound 4 (or Compound 4') with Compound 5 (or Compound 5') in solvent, in the presence of palladium catalyst and base. For this reaction (Suzuki coupling), those methods as described in, for example, Tetrahedron, 58, 9633 (2002) or Chemical Review, 95, 2457 (1995) can be referred to.

When the resulting compound has an ester group ($COOR^9$) or cyano, it can be converted to the compound of the general formula (II) by hydrolyzing the same by the means known per se.

As the palladium catalyst, for example, tetrakis(triphenylphosphine)palladium, palladium acetate, dichlorobis(triphenylphosphine)palladium, [1,1'-bis(diphenylphosphino)ferrocene]dichloropalladium and the like can be named, and as the base, potassium carbonate, sodium carbonate, potassium phosphate and the like can be named.

As the solvent, alcohols such as t-butanol, ethanol and the like; ethers such as THF, 1,2-dimethoxyethane (DME) and the like, aromatic hydrocarbons such as benzene, toluene and the like; or mixed solvent of these are recommended.

As the use rate of Compound 5, for example, 0.9-2.0 moles, preferably 1.0-1.5 moles, per mole of Compound 4 is recommended.

Use rate of the palladium catalyst is, for example, 0.01-0.5 mole per mole of Compound 4, and that of the base, 2.0-10 moles per mole of Compound 4.

Reaction temperature may range, for example, room temperature—150° C., preferably 70° C.-150° C. being recommended, and the reaction time can normally range 1-24 hours.

Furthermore, reagents available at the market can be used as Compound 4 or 4'. On the other hand, Compound 5 or 5' can be prepared by known methods [for example, Journal of Chemical Society, 3129 (1953); Journal or Organic Chemistry, 60, 7508 (1995)].

Production Process 4

This reaction is for production of the compounds in which W is an aliphatic nitrogen-containing heterocyclic group, i.e., the compounds represented by the general formula [I-2].

Reaction scheme 4

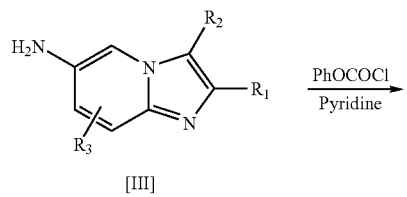

[III]

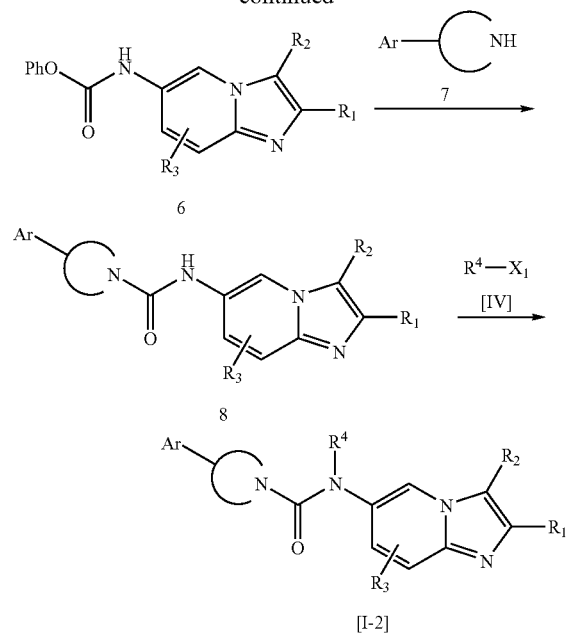

[I-2]

[in which Ph stands for phenyl, and $R^1$, $R^2$, R, $R^4$, Ar and $X_1$ have the previously given significations; and

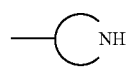

stands for a mono- or bi-cyclic 3 to 8-membered aliphatic nitrogen-containing heterocyclic group].

A compound represented by the general formula [III] is benzoylated in pyridine to provide Compound 6. Successively the Compound 6 is condensed with Compound 7, following the method as described in WO 01/14376. The resulting Compound 8 is reacted with a compound represented by the general formula [IV] following the step 1-2, where necessary, and converted to a compound represented by the general formula [I-2].

As Compound 7, commercially available reagents can be used, or they can be prepared following the methods as described in Journal of Medicinal Chemistry, 43, 2703 (2000); Tetrahedron Letters, 38, 6359 (1997); ibid., 39, 617 (1998) and the like.

In the foregoing Production processes 1-4, when such groups as amino, hydroxyl, carboxyl, oxo, carbonyl and the like which do not participate in the reaction are present in the reactant(s), they can be suitably protected with protective groups of amino, hydroxyl, carboxyl, oxo or carbonyl, respectively, before carrying out a reaction of any of Production processes 1-4. After the reactions, the protective groups can be removed.

As "amino-protective group", aralkyl such as benzyl, p-methoxybenzyl, 3,4-dimethoxybenzyl, o-nitrobenzyl, p-nitrobenzyl, benzhydril, trityl and the like; lower alkanoyl such as formyl, acetyl, propionyl, butyryl, pivaloyl and the like; benzoyl; arylalkanoyl such as phenylacetyl, phenoxyacetyl and the like; lower alkoxycarbonyl such as methoxycarbonyl, ethoxycarbonyl, propyloxycarbonyl, tert-butoxycarbonyl and the like; aralkyloxycarbonyl such as benzyloxycarbonyl, p-nitrobenzyloxycarbonyl, phenethyloxycarbonyl and the like; lower alkylsilyl such as trimethylsilyl, tert-butyldimethylsilyl and the like can be named. In particular, acetyl, pivaloyl, benzoyl, ethoxycarbonyl, tert-butoxycarbonyl are recommended.

As "hydroxyl-protective group", for example, lower alkyl such as methyl, ethyl, propyl, isopropyl, tert-butyl and the like; lower alkylsilyl such as trimethylsilyl, tert-butyldimethylsilyl and the like; lower alkoxymethyl such as methoxymethyl, 2-methoxyethoxymethyl and the like; tetrahydropyranyl; trimethylsilylethoxymethyl; aralkyl such as benzyl, p-methoxybenzyl, 2,3-dimethoxybenzyl, o-nitrobenzyl, p-nitrobenzyl, trityl and the like; and acyl such as formyl, acetyl and the like can be named. In particular, methyl, methoxymethyl, tetrahydropyranyl, trityl, trimethylsilylethoxymethyl, tert-butyldimethylsilyl and acetyl are recommended.

As "carboxyl-protective group", for example, lower alkyl such as methyl, ethyl, propyl, isopropyl, tert-butyl and the like; lower haloalkyl such as 2,2,2-trichloroethyl and the like; lower alkenyl such as 2-propenyl; and aralkyl such as benzyl, p-methoxybenzyl, p-nitrobenzyl, benzhydryl, trityl and the like can be named. In particular, methyl, ethyl, tert-butyl, 2-propenyl, benzyl, p-methoxybenzyl and benzhydryl are recommended.

As "oxo- or carbonyl-protective groups", acetals and ketals such as ethylene ketal, trimethylene ketal, dimethyl ketal and the like can be named.

Means for removing protective groups differ depending on kind of the protective groups and stability of individual compounds represented by the general formula [I]. For example, the removal is conducted following those methods described in literature [cf. *Protective Groups in Organic Synthesis*, T. W. Greene, John Wiley & Sons Co., (1981)] or those analogous thereto, by solvolysis using acid or base, i.e., a method of having, for example, from 0.01 mole to a large molar excess of acid, preferably trifluoroacetic acid, formic acid, hydrochloric acid or the like; or from equimolar to a large molar excess of base, preferably potassium hydroxide, calcium hydroxide or the like, act on the object compound; chemical reduction using metal hydride complex or by catalytic reduction using palladium-on-carbon catalyst or Raney nickel catalyst.

Compounds of the general formula [I] which are obtained by the foregoing processes can be easily isolated and purified by heretofore known separation means. As such means, for example, solvent extraction, recrystallization, column chromatography, liquid chromatography, preparative chromatography and the like can be named.

Compounds of the present invention may have stereoisomers or tautomers such as optical isomers, diastereo isomers, geometrical isomers or the like, depending on the form of their substituents. All of these stereoisomers, tautomers and their mixtures are encompassed by the compounds of the present invention.

Pharmacological Tests of Compounds Represented by the General Formula [I]

Medical utility of compounds of the present invention is verified, for example, by the following pharmacological test examples.

PHARMACOLOGICAL TEST EXAMPLE 1

MCH Binding Inhibition Test

A human MCH-1R encoding cDNA sequence [FEBS Letters, 398, 253 (1996); Biochimica et Biophisica Acta, 1401, 216 (1998)] was cloned to plasmid vector pEF/mic/cyto (Invitrogen Corporation). The obtained expression vector was transfected to a host cell CHO-K1 (American Type Culture Collection) using lipofectamine plus reagent (Life Technology Inc.) to provide MCH-1R expression cells.

Membrane samples prepared from the MCH-1R expression cells were incubated with each test compound and 50 pM of [$^{125}$I]MCH (NEN Co.), in an assay buffer (50 mM Tris buffer comprising 10 mM magnesium chloride, 2 mM ethylenediamine tetraacetate, 0.01% bacitracin and 0.2% bovine serum albumin; pH 7.4) at 25° C. for an hour, followed by filtration through Glass Filter GF/C (Wattman Co.). After washing the glass filter with 50 mM Tris buffer (pH7.4) comprising 10 mM magnesium chloride, 2 mM ethylenediamine tetraacetate and 0.04% Tween-20, radio activity on the glass filter was measured. Non-specific binding was measured in the presence of 1 µM human MCH and 50% inhibition concentration ($IC_{50}$ value) of each test compound to specific [$^{125}$I] MCH binding was determined. The results were as shown in Table 4.

TABLE 4

| Test Compound | $IC_{50}$(nM) |
| --- | --- |
| Example 2 | 3.1 |
| Example 14 | 2.0 |
| Example 17 | 3.3 |
| Example 18 | 4.3 |
| Example 32 | 9.5 |
| Example 36 | 10.5 |

As above, compounds of the present invention potently inhibited binding of MCH to MCH-1R, and acted as MCH-1R antagonist.

PHARMACOLOGICAL TEST EXAMPLE 2

Antagonism Test to MCH-Induced Feeding Behavior

Ketamine-xylazine anesthetized (74 and 11 mg/kg single intraperitoneal administration) male SD rats (9-12 weeks old) were inserted with chronic guide cannule (26 gauge) into their third ventricle as fixed at a set cerebral location with dental resin. The position of the front end of the guide cannula was set to be 2.2 mm behind the bregma on median line and at a depth of 8 mm from the cranial surface. After two weeks' recovery term, the rats were fed with high fat diet for about 4 hours to satiation. Thereafter a needle (33 gauge) which was connected to a microsyringe was inserted into the guide cannula and through which melanin concentrating hormone (MCH, 5 µg/1 µL/head, as dissolved in artificial liquor cerebrospinalis) was administered into each rat's third ventricle. The compound of Example 17 (10 or 30 mg/kg) as suspended in 0.5% aqueous methylcellulose solution was orally administered to the rats an hour before the MCH administration. The rats were successively fed with high fat diet, and their feed intake during the two hours following the MCH administration was measured.

FIG. 1 shows the feed intake by the high fat diet satiated rats, to which the compound of the present invention had been orally administered and an hour thereafter MCH had been administered intraventricularly, during the two hours following said MCH administration, i.e., shows the rats' feed intake (g) per the two hours, where 1) said Example 17 compound was not administered, 2) Example 17 compound was administered at a rate of 10 mg/kg, and 3) Example 17 compound was administered at a rate of 30 mg/kg.

As demonstrated on FIG. 1, the compound of the present invention dose-dependently inhibited increase in the amount of feed intake induced by the MCH which was administered to the rats' third ventricle. In this test, the feed intake in the case where MCH and artificial liquor cerebrospinalis (aCSF) alone was administered in place of the compound of the present invention was used as the reference.

Thus, because the compounds of the present invention inhibit binding of MCH to the receptor thereof, they are useful as preventing or treating agents of various diseases associated with MCH, such as metabolic disorders, e.g., obesity, diabetes, hormone disorder, hyperlipidemia, gout, fatty liver, hepatitis and cirrhosis; cardiovascular disorders, e.g., stenocardia, acute or congestive heart failure, myocardial infarction, coronary atherosclerosis, hypertension, renal diseases and electrolyte abnormality; central nervous system or peripheral nervous system disorders e.g., bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence and alcoholism; reproductive disorders, e.g., infertility, preterm labor and sexual dysfunction; digestive disorders; respiratory disorders; cancer or pigmentation; in particular, as those of obesity.

Pharmaceutical Compositions Containing the Compounds Represented by the General Formula [I]

Those compounds of the present invention can be administered orally or parenterally, and when formulated into preparation forms adapted for administration, can provide preventing or treating agents for metabolic disorders such as obesity, diabetes, hormone disorder, hyperlipidemia, gout, fatty liver, hepatitis and cirrhosis; cardiovascular disorders, such as stenocardia, acute or congestive heart failure, myocardial infarction, coronary atherosclerosis, hypertension, renal diseases and electrolyte abnormality; central nervous system or peripheral nervous system disorders such as bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence and alcoholism; reproductive disorders such as infertility, preterm labor and sexual dysfunction; digestive disorders; respiratory disorders; cancer or pigmentation. In particular, they are useful as preventing or treating agents for obesity.

In the occasions of clinical use of the compounds of the present invention, the compounds may be formulated into various forms of preparations with addition of pharmaceutically acceptable carriers according to the mode of administration, and thereafter administered. As carriers in such occasions, various additives heretofore known in the field of medical preparations can be used, examples of which include gelatine, lactose, sucrose, titanium dioxide, starch, crystalline cellulose, hydroxypropylmethyl cellulose, carboxymethyl cellulose, corn starch, microcrystalline wax, white petrolatum, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, light silicic anhydride, talc, vegetable oil, benzyl alcohol, gum arabic, propylene glycol, polyalkylene glycol, cyclodextrin or hydroxypropylcyclodextrin and the like.

As the preparation forms formulated as mixtures of these carriers and the compounds of the present invention, for example, solid preparations such as tablet, capsule, granule, powder or suppository; and liquid preparations such as syrup, elixir, or injection and the like can be named, which can be prepared following heretofore known methods in the field of medical preparations. Furthermore, liquid preparations may take such a form as to be dissolved or suspended in water or in other suitable medium immediately before use. Particularly, injections can be dissolved or suspended in physiological saline solution or glucose solution where necessary, and buffer or preservative may further be added thereto.

Those preparations can contain the compounds of the present invention at a rate of 1.0-100% by weight, preferably 1.0-60% by weight, to the whole of individual pharmaceutical preparation; and 0-99.0% by weight, preferably 40-99.0% by weight, of pharmaceutically acceptable carrier. These preparations may also contain therapeutically active other compound(s), for example, treating agents for diabetes, hyperlipidermia hypertension, obesity and the like.

In case of using the compounds of the present invention as preventing or treating agents of said diseases or sicknesses, their dosages and administration frequency differ depending on sex, age, body weight and seriousness of symptoms of individual patients and the kind and scope of intended therapeutic effect. Whereas, generally for oral administration, it is preferred to administer 0.001-10 mg, preferably 0.01-2 mg, per kilogram of adult patient per day as a single dose or several divided doses. Depending on symptoms, preventive administration is permissible.

Combination Therapy

The compounds of the present invention can be used in combination with drugs effective for hypertension, obesity-associated hypertension, hypertension-associated diseases, cardiac hypertrophy, left ventricular hypertrophy, metabolic disorder, obesity, obesity-associated diseases and the like (hereafter referred to as "drug for combined use"). Such drugs can be administered simultaneously, separately or in succession, for prevention or treatment of above-named diseases. When a compound of the present invention is used simultaneously with one, two or more of drugs for combined use, they may be formulated into a medical preparation suited for single administration form. Whereas, for occasions of combination therapy, a composition containing the compound of the present invention and drug(s) for combined use may be administered to the object of medication in different packages, either simultaneously, separately or successively. They may be administered at time interval(s).

Dose(s) of drug(s) for combined use are determinable following clinically adopted dose(s), which can be suitably selected according to individual object of medication, administration route, specific disease, combination of drugs, and the like. Form of administering drug(s) for combined use is not critical but it is sufficient that the compound of the present invention is combined with selected drug(s) for combined use at the time of administration. As administration forms, for example, 1) administration of single preparation obtained by simultaneously formulating a compound of the present invention and drug(s) for combined use, 2) simultaneous administration of two kinds of preparations obtained by separately formulating a compound of the present invention and drug(s) for combined use, via a same administration route, 3) administration at a certain time interval, via a same administration route, of two kinds of preparations obtained by separately formulating a compound of the present invention and drug(s) for combined use, 4) simultaneous administration of two kinds of preparations obtained by separately formulating a compound of the present invention and drug(s) for combined use, via different administration routes, and 5) administration of two kinds preparations obtained by separately formulating the compound of the present invention and drug(s) for combined use, via different administration routes, at a certain time interval (e.g., administration by the order of the compound of the present invention and then the drug(s) for combined use, or by the reversed order) can be adopted. The blend ratio of a compound of the present invention and drug(s) for combined use can be suitably selected, according to individual object of medication, administration route, disease and the like.

As drugs for combined use which can be used in the present invention, for example, "diabetes treating agent", "hyperlipidemia treating agent", hypertension treating agent", "obesity treating agent" and the like can be named. Two or more of such drugs for combined use may be combined at an adequate ratio and used.

As "diabetes treating agent", for example, 1) PPAR γ agonists such as glitazones [e.g., ciglitazone, darglitazone, englitazone, isaglitazone (MCC-555) and the like], pioglitazone, rosiglitazone, troglitazone, BRL49653, CLX-0921, 5-BTZD, GW-0207, LG-100641, LY-300512 and the like; 2) biganides such as metformin, buformin, phenformin and the like; 3) protein tyrosine phosphatase-1B inhibitor; 4) sulfonylureas such as acetohexamide, chloropropamide, diabinese, glibenclamide, glipizide, glyburide, glimepiride, gliclazide, glipentide, gliquidone, glisolamide, tolazamide, tolbutamide and the like; 5) meglitinides such as repaglinide, nateglinide and the like; 6) a-glucosidohydroxylase inhibitors such as acarbose, adiposine, camiglibose, emiglitate, miglitol, voglibose, pradimicin-Q, salbostatin, CKD-711, MDL-25,673, MDL-73,945, MOR14 and the like; 7) α-amylase inhibitors such as tendamistat, trestatin, A1 3688 and the like; 8) insulin secretion promoters such as linogliride, A-4166 and the like; 9) fatty acid oxidation repressors such as clomoxir, etomoxir and the like; 10) A2 antagonists such as midaglizole, isaglidole, deriglidole, idazoxan, earoxan, fluparoxan and the like; 11) insulin or insulin mimetics such as biota, LP-100, novarapid, insulin detemir, insulin lispro, insulin glargine, insulin zinc, Lys-Pro-insulin, GLP-1 (73-7), GLP 1 amide (7-36) and the like; 12) non-thiazolidindione such as JT-501, farglitazar and the like; and 13) PPARα/γ dual agonists such as MK-0767, CLX-0940, GW-1536, GW-1929, GW-2433, KRP-297, L-796449, LR-90 and SB219994 and the like; can be named.

As "hyperlipidermia treating agent", for example, 1) cholic acid absorbefacients such as colestrylamine, colesevelem, colestipol, dialkylaminoalkyl derivatives of crossdextran, Colestid™, LoCholest™, Questran™ and the like; 2) HMG-CoA reductase inhibitors such as atorvastatin, itavastatin, fluvastatin, lovastatin, pravastatin, rivastatin, rosuvastatin, simvastatin, ZD-4522 and the like; 3) HMG-CoA synthesis inhibitors; 4) cholesterol absorption inhibitors such as snatol ester, β-sitosterol, sterol gluoside, ezetimibe and the like; 5) acyl coenzyme A cholesterol acyl transferase inhibitors such as avasimibe, eflucimibe, KY-505, SMP-709 and the like; 6) CETP inhibitors such as JTT 705, torcetrapib, CP532632, BAY-63-2149, SC-591, SC-795 and the like; 7) squalene synthesis inhibitors; 8) antioxidants such as probucol; 9) PPARα agonists such as beclofibrate, benzafibrate, ciprofibrate, clofibrate, ethofibrate, fenofibrate, gemcabene, gemfibrozil, GW-7647, BM-170744, LY-518674, fibric acid derivatives [e.g., Atromid™, Lopid™, Tricor™] and the like; 10) FXR receptor antagonists such as GW-4064, SR-103912 and the like; 11) LXR receptor agonists such as GW3965, T9013137, XTCO-179628 and the like; 12) lipoprotein synthesis inhibitors such as niacin; 13) renin-angiotensin inhibitors; 14) microsome-triglyceride transport inhibitors; 15) cholic acid resorption inhibitors such as BARA 1453, SC435, PHA384640, S-435, AZD7706 and the like; 16) PPAR δ agonists such as GW501516, GW590735 and the like; 17) triglyceride synthesis inhibitors; 18) MTTP inhibitors such as LAB687, CP346086 and the like; 19) low density lipoprotein receptor inducer; 20) squalene epoxidase inhibitors; 21) thrombocyte agglutination inhibitors; and 22) 5-lipoxygenase-activating protein inhibitors such as MK-591 and the like; can be named.

As "hypertension treating agents", for example, 1) diuretic such as thiazide-type diuretic, e.g., chlorothialidon, chlorothiazide, dichlorophenamide, hydrofluorothiazide, indapamide, hydrochlorothiazide and the like; loop-type diuretic, e.g., bumetanide, ethacrynic acid, furosemide, torsemide and the like; sodium-type diuretic such as amiloride, triamterene and the like; and aldosterone antagonist-type diuretic, e.g., spironolactone, epirenone and the like; 2) β-adrenaline blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, timolol and the like; 3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, verapamil and the like; 4) angiotensin alteration enzyme inhibitors such as benazepril, captopril, cilazapril, delapril, enalapril, fosinopril, imidapril, losinopril, moexipril, quinapril, quinaprilat, ramipril, perindopril, perindropril, quanipril, spirapril, tenocapril, trandolapril, zofenopril and the like; 5) neutral endopeptidase inhibitors such as omapatrilat, cadoxatril, ecadotril, fosidotril, sampatrilat, AVE 7688, ER 4030 and the like; 6) endothelin antagonists such as tezosentan, A308165, YM62899 and the like; 7) vasodilators such as hydrazine, clonidine, minoxidil, nicotinyl alcohol and the like; 8) angiotension II antagonists such as candesartan, eprosartan, irbesartan, losartan, pratosartan, tasosartan, telmisartan, valsartan, EXP-3137, FI6828K, RNH$_{6270}$ and the like; 9) α/β adrenaline blockers such as nipradilol, arotinolol, amosulalol and the like; 10) α1 blockers such as terazosin, urapidil, prazosin, bunazosin, trimazosin, doxazosin, naftopidil, indoramin, WHIP164, XEN010 and the like; 11) α2 agonists such as lofexidine, tiamenidine, moxonidine, rilmenidine, guanobenz and the like; and 12) aldosteron inhibitors can be named.

As "anti-obesity agents", for example, 1) 5HT (serotonin) transporter inhibitors such as paroxetine, fluoxetine, fenfluramine, fluvoxamine, sertraline, imipramine and the like; 2) norepinephrine transporter inhibitors such as GW320659, desipramine, talsupram, nomifensine and the like; 3) cannabinoid 1 receptor 1(CB-1) antagonist/inverse agonist such as rimonabant (Sanofi Synthelabo), SR-147778 (Sanofi Synthelabo), BAY-65-2520 (Bayer), SLV-319 (Sorbay) and those compounds disclosed in U.S. Pat. Nos. 5,532,237, 4,973,587, 5,013,837, 5,081,122, 5,112,820, 5,292,736, 5,624,941, 6,028,084, WO96/33159, WO98/33765, WO98/43636, WO98/43635, WO01/09120, WO01/96330, WO98/31227, WO98/41519, WO98/37061, WO00/10967, WO00/10968, WO97/29079, WO99/02499, WO01/58869, WO02/076949, WO01/64632, WO01/64633, WO01/64634, WO03/006007, WO03/007887 and EP-658546, and the like; 4) ghrelin antagonists such as those compounds disclosed in, e.g., WO01/87355 and WO02/08250; 5) histamine (H3) antagonist/inverse agonist such as thioperamide, 3-(1H imidazol-4-yl) propyl N-(pentenyl) carbonate, clobenpropit, iodophenpropit, imoproxifen, GT2395, A331440, compounds disclosed in WO02/15905, 0-[3-(1H-imidazo-4-yl)propanol] carbamate, piperazin-containing H3 receptor antagonist (Lazewska, D. et al., Pharmazie, 56:927-32 (2001), benzophenone derivatives (Sasse, A. et al., Arch. Pharm. (Weinheim) 334:45-52 (2001)), substituted N-phenylcarbamate (Reidemeister, S. et al., Pharmazie, 55:83-6(2000)), proxyphene derivatives (Sasse, A. et al., J. Med. Chem., 43:3335-43(2000)) and the like; 6) MCH-1R antagonists such as T-226296(Takeda), SNP-7941(Synaptic) and other compounds disclosed in WO01/82925, WO01/87834, WO02/051809, WO02/06245, WO02/076929, WO02/076947, WO02/04433, WO02/51809, WO02/083134, WO02/094799, WO03/004027 and JP2001-226269A, and the like; 7) MCH-2R agonist/antagonists; 8) NPY1 antagonists such as 3-chloro-5-(1-(6-[2-(5-ethyl-4-methylthiazol-2-yl)-ethyl]-4-morpholinyl-4-yl-pyridin-2-ylamino)ethyl)phenyl] carbamic acid isopropyl ester, BIBP3226, BIB03304, LY-357897, CP-671906, GI-264879, and other compounds disclosed in U.S. Pat. No. 6,001,836, WO96/14307, WO01/23387, WO99/51600, WO01/85690, WO01/85098, WO01/85173 and WO01/89528, and the like; 9) NPY5 antagonists such as 152804, GW-569180A, GW-594884A, GW-587081X, GW-548118X, FR235,208, FR226928, FR240662, FR252384, 1229U91, GI-264879A, CGP71683A, LY-377897, LY366377, PD-160170, SR-120562A, SR-120819A, JCF-104, H409/22, and other compounds disclosed in U.S. Pat. Nos. 6,140,354, 6,191,160, 6,258,837, 6,313,298, 6,337,332, 6,329,395, 340,683, 6,326, 375, 6,329,395, 6,337,332, 6,335,345, EP-01010691, EP-01044970, WO97/19682, WO97/20820, WO97/20821, WO97/20822, WO97/20823, WO98/27063, WO00/107409, WO00/185714, WO00/185730, WO00/64880, WO00/68197, WO0/69849, WO01/09120, WO01/14376, WO01/85714, WO1/85730, WO01/07409, WO01/02379, WO01/02379, WO01/23388, WO01/23389, WO01/44201, WO01/62737, WO01/62738, WO01/09120, WO02/20488, WO02/22592, WO02/48152, WO02/49648, WO02/094789 and Norman et al., J. Med. Chem. 43:4288-4312 (2000), and the like; 10) leptins such as human recombinant leptin (PEG-OB, Hoffman La Ròche), recombinant methionyl-leptin (Amgen) and the like; 11) leptin derivatives such as those compounds which are disclosed in U.S. Pat. Nos. 5,552,524, 5,552,523, 5,552,522, 5,521,283, WO96/23513, WO96/23514, WO96/23515, WO96/23516, WO96/23517, WO96/23518, WO96/23519 and WO96/23520, and the like; 12) opioid antagonists such as Nalmefene (registered trademark to Revex), 3-methoxynaltrexone, naloxone, naltrexone, compounds disclosed in WO00/21509 and the like; 13) orexin antagonists such as SB-334867A and other compounds disclosed in WO01/96302, WO01/68609, WO02/51232, WO02/51838, WO03/023561, and the like; 14) bombesin receptor subtype 3 agonist; 15) cholecystokinin A (CCK-A) agonists such as AR-R15849, GI-181771, JMV-180, A-71378, A-71623, SR-146131, other compounds disclosed in U.S. Pat. No. 5739106, and the like; 16) CNTF (ciliary neurotrophic factors) such as GI-181771 (Glaxo-SmithKline), SR146131 (Sanofi Synthelabo), butabindide, PD170,292, PD149164 (Pfizer) and the like; 17) CNTF derivatives such as axokine (Regeneron), other compounds which are disclosed in WO94/09134, WO98/22128 and WO99/43813, and the like; 18) growth hormone secretion receptor agonists such as NN 703, hexarelin, MK-0677, SM-130686, CP-424,391, L-692, 429, L-163,255, other compounds disclosed in U.S. Pat. No. 6,358,951, U.S. Patent Application Nos. 2002/049196 and 2002/022637, WO01/56592 and WO02/32888, and the like; 19) serotonin receptor 2C agonists such as BVT933, DPCA37215, IK264, PNU22394, WAY161503, R-1065, YM348, other compounds disclosed in U.S. Pat. No. 3,914, 250, WO02/36596, WO02/48124, WO02/10169, WO01/66548, WO02/44152, WO02/51844, WO02/40456 and WO02/40457, and the like; 20) melanocortin 3 receptor agonist; 21) melanocortin 4 receptor agonists such as CHIR86036 (Chiron), ME-10142, ME-10145 (Melacure), other compounds disclosed in WO99/64002, WO00/74679, WO01/991752, WO01/74844, WO01/70708, WO01/70337, WO01/91752, WO02/059095, WO02/059107, WO02/059108, WO02/059117, WO02/12166, WO02/11715, WO02/12178, WO02/15909, WO02/068387, WO02/068388, WO02/067869, WO03/007949 and WO03/009847, and the like; 22) monoamine resorption inhibitors such as Sibutramine (registered trademark to Meridia/Reductil) and salts thereof, other derivatives disclosed in U.S. Pat. Nos. 4,746,680, 4,806,570, 5,436,272, U.S. Patent Application No. 2002/0006964, WO01/27068 and WO01/62341, and the like; 23) serotonin re-introjection inhibitors such as dexfenfluramine, fluoxetine, other compounds disclosed in U.S. Pat. No. 6,365,633, WO01/27060 and WO01/162341, and the like; 24) glucagon-like peptide 1 agonist; 25) Topiramate (registered trademark to Topimax); 26) phytopharm compound 57 (e.g., CP644,673); 27)acetyl CoA carboxylase 2 (ACC2) inhibitor; 28) β-adrenalin receptor 3 agonists such as AD9677/TAK677(Dainippon Pharmaceutical/Takeda Pharmaceutical) CL-316,243, SB418790, BRL-37344, L-796568, BMS-196085, BRL-35135A, CGP12177A, BTA-243, W427353, Trecadrine, ZenecaD7114, SR59119A, other compounds disclosed in U.S. Pat. Nos. 5,705,515, 5,451,677, WO01/74782 and WO02/32897, and the like; 29) diacylglycerolacyl transferase 1 inhibitor; 30) diacylglycerolacyl transferase 2 inhibitor; 31) fatty acid synthesis inhibitors such as Cerulenin, C75 and the like; 32) phosphodiesterase inhibitors such as theofylline, pentoxyfylline, zaprinast, sildenafil, aminone, milrinone, cilostamide, rolipram, cilomilast and the like; 32) thyroid hormone β agonists such as KB-2611 (KaroBio BMS), other compounds disclosed in WO02/15845 and JP2000-256190A, and the like; 33) phytanic acid such as phytanic acid, 4-[(E)-2-(5,6,7,8-tetrahydro-5,5,8,8-tetramethyl-2-naphthalenyl)-1-propenyl] benzoic acid (TTNPB), retinoic acid, other compounds disclosed in WO99/00123, and the like; 34) acyl estrogens such as oleoylestrone, compounds disclosed in del Mar-Grasa, M. et al., Obesity Reseach, 9: 202-9 (2001); 35) glucocorticoid antagonist; 36) 11-β hydroxysteroid dehydrognase 1-type inhibitors such as BVT 3498, BVT 2733, other compounds disclosed in WO01/90091, WO 01/90090 and WO01/90092, and the like; 37) stearyl-CoA desaturase 1 inhibitors; 38) dipeptidyl peptidase IV inhibitors such as isoleucine thiazolidide, valine pyrrolidide, NVP-DPP728, AF237, P93/01, TSL225, TMC-2A/2B/2C, FE999011, P9310/K364, VIP0177, SDZ274-444, other compounds disclosed in WO03/004498, WO03/004496, EP1258476, WO02/083128, WO02/062764, WO03/000250, WO03/002530, WO03/002531, WO03/002553, WO03/002593, WO03/000180 and WO03/000181, and the like; 39) lipase inhibitors such as Tetrahydro lipstatin (registered trademark to Orlistat/Xenical), Triton WR 1339, RHC 80267, lipstatin, tea saponin, diethylumbelliferyl phosphate, FL-386, WAY-121898, BAY-N-3176, valilactone, esteracin, ebelactone A, ebelectone B, RHC80267, other compounds disclosed in WO01/77094, U.S. Pat. Nos. 4,598,089, 4,452, 813, 5,512,565, 5,391,571, 5,602,151, 4,405,644, 4,189,438 and U.S. Pat. No. 4,242,453, and the like; 39) fatty acid transporter inhibitors; 40) dicarboxylate transporter inhibitors; 41) glucose transporter inhibitors; 42) phosphate transporter inhibitors; and the like can be named.

Those combination drugs are obtained by concurrent use of a compound of the present invention with one, two, or more of above drugs for combined use. Furthermore, said combination drugs are useful for prevention or therapy of metabolic disorders, when combined with one, two or more drugs selected from the group consisting of diabetes-treating agents and hyperlipidemia-treating agents. Combinations containing, in particular, hypertension-treating agent and antiobesity agent are useful for prevention or therapy of metabolic disorders with synergistic effect, when diabetes-treating agent(s) and/or hyperlipidemia-treating agent(s) are added thereto.

BRIEF EXPLANATION OF DRAWING

To rats satiated with high fat diet, compounds of the present invention were orally administered, and an hour after the administration, MCH was intraventricularly administered. The rats' feed intakes during the following two hours are shown in FIG. 1.

BEST MODE FOR CARRYING OUT THE INVENTION

Figure 1:
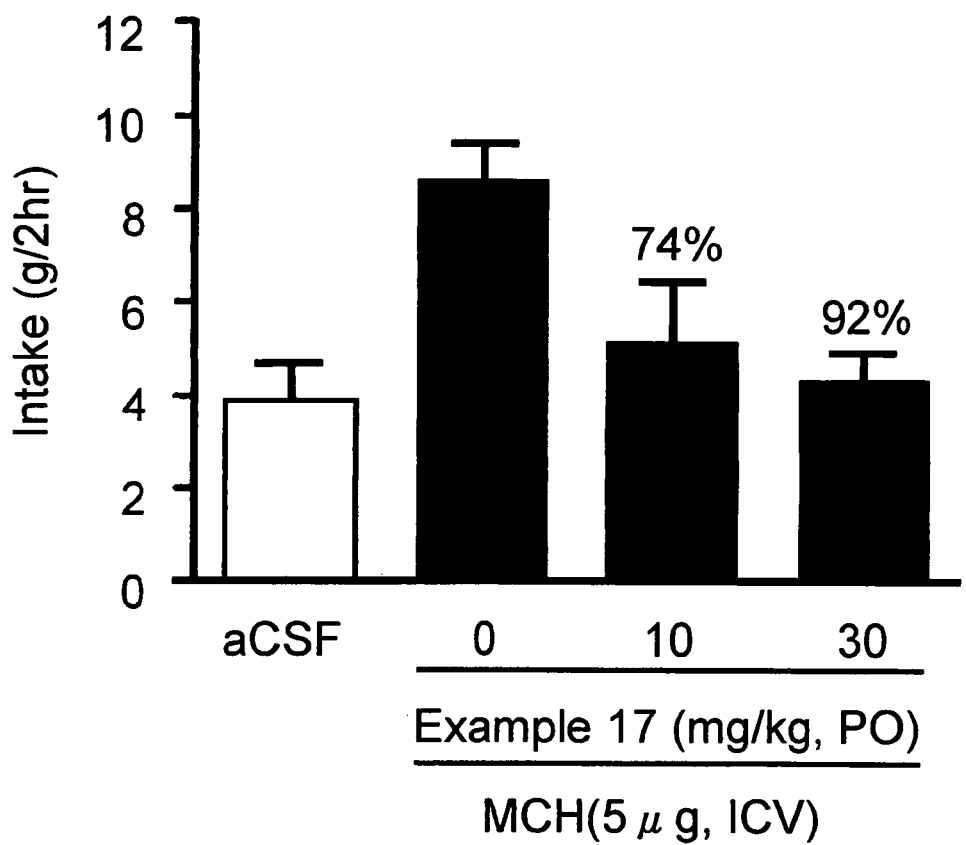

Hereinafter the present invention is explained in detail referring to working Examples, it being understood that the invention is in no sense limited by said Examples. As the silica gel for the columns, Wakogel™ C-300 (Wako Pure Chemical Industries Ltd.) and that for reversed phase columns YMC-GEL™ ProC18 (K.K. YMC) were used. Mass spectra were measured with Quattro II (Micro Mass Co.).

PRODUCTION EXAMPLE 1

2-Isopropyl-6-nitroimidazo[1,2-a]pyridine hydrobromide (1) Into a methanol solution (70 ml) containing 3-methyl-2-butanone (7.2 g), bromine (4.3 ml) was added under cooling with ice, and stirred at 5-10° C. for an hour. To the reaction liquid 40 ml of water was added, followed by stirring for a day and night at room temperature. The reaction liquid was neutralized by addition of 1N aqueous potassium carbonate solution, and extracted with diethyl ether. The organic layer was washed with water and saturated brine and dried over anhydrous sodium sulfate. Concentrating the organic layer under reduced pressure, crude 1-bromo-3-methyl-2-butanone (9.0 g) was obtained.

(2) An ethanol suspension (50 ml) containing the compound (9.0 g) as obtained in above (1) and 2-amino-5-nitropyridine (5.5 g) was stirred for 10 hours at 90° C., and the precipitated solid was recovered by filtration and washed with ethanol to provide the title compound as white solid.

1H-NMR (400 MHz, DMSO-d6, δppm): 1.33 (6H, d, J=7.2 Hz), 3.20-3.28 (1H, m), 7.95 (1H, d, J=9.6 Hz), 8.42 (1H, d, J=9.6 Hz), 10.03 (1H, s)

PRODUCTION EXAMPLE 2

6-Nitro-2-propylimidazo[1,2-a]pyridine hydrobromide

Operations similar to Production Example 1-(1) were conducted using 2-pentanone in place of 3-methyl-2-butanone, and successively those of Production Example 1-(2) were conducted using 2-amino-5-nitropyridine, to provide the title compound as white solid.

1H-NMR (400 MHz, DMSO-d6, δppm): 0.95 (3H, t, J=7.2 Hz), 1.65-1.80 (2H, m), 2.82 (2H, t, J=7.2 Hz), 7.95 (1H, d, J=9.6 Hz), 8.37 (1H, d, J=9.6 Hz), 10.05 (1H, s)

PRODUCTION EXAMPLE 3

2-Tertiary butyl-6-nitroimidazo[1,2-a]pyridine

Operations similar to Production Example 1-(2) were conducted using 1-bromopinacolone and 2-amino-5-nitropyridine. The solid whereupon obtained was suspended in ethyl acetate, and washed with saturated aqueous sodium hydrogencarbonate solution to provide the title compound as yellow solid.

1H-NMR (400 MHz, DMSO-d6, δppm): 1.40 (9H, s), 7.91 (1H, d, J=10.3 Hz), 8.15 (1H, s), 8.29-8.30 (1H, m), 9.94 (1H, s)

PRODUCTION EXAMPLE 4

3-Methyl-6-nitroimidazo[1,2-a]pyridine

Operations similar to Production Example 1-(2) were conducted using 2-bromopropionaldehyde and 2-amino-5-nitropyridine. The solid whereupon obtained was suspended in ethyl acetate, and washed with saturated aqueous sodium hydrogencarbonate solution to provide the title compound as yellow solid.

1H-NMR (400 MHz, CDCl3, δppm): 2.59 (3H, s), 7.58 (1H, s), 7.65 (1H, d, J=10.0 Hz), 7.91 (1H, dd, J=10.0, 2.0 Hz), 9.02 (1H, d, J=2.0 Hz)

PRODUCTION EXAMPLE 5

2,3-Dimethyl-6-nitroimidazo[1,2-a]pyridine

Operations similar to Production Example 1-(2) were conducted using 3-bromo-2-butanone and 2-amino-5-nitropyridine. The solid whereupon obtained was suspended in ethyl acetate, and washed with saturated aqueous sodium hydrogencarbonate. After concentration under reduced pressure, the residue was recrystallized from ethanol to provide the title compound as yellow crystals.

1H-NMR (400 MHz, CDCl3, δppm): 2.47 (3H, s), 2.50 (3H, s), 7.53 (1H, d, J=9.6 Hz), 7.87 (1H, dd, J=9.6, 2.0 Hz), 8.93 (1H, d, J2.0 Hz)

PRODUCTION EXAMPLE 6

2-Cyclopropyl-6-nitroimidazo[1,2-a]pyridine hydrobromide

Operations similar to Production Example 1-(1) were conducted using cyclopropyl methyl ketone in place of 3-methyl-2-butanone, and successively those of Production 1-(2) were conducted using 2-amino-5-nitropyridine, to provide the title compound as white solid.

1H-NMR (400 MHz, DMSO-d6, δppm): 0.94-0.98 (2H, m), 1.10-1.16 (2H, m), 2.20-2.27 (1H, m), 7.85 (1H, d, J=9.6 Hz), 8.28 (1H, dd, J=9.6, 2.0 Hz), 9.95 (1H, s)

PRODUCTION EXAMPLE 7

2-Cyclopropyl-3-methyl-6-nitroimidazo[1,2-a]pyridine

Operations similar to Production Example 1-(1) were conducted using 1-cyclopropyl-1-propanone, and successively those of Production 1-(2) were conducted using 2-amino-5-nitropyridine. The solid whereupon obtained was suspended in ethyl acetate, washed with saturated aqueous sodium hydrogencarbonate solution and purified by silica gel column chromatography (hexane/ethyl acetate=4/1) to provide the title compounds as yellow crystals.

1H-NMR (400 MHz, CDCl3, δppm): 1.01-1.12 (4H, m), 1.95-2.04 (1H, m), 2.58 (3H, s), 7.49 (1H, d, J=9.6 Hz), 7.85 (1H, dd, J=9.6, 2.0 Hz), 8.90 (1J, d, J=2.0 Hz)

PRODUCTION EXAMPLE 8

Ethyl 6-nitroimidazo[1,2-a]pyridine-2-carboxylate

Operations similar to Production Example 1-(2) were conducted using ethyl bromopyruvate and 2-amino-5-nitropyridine. The solid whereupon obtained was suspended in ethyl acetate, and washed with saturated aqueous sodium hydrogencarbonate to provide the title compound as brown solid.

1H-NMR (400 MHz, CDCl3, δppm): 1.45 (3H, t, J=7.2 Hz), 4.48 (2H, q, J=7.2 Hz), 7.77 (1H, d, J=9.6 Hz), 8.01 (1H, dd, J=9.6, 2.0 Hz), 8.35 (1H, s), 9.27 (1H, d, J=2.0 Hz)

PRODUCTION EXAMPLE 9

Methyl 3-methyl-6-nitroimidazo[1,2-a]pyridine-2-carboxylate

Operations similar to Production Example 1-(2) were conducted using methyl 3-bromo-2-oxobutanoate and 2-amino-5-nitropyridine. The resulting solid was suspended in ethyl acetate, washed with saturated aqueous sodium hydrogencarbonate solution and purified by silica gel column chromatography (hexane/ethyl acetate=2/1) to provide the title compound as yellow crystals.

1H-NMR (400 MHz, CDCl3, δppm): 2.91 (3H, s), 4.01 (3H, s), 7.72 (1H, d, J=9.6 Hz), 7.99 (1H, dd, J=9.6, 2.0 Hz), 9.06 (1H, d, J=2.0 Hz)

PRODUCTION EXAMPLE 10

3-Methyl-6-nitro-2-tetrahydro-3-furanylimidazo[1,2-a]pyridine

Operations similar to Production Example 1-(1) were conducted using 1-tetrahydro-3-furanyl-1-propanone in place of 3-methyl-2-butanone, and successively those of Production Example 1-(2) were conducted using 2-amino-5-nitropyridine. The resulting solid was suspended in ethyl acetate, washed with saturated aqueous sodium hydrogencarbonate solution and purified by silica gel column chromatography (hexane/ethyl acetate=2/1) to provide the title compound as yellow crystals.

1H-NMR (400 MHz, CDCl3, δppm): 2.31-2.38 (2H, m), 2.55 (3H, s), 3.60-3.68 (1H, m), 3.91 (1H, t, J=8.0 Hz), 3.99 (1H, q, J=8.0 Hz), 4.11-4.18 (2H, m), 7.59 (1H, d, J=9.6 Hz), 7.90 (1H, dd, J=9.6, 2.0 Hz), 8.95 (1H, d, J=2.0 Hz)

PRODUCTION EXAMPLE 11

2-Nitro-6,7,8,9-tetrahydropyrido[1,2-a]benzimidazole

Operations similar to Production Example 1-(2) were conducted using 2-chlorocyclohexanone and 2-amino-5-nitropyridine. The resulting solid was suspended in ethyl acetate, washed with saturated aqueous sodium hydrogencarbonate solution and purified by silica gel column chromatography (hexane/ethyl acetate=2/1) to provide the title compound as yellow crystals.

1H-NMR (300 MHz, DMSO, δppm): 1.75-2.00 (4H, m), 2.65-2.80 (2H, m), 2.80-2.95 (2H, m), 7.59 (1H, d, J=9.6 Hz), 7.86 (1H, dd, J=9.6, 2.1 Hz), 9.34 (1H, d, J=2.1 Hz)

PRODUCTION 12

2,2,2-Trifluoro-N-(3-methyl-6-nitroimidazo[1,2-a]pyridin-2-yl)acetamide (1) A pyridine suspension (40 ml) containing 2-amino-5-nitropyridine (4.0 g) and p-toluenesulfonyl chloride (5.7 g) was stirred for a day and night at 100° C. The reaction liquid was poured in water (200 ml), the precipitated solid was recovered by filtration, and successively washed with water and diethyl ether by the order stated. Drying the solid under reduced pressure, 4-methyl-N-(5-nitro-2-pyridinyl)benzenesulfonamide (6.7 g) was obtained.

(2) To a DMF suspension (20 ml) containing the compound (3.0 g) as obtained in above (1) and 2-bromopropionamide (1.9 g), diisopropylethylamine (2.2 ml) was added and stirred for a day and night at 90° C. The reaction liquid was poured into water (200 ml), the precipitated solid was recovered by filtration, and successively washed with water and diethyl ether by the order stated. Then the resulting solid was suspended in a liquid mixture of dichloromethane (60 ml) and trifluoroacetic anhydride (30 ml) and stirred for a day and night at room temperature. After concentration under reduced pressure, ethyl acetate was added to the residue. The organic layer was washed with saturated aqueous sodium hydrogencarbonate solution and saturated brine, and dried over anhydrous sodium sulfate. The organic layer was concentrated under reduced pressure, and the precipitated solid was washed with diethyl ether to provide the title compound (2.2 g) as brown crystals.

1H-NMR (400 MHz, CDCl3, δppm): 2.61 (3H, s), 7.58 (1H, d, J=9.6 Hz), 8.03 (1H, dd, J=9.6, 2.0 Hz), 9.05 (1H, d, J=2.0 Hz), 10.56 (1H, brs)

PRODUCTION EXAMPLE 13

Synthesis of 2,2,2-trifluoro-N-methyl-N-(3-methyl-6-nitroimidazo[1,2-a]pyridin-2-yl)acetamide To a THF solution (50 ml) containing the compound (3.0 g) as obtained in Production Example 12, sodium hydride (60% oil-like, 550 mg) was added under cooling with ice, and stirred for 30 minutes. To the reaction liquid, methyl iodide (1 ml) was added, followed by further 3 hours' stirring at the same temperature. The reaction liquid was poured into water. The liquid mixture was extracted with ethyl acetate, washed with saturated brine and dried over anhydrous sodium sulfate. The organic layer was concentrated under reduced pressure and the residue was purified by silica gel column chromatography (hexane/ethyl acetate=5/1) to provide the title compound (1.7 g) as yellow crystals.
1H-NMR (400 MHz, DMSO-d6, δppm): 2.54 (3H, s), 3.30 (3H, s), 7.74 (1H, d, J=9.6 Hz), 8.01 (1H, dd, J=9.6, 2.0 Hz), 9.47 (1H, d, J=2.0 Hz)

PRODUCTION EXAMPLE 14

4'-(Trifluoromethyl)[1,1'-biphenyl]-4-carboxylic acid

To a mixed solution of ethylene glycol dimethyl ether (400 ml)-2M aqueous sodium carbonate solution (80 ml), 4-bromobenzotrifluoride (5.0 g), 4-carboxyphenylboronic acid (3.9 g) and tetrakistriphenylphosphinepalladium (2.5 g) were added and stirred at 100° C. for a day and night. Concentrating the reaction liquid under reduced pressure, the residue was extracted with 1N aqueous sodium hydroxide solution, and the aqueous layer was neutralized by gradual addition of conc. sulfuric acid. The precipitated solid was recovered by filtration, washed with water and diethyl ether and dried under reduced pressure to provide the title compound (4.2 g) as white solid.
1H-NMR (400 MHz, CDCl3, δppm): 7.70 (2H, d, J=8.0 Hz), 7.72-7.80 (4H, m), 8.16 (2H, d, J=8.0 Hz)
ESI-MS Found: m/z 265.0[M−H]

PRODUCTION EXAMPLE 15

2-Methyl-4'-(trifluoromethyl)[1,1'-biphenyl]-4-carboxylic acid

Production Example 14 was repeated except that 4-(trifluoromethyl)phenylboronic acid and 4-bromo-3-methylbenzenecarboxylic acid were used, to provide the title compound as white solid.
ESI-MS Found: m/z 279[M−H]−

PRODUCTION EXAMPLE 16

3-Fluoro-4'-(trifluoromethyl)[1,1'-biphenyl]-4-carboxylic acid

Production Example 14 was repeated except that 4-(trifluoromethyl)phenylboronic acid and 4-bromo-2-fluorobenzenecarboxylic acid were used, to provide the title compound as white solid.
ESI-MS Found: m/z 283[M−H]−

PRODUCTION EXAMPLE 17

4'-(Methylsulfonyl)[1,1'-biphenyl]-4-carboxylic acid

Production Example 14 was repeated except that 4-carboxyphenylboronic acid and 4-bromophenylmethylsulfone were used, to provide the title compound as white solid.
ESI-MS Found: m/z 275[M−H]−

PRODUCTION EXAMPLE 18

4-(2-pyridyl)benzenecarboxylic acid

Production Example 14 was repeated except that 4-carboxyphenylboronic acid and 2-bromopyridine were used, to provide the title compound as white solid.
ESI-MS Found: m/z 200[M+H]+
ESI-MS Found: m/z 198[M−H]−

PRODUCTION EXAMPLE 19

4-(5-Methyl-2-pyridyl)benzenecarboxylic acid

Repeating the operations of Production Example 14 using 4-(methoxycarbonyl)phenylboronic acid and 2-bromo-5-methylpyridine, methyl 4-(5-methyl-2-pyridyl)benzoate was obtained. Hydrolyzing the same with 5N aqueous sodium hydroxide solution, the title compound was obtained as white solid.
ESI-MS Found: m/z 214[M+H]+

PRODUCTION EXAMPLE 20

4-(5-Chloro-2-pyridyl)benzenecarboxylic acid

Repeating the operations of Production Example 14 using 4-(methoxycarbonyl)phenylboronic acid and 2,5-dichloropyridine, methyl 4-(5-chloro-2-pyridyl)benzoate was obtained. Hydrolyzing the same with 5N aqueous sodium hydroxide solution, the title compound was obtained as white solid.
ESI-MS Found: m/z 234, 236[M+H]+

PRODUCTION EXAMPLE 21

4-(5-Methoxy-2-pyridyl)benzenecarboxylic acid

Repeating the operations of Production Example 14 using 4-(methoxycarbonyl)phenylboronic acid and 2-bromo-5-methoxypyridine, methyl 4-(5-methoxy-2-pyridyl)benzoate was obtained. Hydrolyzing the same with 5N aqueous sodium hydroxide solution, the title compound was obtained as white solid.
ESI-MS Found: m/z 230[M+H]+

PRODUCTION EXAMPLE 22

4-[6-(Difluoromethyl)-3-pyridyl]benzenecarboxylic acid

Operations similar to those of Production Example 14 were conducted using 4-carboxyphenylboronic acid and 5-bromo-2-(difluoromethyl)pyridine, to provide the title compound as white solid.
ESI-MS Found: m/z 248[M−H]−

PRODUCTION EXAMPLE 23

4-[5-(Difluoromethoxy)-2-pyridyl]benzenecarboxylic acid

Operations similar to those of Production Example 14 were conducted using 4-carboxyphenylboronic acid and 2-bromo-5-(difluoromethoxy)pyridine, to provide the title compound as white solid.
ESI-MS Found: m/z 266[M+H]+

PRODUCTION EXAMPLE 24

4-[5-(Trifluoromethyl)-2-pyridyl]benzenecarboxylic acid

Operations similar to those of Production Example 14 were conducted using 4-carboxyphenylboronic acid and 2-bromo-5-trifluoromethyl)pyridyl, to provide the title compound as white solid.

1H-NMR (400 MHz, DMSO-d6, δppm): 8.08 (2H, d, J=8.0 Hz), 8.22-8.37 (4H, m), 9.07 (1H, s)
ESI-MS Found: m/z 268[M+H]+
ESI-MS Found: m/z 266[M−H]−

PRODUCTION EXAMPLE 25

4-[6-(Trifluoromethyl)-3-pyridyl]benzenecarboxylic acid

Operations similar to those of Production Example 14 were conducted using 4-carboxyphenylboronic acid and 5-bromo-2-(trifluoromethyl)pyridyl, to provide the title compound as white solid.
1H-NMR (400 MHz, DMSO-d6, δppm): 7.93 (2H, d, J=8.0 Hz), 8.00 (1H, d, J=8.0 Hz), 8.06 (2H, d, J=8.0 Hz), 8.41 (1H, dd, J=8.0, 2.0 Hz), 9.13 (1H, s)
ESI-MS Found: m/z 268[M+H]+
ESI-MS Found: m/z 266[M−H]−

PRODUCTION EXAMPLE 26

4-(6-Fluoro-3-pyridyl)benzenecarboxylic acid

Operations similar to those of Production Example 14 were conducted using 4-carboxyphenylboronic acid and 5-bromo-2-fluoropyridyl, to provide the title compound as white solid.
ESI-MS Found: m/z 218[M+H]+

PRODUCTION EXAMPLE 27

4-[5-(trifluoromethyl)-2-pyrimidine]benzenecarboxylic acid (1) To an ethanol solution (20 ml) containing N-[3-(dimethylamino)-2-(trifluoromethyl)-2-propenylidene]-N-dimethylammonium chloride (1.1 g) and 4-amidinobenzamide hydrochloride (1.0 g), sodium hydride (60%, oil-like, 400 mg) was added, and stirred for 40 minutes at 90° C. Water was added to the reaction liquid, and the precipitated crystals were recovered by filtration. The crystals were washed with diisopropyl ether and dried under reduced pressure to provide 4-[5-(trifluoromethyl)-2-pyrimidine]benzamide (705 mg) as solid.
(2) The compound (224 mg) as obtained in (1) above was dissolved in 40% aqueous sulfuric acid solution (4 ml)-1,4-dioxane (2 ml), and stirred for 2 days under heating at 85° C., followed by standing to cool off. Thus precipitated crystals were recovered by filtration and washed with water to provide the title compound (205 mg) as white solid.
ESI-MS Found: m/z 269[M+H]+
ESI-MS Found: m/z 267[M−H]−

PRODUCTION EXAMPLE 28

6-(4-Fluorophenyl)nicotinic acid

Operations similar to those of Production Example 14 were conducted using 6-chloronicotinic acid and 4-fluorophenylboronic acid, to provide the title compound as white solid.
1H-NMR (400 MHz, DMSO-d6, δppm): 7.30-7.37 (2H, m), 8.03 (1H, d, J=8.0 Hz), 8.16-8.22 (2H, m), 8.26 (1H, d, J=8.0 Hz), 9.07 (1H, s)
ESI-MS Found: m/z 218[M+H]+

PRODUCTION EXAMPLE 29

5-(4-Fluorophenyl)-2-pyridinecarboxylic acid

Operations similar to those of Production Example 14 were conducted using 5-bromo-2-pyridinecarboxylic acid and 4-fluorophenylboronic acid, to provide the title compound as white solid.
ESI-MS Found: m/z 218[M+H]+

PRODUCTION EXAMPLE 30

2,3'-Dipyridine-6'-carboxylic acid (1) Conducting the operations similar to those of Production Example 14 using 2-iodopyridine and 6-bromo-3-pyridineboronic acid, 6'-bromo-2,3'-dipyridine was obtained.
(2) The compound (330 mg) as obtained in above (1), catalytic amount of [1,1'-bis(diphenylphosphino)ferrocene]dichloropalladium and triethylamine (0.7 ml) were added to a DMF-methanol mixed solution (DMF/methanol; 5/1 ml) and stirred in carbon monoxide atmosphere at 80° C. for a day and night, to provide methyl-2,3'-dipyridine-6'-carboxylate (160 mg). Hydrolyzing this with 5N aqueous sodium hydroxide solution, the title compound (110 mg) was obtained as white solid.
ESI-MS Found: m/z 201[M+H]+

PRODUCTION EXAMPLE 31

5-Chloro-2,3'-dipyridine-6'-carboxylic acid (1) Conducting the operations similar to those of Production Example 14 using 2,5-dichloropyridine (320 mg) and 6-fluoro-3-pyridineboronic acid, 5-chloro-6'-fluoro-2,3'-dipyridine (270 mg) was obtained.
(2) The compound (230 mg) as obtained in above (1) and tetraethylammonium cyanide (230 mg) were added to a DMF solution (2 ml) and stirred for a day and night at 80° C., to provide 5-chloro-2,3'-dipyridine-6-carbonitrile (87 mg).
(3) The compound (87 mg) as obtained in above (2) was dissolved in 40% aqueous sulfuric acid solution (17 ml) and stirred for a day and night at 80° C. to provide the title compound (83 mg) as white solid.
ESI-MS Found: m/z 235, 237[M+H]+

PRODUCTION EXAMPLE 32

5-(4-Fluorophenyl)-2-pyrazinecarboxylic acid (1) Conducting the operations similar to those of Production Example 14 using 2-amino-5-bromopyrazine (2.7 g) and 4-fluorophenylboronic acid (3.4 g), 2-amino-5-(4-fluorophenyl)pyrazine was obtained as white solid.
(2) The compound (2.6 g) as obtained in above (1) and isopentyl nitrite (2.8 mg) were added to bromoform solution (30 ml) and stirred at 100° C. to provide 2-bromo-5-(4-fluorophenyl)pyrazine (1.8 g).
(3) The compound (1.8 g) as obtained in above (2), sodium cyanide (0.4 g) and copper cyanide (0.2 g) were added to DMF solution (30 ml) and stirred at 150° C. to provide 5-(4-fluorophenyl)-2-pyrazinecarbonitrile (1.0 g).
(4) The compound (1.0 g) as obtained in above (3) was added to 40% aqueous sulfuric acid solution and stirred at 80° C. to provide the title compound (1.0 g) as white solid.
ESI-MS Found: m/z 219[M+H]+

PRODUCTION EXAMPLE 33

5-Phenylpyrimidine-2-carboxylic acid

Conducting the operations similar to those of Production Example 14 using 5-bromopyrimidine-2-carboxylic acid and phenylboronic acid, the title compound was obtained as white solid.

1H-NMR (400 MHz, DMSO-d6, δppm): 7.44-7.62 (3H, m), 7.90 (2H, d, J=8.0 Hz), 9.28 (2H, s)

ESI-MS Found: m/z 201[M+H]+

ESI-MS Found: m/z 199[M−H]−

PRODUCTION EXAMPLE 34

5-(4-Fluorophenyl)-2-pyrimidinecarboxylic acid

Conducting the operations similar to those of Production Example 14 using 5-bromopyrimidine-2-carboxylic acid and 4-fluorophenylboronic acid, the title compound was obtained as white solid.

ESI-MS Found: m/z 219[M+H]+

ESI-MS Found: m/z 217[M−H]−

PRODUCTION EXAMPLE 35

5-(6-Fluoropyridin-3-yl)pyrimidine-2-carboxylic acid

Conducting the operations similar to those of Production Example 14 using 5-bromopyrimidine-2-carboxylic acid and 6-fluoro-3-pyridineboronic acid, the title compound was obtained as white solid.

ESI-MS Found: m/z 220[M+H]+

EXAMPLE 1

N-(2-isopropylimidazo[1,2-a]pyridin-6-yl)-4'-(trifluoromethyl)-[1,1'-biphenyl]-4-carboxamide (1) To a methanol solution (20 ml) containing 2-isopropyl-6-nitroimidazo[1,2-a]pyridine hydrobromide (280 mg), 10% palladium-on-carbon (30 mg) was added, and inside the reaction system was substituted with hydrogen, followed by an hour's stirring at room temperature. The reaction liquid was filtered through Celite™. Concentrating the filtrate under reduced pressure, crude 6-amino-2-isopropylimidazo[1,2-a]pyridine hydrobromide (250 mg) was obtained.

(2) The above crude product (250 mg) was dissolved in DMF (10 ml), to which 4'-(trifluoromethyl)[1,1'-biphenyl]-4-carboxylic acid (260 mg), HATU (380 mg) and diisopropylethylamine (0.6 ml) were added and stirred for 2 hours at room temperature. Water was added to the reaction liquid which then was extracted with ethyl acetate. The organic layer was washed with water and saturated brine, and dried over anhydrous sodium sulfate. The organic layer was concentrated under reduced pressure, and the residue was purified on silica gel column chromatography (chloroform/methanol=90/1-50/1) to provide the title compound (150 mg) as white solid.

1H-NMR (400 MHz, CDCl3, δppm): 1.36 (6H, d, J=6.8 Hz), 3.03-3.14 (1H, m), 6.94 (1H, d, J=9.6 Hz), 7.35 (1H, s), 7.47 (1H, d, J=9.6 Hz), 7.66-7.74 (6H, m), 7.97 (2H, d, J=8.0 Hz), 8.03 (1H, brs), 9.20 (1H, s)

EXAMPLE 2

4'-Fluoro-N-(2-isopropylimidazo[1,2-a]pyridin-6-yl)[1,1'-biphenyl]-4-carboxamide Conducting the operations similar to those of Example 1 using 2-isopropyl-6-nitroimidazo[1,2-a]pyridine hydrobromide and 4'-fluoro[1,1'-biphenyl]-4-carboxylic acid, the title compound was obtained as white solid.

1H-NMR (400 MHz, CDCl3, δppm): 1.37 (6H, d, J=6.8 Hz), 3.05-3.15 (1H, m), 6.92 (1H, d, J=9.6 Hz), 7.15 (2H, t, J=8.4 Hz), 7.35 (1H, s), 7.49 (1H, d, J=9.6 Hz), 7.55-7.60 (2H, m), 7.65 (2H, d, J=8.4 Hz), 7.85 (1H, brs), 7.93 (2H, d, J=8.0 Hz), 9.20 (1H, s)

EXAMPLE 3

N-(2,3-dimethylimidazo[1,2-a]pyridin-6-yl)-4'-(trifluoromethyl)[1,1'-biphenyl]-4-carboxamide Conducting the operations similar to those of Example 1 using 2,3-dimethyl-6-nitroimidazo[1,2-a]pyridine and 4'-(trifluoromethyl)-[1,1'-biphenyl]-4-carboxylic acid, the title compound was obtained as white solid.

1H-NMR (400 MHz, CDCl3, δppm): 2.43 (6H, s), 6.93 (1H, d, J=9.6 Hz), 7.46 (1H, d, J=9.6 Hz), 7.66-7.75 (6H, m), 7.95 (1H, brs), 7.98 (2H, d, J=8.4 Hz), 8.95 (1H, s)

EXAMPLE 4

N-(3-methylimidazo[1,2-a]pyridin-6-yl)-4'-(trifluoromethyl)-[1,1'-biphenyl]-4-carboxamide Conducting the operations similar to those of Example 1 using 3-methyl-6-nitroimidazo[1,2-a]pyridine and 4'-(trifluoromethyl)-[1,1'-biphenyl]-4-carboxylic acid, the title compound was obtained as white solid.

1H-NMR (400 MHz, CDCl3, δppm): 2.51 (3H, s), 7.00 (1H, dd, J=9.6, 1.6 Hz), 7.41 (1H, s), 7.50 (1H, d, J=9.6 Hz), 7.70-7.78 (6H, m), 8.01 (2H, d, J=8.0 Hz), 8.38 (1H, brs), 9.05 (1H, s)

EXAMPLE 5

N-(6,7,8,9-tetrahydropyrido[1,2-a]benzimidazol-2-yl)-4'-(trifluoromethyl)[1,1'-biphenyl]-4-carboxamide Conducting the operations similar to those of Example 1 using 2-nitro-6,7,8,9-tetrahydropyrido[1,2-a]benzimidazole and 4'-(trifluoromethyl)[1,1'-biphenyl]-4-carboxylic acid, the title compound was obtained as white solid.

1H-NMR (300 MHz, DMSO-d6, δppm): 10.80-2.00 (4H, m), 2.65-2.85 (4H, m), 7.35-7.55 (2H, m), 7.87 (2H, d, J=8.4 Hz), 7.95 (2H, d, J=8.4 Hz), 8.01 (2H, d, J=8.4 Hz), 8.14 (2H, d, J=8.4 Hz), 8.82 (1H, s), 10.44 (1H, s)

EXAMPLE 6

N-(2-cyclopropyl-3-methylimidazo[1,2-a]pyridin-6-yl)-4'-(trifluoromethyl)[1,1'-biphenyl]-4-carboxamide hydrochloride Operations similar to those of Example 1 were conducted using 2-cyclopropyl-3-methyl-6-nitroimidazo[1,2-a]pyri dine and 4'-(trifluoromethyl)[1,1'-biphenyl]-4-carboxylic acid. The resulting solid was dissolved in ethyl acetate, followed by addition of 4N hydrochloric acid-ethyl acetate solution and concentration under reduced pressure. The title compound was obtained as white solid.

1H-NMR (400 MHz, DMSO-d6, δppm): 1.00-1.07 (2H, m), 1.12-1.18 (2H, m), 2.23-2.33 (1H, m), 2.57 (3H, s), 7.83-7.88 (3H, m), 7.94 (2H, d, J=8.0 Hz), 7.98 (2H, d, J=8.0 Hz), 8.18 (3H, d, J=8.0 Hz), 9.30 (1H, s), 11.00 (1H, s)

EXAMPLE 7

N-(2-cyclopropyl-3-methylimidazo[1,2-a]pyridin-6-yl)-4-[5-(trifluoromethyl)-2-pyridyl]benzamide hydrochloride Operations similar to those of Example 1 were conducted using 2-cyclopropyl-3-methyl-6-nitroimidazo[1,2-a]pyridine and 4-[5-(trifluoromethyl)-2-pyridyl]benzenecarboxylic acid. The resulting solid was dissolved in ethyl acetate, followed by addition of 4N hydrochloric acid-ethyl acetate solution and concentration under reduced pressure. The title compound was obtained as white solid.

1H-NMR (400 MHz, DMSO-d6, δppm): 1.00-1.08 (2H, m), 1.10-1.18 (2H, m), 2.22-2.32 (1H, m), 2.56 (3H, s), 7.87 (1H, d, J=9.6 Hz), 8.19-8.28 (3H, m), 8.32-8.38 (4H, m), 9.08 (1H, s), 9.30 (1H, s), 11.11 (1H, s)

EXAMPLE 8

N-(2-cyclopropyl-3-methylimidazo[1,2-a]pyridin-6-yl)-4-[6-(trifluoromethyl)-3-pyridyl]benzamide hydrochloride Operations similar to those of Example 1 were conducted using 2-cyclopropyl-3-methyl-6-nitroimidazo[1,2-a]pyridine and 4-[6-(trifluoromethyl)-3-pyridyl]benzenecarboxylic acid. The resulting solid was dissolved in ethyl acetate, followed by addition of 4N hydrochloric acid-ethyl acetate solution and concentration under reduced pressure. The title compound was obtained as white solid.

1H-NMR (400 MHz, DMSO-d6, δppm): 1.00-1.08 (2H, m), 1.12-1.18 (2H, m), 2.23-2.34 (1H, m), 2.57 (3H, s), 7.86 (1H, d, J=9.6 Hz), 8.01-8.07 (3H, m), 8.18-8.24 (3H, m), 8.46 (1H, dd, J=8.0, 1.6 Hz), 9.18 (1H, s), 9.31 (1H, s), 11.05 (1H, s)

EXAMPLE 9

N-(2-cyclopropyl-3-methylimidazo[1,2-a]pyridin-6-yl)-4-(6-fluoro-3-pyridyl)benzamide hydrochloride Operations similar to those of Example 1 were conducted using 2-cyclopropyl-3-methyl-6-nitroimidazo[1,2-a]pyridine and 4-(6-fluoro-3-pyridyl)benzenecarboxylic acid. The resulting solid was dissolved in ethyl acetate, followed by addition of 4N hydrochloric acid-ethyl acetate solution and concentration under reduced pressure. The title compound was obtained as white solid.

1H-NMR (400 MHz, DMSO-d6, δppm): 1.00-1.07 (2H, m), 1.12-1.18 (2H, m), 2.23-2.34 (1H, m), 2.57 (3H, s), 7.33 (1H, dd, J=9.6, 2.4 Hz), 7.86 (1H, d, J=9.6 Hz), 7.93 (2H, d, J=8.8 Hz), 8.14-8.22 (3H, m), 8.35-8.43 (1H, m), 8.66 (1H, s), 9.30 (1H, s), 11.00 (1H, s)

EXAMPLE 10

4-(5-Chloro-2-pyridyl)-N-(2-cyclopropyl-3-methylimidazo-[1,2-a]pyridin-6-yl)benzamide Conducting the operations similar to those of Example 1 using 2-cyclopropyl-3-methyl-6-nitroimidazo[1,2-a]pyridine and 4-(5-chloro-2-pyridyl)benzenecarboxylic acid, the title compound was obtained as white solid.

1H-NMR (300 MHz, DMSO-d6, δppm): 0.88-0.90 (4H, m), 2.05-2.06 (1H, m), 2.50 (3H, s), 7.40 (2H, brs), 8.05-8.15 (4H, m), 8.25 (1H, d, J=6.6 Hz), 8.75 (1H, s), 8.88 (1H, s), 10.42 (1H, s)

EXAMPLE 11

N-(2-cyclopropyl-3-methylimidazo[1,2-a]pyridin-6-yl)-5-(4-fluorophenyl)-2-pyrimidinecarboxamide hydrochloride Operations similar to those of Example 1 were conducted using 2-cyclopropyl-3-methyl-6-nitroimidazo[1,2-a]pyridine and 5-(4-fluorophenyl)-2-pyrimidinecarboxylic acid. The resulting solid was dissolved in ethyl acetate, followed by addition of 4N hydrochloric acid-ethyl acetate solution and concentration under reduced pressure. The title compound was obtained as white solid.

1H-NMR (400 MHz, DMSO-d6, δppm): 1.00-1.07 (2H, m), 1.12-1.18 (2H, m), 2.23-2.34 (1H, m), 2.57 (3H, s), 7.40-7.47 (2H, m), 7.86 (1H, d, J=9.6 Hz), 7.97-8.03 (2H, m), 8.31 (1H, dd, J=9.6, 2.0 Hz), 9.33 (1H, s), 9.37 (2H, s), 11.44 (1H, s)

EXAMPLE 12

N-(2-cyclopropyl-3-methylimidazo[1,2-a]pyridin-6-yl)-5-(3-fluorophenyl)-2-pyrimidinecarboxamide hydrochloride Operations similar to those of Example 1 were conducted using 2-cyclopropyl-3-methyl-6-nitroimidazo[1,2-a]pyridine and 5-(3-fluorophenyl)-2-pyrimidinecarboxylic acid. The resulting solid was dissolved in ethyl acetate, followed by addition of 4N hydrochloric acid-ethyl acetate solution and concentration under reduced pressure. The title compound was obtained as white solid.

1H-NMR (400 MHz, DMSO-d6, δppm): 1.00-1.07 (2H, m), 1.12-1.18 (2H, m), 2.23-2.34 (1H, m), 2.58 (3H, s), 7.35-7.41 (1H, m), 7.60-7.66 (1H, m), 7.80 (1H, d, J=9.6 Hz), 7.85-7.90 (2H, m), 8.31 (1H, dd, J=9.6, 1.6 Hz), 9.33 (1H, s), 9.42 (2H, s), 11.46 (1H, s)

EXAMPLE 13

N-(2-cyclopropyl-3-methylimidazo[1,2-a]pyridin-6-yl)-5-(4-fluorophenyl)-2-pyrazinecarboxamide hydrochloride Operations similar to those of Example 1 were conducted using 2-cyclopropyl-3-methyl-6-nitroimidazo[1,2-a]pyridine and 5-(4-fluorophenyl)-2-pyrazinecarboxylic acid. The resulting solid was dissolved in ethyl acetate, followed by addition of 4N hydrochloric acid-ethyl acetate solution and concentration under reduced pressure. The title compound was obtained as white solid.

1H-NMR (400 MHz, DMSO-d6, δppm): 1.00-1.07 (2H, m), 1.12-1.18 (2H, m), 2.23-2.34 (1H, m), 2.57 (3H, s), 7.41 (1H, d, J=8.8 Hz), 7.43 (1H, d, J=8.8 Hz), 7.85 (1H, d, J=9.6 Hz), 8.30-8.38 (3H, m), 9.31 (1H, s), 9.33 (1H, s), 9.37 (1H, s), 11.38 (1H, s)

EXAMPLE 14

N-(2-cyclopropyl-3-methylimidazo[1,2-a]pyridin-6-yl)-5-(4-fluorophenyl)-2-pyridinecarboxamide hydrochloride Operations similar to those of Example 1 were conducted using 2-cyclopropyl-3-methyl-6-nitroimidazo[1,2-a]pyridine and 5-(4-fluorophenyl)-2-pyridinecarboxylic acid. The resulting solid was dissolved in ethyl acetate, followed by addition of 4N hydrochloric acid-ethyl acetate solution and concentration under reduced pressure. The title compound was obtained as white solid.

1H-NMR (400 MHz, DMSO-d6, δppm): 1.00-1.07 (2H, m), 1.12-1.18 (2H, m), 2.23-2.34 (1H, m), 2.57 (3H, s), 7.37 (1H, d, J=8.8 Hz), 7.40 (1H, d, J=8.8 Hz), 7.84-7.94 (3H, m), 8.23 (1H, d, J=8.4 Hz), 8.36 (2H, dd, J=8.0, 2.0 Hz), 9.03 (1H, s), 9.35 (1H, s), 11.36 (1H, s)

EXAMPLE 15

N-(2-cyclopropyl-3-methylimidazo[1,2-a]pyridin-6-yl)-6-(4-fluorophenyl)nicotinamide hydrochloride Operations similar to those of Example 1 were conducted using 2-cyclopropyl-3-methyl-6-nitroimidazo[1,2-a]pyridine and 6-(4-fluorophenyl)nicotinic acid. The resulting solid was dissolved in ethyl acetate, followed by addition of 4N hydrochloric acid-ethyl acetate solution and concentration under reduced pressure. The title compound was obtained as white solid.

1H-NMR (400 MHz, DMSO-d6, δppm): 1.00-1.07 (2H, m), 1.12-1.18 (2H, m), 2.23-2.34 (1H, m), 2.56 (3H, s), 7.34 (1H, d, J=8.8 Hz), 7.36 (1H, d, J=8.8 Hz), 7.87 (1H, d, J=9.6 Hz), 8.16 (1H, d, J=8.4 Hz), 8.20-8.28 (3H, m), 8.53 (1H, dd, J=8.4, 2.0 Hz), 9.27 (1H, d, J=2.0 Hz), 9.29 (1H, s), 11.25 (1H, s)

EXAMPLE 16

N-(3-methyl-2-tetrahydro-3-furanylimidazo[1,2-a]pyridin-6-yl)-4-[5-(trifluoromethyl)-2-pyridyl]benzamide Conducting the operations similar to those of Example 1 using 3-methyl-6-nitro-2-tetrahydro-3-furanylimidazo[1,2-a]pyridine and 4-[5-(trifluoromethyl)-2-pyridyl]benzenecarboxylic acid, the title compound was obtained as white solid.

1H-NMR (400 MHz, CDCl3, δppm): 2.30-2.41 (2H, m), 2.48 (3H, s), 3.58-3.66 (1H, m), 3.90 (1H, t, J=8.0 Hz), 3.98 (1H, q, J=8.0 Hz), 4.10-4.19 (2H, m), 6.97 (1H, dd, J=9.6, 2.0 Hz), 7.54 (1H, d, J=9.6 Hz), 7.90 (1H, d, J=8.0 Hz), 7.95 (1H, brs), 8.02 (3H, d, J=8.0 Hz), 8.18 (2H, d, J=8.0 Hz), 8.96 (1H, brs), 9.00 (1H, s)

EXAMPLE 17

N-(2-cyclopropyl-3-methylimidazo[1,2-a]pyridin-6-yl)-4-(2-pyridyl)benzamide hydrochloride The title compound was obtained as white solid by conducting the operations similar to those of Example 1, using 2-cyclopropyl-3-methyl-6-nitroimidazo[1,2-a]pyridine and 4-(2-pyridyl)benzenecarboxylic acid. The resulting solid was dissolved in ethyl acetate, followed by addition of 4N hydrochloric acid-ethyl acetate solution and concentration under reduced pressure, to provide the title compound as white solid.

1H-NMR (400 MHz, DMSO-d6, δppm): 1.03-1.17 (4H, m), 2.22-2.30 (1H, m), 2.56 (3H, s), 7.61 (1H, t, J=6.0 Hz), 7.86 (1H, dd, J=9.6, 0.8 Hz), 8.14-8.30 (7H, m), 8.77 (1H, d, J=5.2 Hz), 9.31 (1H, s), 11.16 (1H, s)

EXAMPLE 18

N-(2-cyclopropyl-3-methylimidazo[1,2-a]pyridin-6-yl)-3-[4-(trifluoromethyl)phenyl]propanamide Conducting the operations similar to those of Example 1 using 2-cyclopropyl-3-methyl-6-nitroimidazo[1,2-a]pyridine and 3-[4-(trifluoromethyl)phenyl]propionic acid, the title compound was obtained as white solid.

1H-NMR (400 MHz, CDCl3, δppm): 0.93-1.00 (4H, m), 1.92-2.00 (1H, m), 2.47 (3H, s), 2.75 (2H, t, J=7.2 Hz), 3.13 (2H, t, J=7.2 Hz), 6.65 (1H, dd, J=9.6, 2.4 Hz), 7.25 (1H, d, J=9.6 Hz), 7.31 (2H, d, J=8.0 Hz), 7.51 (2H, d, J=8.0 Hz), 7.83 (1H, brs), 8.77 (1H, s)

EXAMPLE 19

N-(2-cyclopropyl-3-methylimidazo[1,2-a]pyridin-6-yl)-3-[6-(trifluoromethyl)-3-pyridyl]propanamide Conducting the operations similar to those of Example 1 using 2-cyclopropyl-3-methyl-6-nitroimidazo[1,2-a]pyridine and 3-[6-(trifluoromethyl)-3-pyridyl]propionic acid, the title compound was obtained as white solid.

1H-NMR (400 MHz, CDCl3, δppm): 0.93-0.98 (4H, m), 1.94-2.00 (1H, m), 2.47 (3H, s), 2.75 (2H, t, J=7.2 Hz), 3.15 (2H, t, J=7.2 Hz), 6.68 (1H, dd, J=9.6, 2.0 Hz), 7.21 (1H, d, J=9.6 Hz), 7.57 (1H, d, J=8.0 Hz), 7.72 (1H, dd, J=8.0, 1.6 Hz), 8.37 (1H, brs), 8.57 (1H, s), 8.79 (1H, s)

EXAMPLE 20

N-(2-cyclopropyl-3-methylimidazo[1,2-a]pyridin-6-yl)-4-[5-(difluoromethoxy)-2-pyridyl] benzamide Conducting the operations similar to those of Example 1 using 2-cyclopropyl-3-methyl-6-nitroimidazo[1,2-a]pyridine and 4-[5-(difluoromethoxy)-2-pyridyl]benzenecarboxylic acid, the title compound was obtained as white solid.

1H-NMR (400 MHz, DMSO-d6, δppm): 0.87-0.91 (4H, m), 2.05-2.08 (1H, m), 2.50 (3H, s), 7.39 (1H, d, J=73.0 Hz), 7.39-7.44 (2H, m), 7.80 (1H, dd, J=8.4, 2.6 Hz), 8.10 (2H, d, J=8.1 Hz), 8.17 (1H, d, J=8.0 Hz), 8.23 (2H, d, J=8.4 Hz), 8.61 (1H, d, J=2.9 Hz), 8.89 (1H, s), 10.41 (1H, s)

EXAMPLE 21

5-Chloro-N-(2-cyclopropyl-3-methylimidazo[1,2-a]pyridin-6-yl)-2,3'-dipyridine-6'-carboxamide Conducting the operations similar to those of Example 1 using 2-cyclopropyl-3-methyl-6-nitroimidazo[1,2-a]pyridine and 5-chloro-2,3'-dipyridine-6'-carboxylic acid, the title compound was obtained as white solid.

1H-NMR (400 MHz, DMSO-d6, δppm): 0.87-0.91 (4H, m), 2.03-2.10 (1H, m), 2.50 (3H, s), 7.42 (1H, d, J=9.9 Hz), 7.64 (1H, d, J=9.5 Hz), 8.12-8.16 (1H, m), 8.23-8.28 (2H, m), 8.69-8.72 (2H, m), 8.81 (1H, dd, J=2.5, 1.8 Hz), 9.00 (1H, s), 9.39 (1H, d, J=1.1 Hz), 10.90 (1H, s)

EXAMPLE 22

N-(2-cyclopropyl-3-methylimidazo[1,2-a]pyridin-6-yl)-1-(4-fluorophenyl)-4-piperidinecarboxamide Conducting the operations similar to those of Example 1 using 2-cyclopropyl-3-methyl-6-nitroimidazo[1,2-a]pyridine and 1-(4-fluorophenyl)-4-piperidinecarboxylic, the title compound was obtained as white solid.

1H-NMR (300 MHz, DMSO-d6, δppm): 0.75-0.95 (4H, m) 1.65-2.00 (4H, m), 2.00-2.15 (1H, m), 2.45-2.60 (2H, m), 2.60-2.80 (2H, m), 3.60-3.85 (2H, m), 6.90-7.15 (5H, m), 7.35-7.45 (1H, m), 8.82 (1H, s), 10.01 (1H, s)

EXAMPLE 23

N-(2-cyclopropyl-3-methylimidazo[1,2-a]pyridin-6-yl)-4-[6-(difluoromethyl)-3-pyridyl]benzamide Conducting the operations similar to those of Example 1 using 2-cyclopropyl-3-methyl-6-nitroimidazo[1,2-a]pyridine and 4-[6-(difluoromethyl)-3-pyridyl]benzenecarboxylic acid, the title compound was obtained as white solid.

1H-NMR (400 MHz, DMSO-d6, δppm): 0.87 (4H, m), 2.04 (1H, m), 2.47 (3H, s), 7.04 (1H, t, J=54.9 Hz), 7.41 (2H, m), 7.83 (1H, d, J=8.1 Hz), 7.94 (2H, d, J=8.3 Hz), 8.14 (2H, d, J=8.3 Hz), 8.38 (1H, d, J=8.1 Hz), 8.91 (1H, s), 9.10 (1H, s), 10.44 (1H, s)

EXAMPLE 24

N-(2-cyclopropyl-3-methylimidazo[1,2-a]pyridin-6-yl)-3-fluoro-4'-(trifluoromethyl)[1,1'-biphenyl]-4-carboxamide Conducting the operations similar to those of Example 1 using 2-cyclopropyl-3-methyl-6-nitroimidazo[1,2-a]pyridine and 3-fluoro-4'-(trifluoromethyl)[1,1'-biphenyl]-4-carboxylic acid, the title compound was obtained as white solid.

1H-NMR (300 MHz, DMSO-d6, δppm): 0.85-0.95 (4H, m)2.00-2.15 (1H, m), 2.48 (3H, s), 7.25 (1H, d, J=9.6 Hz), 7.43 (1H, d, J=9.6 Hz), 7.76 (1H, d, J=7.8 Hz), 7.83 (1H, d, J=7.8 Hz), 7.86 (1H, s), 7.88 (2H, d, J=8.4 Hz), 8.03 (2H, d, J=8.4 Hz), 8.91 (1H, s), 10.58 (1H, s)

EXAMPLE 25

N-(2-cyclopropyl-3-methylimidazo[1,2-a]pyridin-6-yl)-4'-(methylsulfonyl)[1,1'-biphenyl]-4-carboxamide Conducting the operations similar to those of Example 1 using 2-cyclopropyl-3-methyl-6-nitroimidazo[1,2-a]pyridine and 4'-(methylsulfonyl)[1,1'-biphenyl]-4-carboxylic acid, the title compound was obtained as white solid.

1H-NMR (400 MHz, CDCl3, δppm): 0.95-1.06 (4H, m), 1.95-2.03 (1H, m), 2.52 (3H, s), 3.10 (3H, s), 6.99 (1H, dd, J=9.6, 2.0 Hz), 7.45 (1H, d, J=9.6 Hz), 7.68 (2H, d, J=8.0 Hz), 7.78 (2H, d, J=8.0 Hz), 8.02 (4H, dd, J=8.4, 2.0 Hz), 8.18 (1H, s), 8.96 (1H, s)

EXAMPLE 26

4-(6-Chloro-3-pyridazinyl)-N-(2-cyclopropyl-3-methylimidazo-[1,2-a]pyridin-6-yl)benzamide Operations similar to Example 1 were conducted using 2-cyclopropyl-3-methyl-6-nitroimidazo[1,2-a]pyridine and 4-(6-chloro-3-pyridazinyl)benzenecarboxylic acid, to provide the title compound as white solid.

1H-NMR (400 MHz, CDCl3, δppm): 0.98 (4H, m), 1.97 (1H, m), 2.50 (3H, s), 7.22 (1H, d, J=9.5 Hz), 7.39 (1H, d, J=9.5 Hz), 7.68 (1H, dJ=9.0 Hz), 7.95 (1H, d, J=9.0 Hz), 8.12 (4H, m), 8.96 (1H, s)

EXAMPLE 27

N-(2-cyclopropyl-3-methylimidazo[1,2-a]pyridin-6-yl)-2,3'-dipyridine-6'-carboxamide Operations similar to Example 1 were conducted using 2-cyclopropyl-3-methyl-6-nitroimidazo[1,2-a]pyridine and 2,3'-dipyridine-6'-carboxylic acid, to provide the title compound as white solid.

1H-NMR (400 MHz, DMSO-d6, δppm): 0.85-0.93 (4H, m), 2.03-2.10 (1H, m), 2.48 (3H, s), 7.41 (1H, d, J=9.5 Hz), 7.48 (1H, dd, J=7.7, 4.8 Hz), 7.63 (1H, dd, J=9.5, 1.8 Hz), 8.00 (1H, dd, J=8.0, 1.8 Hz), 8.18 (1H, d, J=7.7 Hz), 8.26 (1H, d, J=8.1 Hz), 8.70 (1H, dd, J=8.4, 2.2 Hz), 8.76 (1H, ddd, J=4.7, 0.7, 0.7 Hz), 9.00 (1H, s), 9.40 (1H, d, J=2.2 Hz), 10.88 (1H, s)

EXAMPLE 28

N-(2-cyclopropyl-3-methylimidazo[1,2-a]pyridin-6-yl)-4-(1H-pyrro-1-lyl)benzamide Operations similar to Example 1 were conducted using 2-cyclopropyl-3-methyl-6-nitroimidazo[1,2-a]pyridine and 4-(1H-pyrro-1-lyl)benzenecarboxylic acid, to provide the title compound as white solid.

1H-NMR (400 MHz, DMSO-d6, δppm): 0.98 (2H, m), 1.13 (2H, m), 2.26 (1H, m), 2.57 (3H, s), 6.34 (2H, s), 7.55 (2H, s), 7.83 (2H, dJ=8.7 Hz), 7.84 (1H, m), 8.03 (1H, m), 8.12 (2H, d, J=8.7 Hz), 9.24 (1H, s), 10.74 (1H, s)

EXAMPLE 29

N-(2-cyclopropyl-3-methylimidazo[1,2-a]pyridin-6-yl)-4-(5-methoxy-2-pyridyl)benzamide Operations similar to Example 1 were conducted using 2-cyclopropyl-3-methyl-6-nitroimidazo[1,2-a]pyridine and 4-(5-methoxy-2-pyridyl)benzenecarboxylic acid, to provide the title compound as white solid.

1H-NMR (400 MHz, DMSO-d6, δppm): 0.87-0.91 (4H, m), 2.05-2.09 (1H, m), 2.50 (3H, s), 3.90 (3H, s), 7.42 (2H, s), 7.53 (1H, dd, J=8.8, 2.9 Hz), 8.06 (2H, d, J=8.8 Hz), 8.09 (2H, d, J=8.4 Hz), 8.21 (2H, d, J=9.4 Hz), 8.44 (1H, d, J=3.9 Hz), 8.91 (1H, s), 10.38 (1H, s)

EXAMPLE 30

N-(2-cyclopropyl-3-methylimidazo[1,2-a]pyridin-6-yl)-4-(5-methyl-2-pyridyl)benzamide Operations similar to Example 1 were conducted using 2-cyclopropyl-3-methyl-6-nitroimidazo[1,2-a]pyridine and 4-(5-methyl-2-pyridyl)benzenecarboxylic acid, to provide the title compound as white solid.

1H-NMR (400 MHz, DMSO-d6, δppm): 0.88 (4H, m), 2.06 (1H, m), 2.37 (3H, s), 2.48 (3H, s), 7.42 (2H, m), 7.78 (1H, d, J=8.2 Hz), 8.00 (1H, d, J=8.2 Hz), 8.10 (2H, d, J=8.4 Hz), 8.24 (2H, d, J=8.4 Hz), 8.56 (1H, s), 8.90 (1H, s), 10.39 (1H, s)

EXAMPLE 31

N-[2-(1-hydroxy-1-methylethyl)imidazo[1,2-a]pyridin-6-yl]-4'-(trifluoromethyl)[1,1'-biphenyl]-4-carboxamide (1) Operations similar to Example 1 were conducted using ethyl 6-nitroimidazo[1,2-a]pyridine-2-carboxylate (600 mg) and 4'-(trifluoromethyl)[1,1'-biphenyl]-4-carboxylic acid (700 mg), to provide ethyl 6-({[4'-(trifluoromethyl)[1,1'-biphenyl]-4-yl]carbonyl}-amino)imidazo[1,2-a]pyridine-2-carboxylate (360 mg) as white solid.

(2) To a THF solution (15 ml) of the compound (140 mg) as obtained in above (1), a diethyl ether solution (1.0 ml) of 3M methylmagnesium bromide was added under cooling with ice and stirring, followed by 2 hours' stirring at the same temperature. Then saturated aqueous ammonium chloride solution was added and the reaction mixture was extracted with ethyl acetate. The extract was dried over anhydrous sodium sulfate. The organic layer was concentrated under reduced pressure, and the residue was purified on silica gel column chromatography (chloroform/methanol=90/1-50/1) to provide the title compound (30 mg) as white solid.

1H-NMR (400 MHz, DMSO-d6, δppm): 1.48 (6H, s), 4.98 (1H, s), 7.38 (1H, dd, J=9.6, 2.0 Hz), 7.47 (1H, d, J=9.6 Hz), 7.81 (1H, s), 7.84 (2H, d, J=8.0 Hz), 7.92 (2H, d, J=8.0 Hz), 7.98 (2H, d, J=8.0 Hz), 8.10 (2H, d, J=8.0 Hz), 9.24 (1H, s), 10.38 (1H, brs)

EXAMPLE 32

N-[2-(1-hydroxy-1-methylethyl)-3-methylimidazo[1,2-a]-pyridin-6-yl]-4-[5-(trifluoromethyl)-2-pyridyl]benzamide Operations similar to those of Example 31 were conducted using methyl 3-methyl-6-nitroimidazo[1,2-a]pyridine-2-carboxylate and 4-[5-(trifluoromethyl)-2-pyridyl]benzenecarboxylic acid, to provide the title compound as white solid.

1H-NMR (400 MHz, DMSO-d6, δppm): 1.52 (6H, s), 2.59 (3H, s), 4.99 (1H, s), 7.41 (1H, dd, J=9.6, 2.0 Hz), 7.50 (1H, d, J=9.6 Hz), 8.14 (2H, d, J=8.0 Hz), 8.30-8.37 (4H, m), 8.91 (1H, s), 9.08 (1H, s), 10.46 (1H, s)

EXAMPLE 33

4-(5-Chloro-2-pyridyl)-N-[2-(1-hydroxy-1-methylethyl)-3-methylimidazo[1,2-a]pyridin-6-yl]benzamide Operations similar to those of Example 31 were conducted using methyl 3-methyl-6-nitroimidazo[1,2-a]pyridine-2-carboxylate and -(5-chloro-2-pyridyl)benzenecarboxylic acid, to provide the title compound as white solid.

1H-NMR (400 MHz, DMSO-d6, δppm): 1.52 (6H, s), 2.59 (3H, s), 4.99 (1H, s), 7.42 (1H, dd, J=9.5, 1.8 Hz), 7.50 (1H, d, J=9.5 Hz), 8.05-8.16 (4H, m), 8.25 (2H, d, J=8.4 Hz), 8.75 (1H, d, J=2.2 Hz), 8.91 (1H, s), 10.43 (1H, s)

EXAMPLE 34

N-[2-(hydroxymethyl)-3-methylimidazo[1,2-a]pyridin-6-yl]-4'-(trifluoromethyl)[1,1'-biphenyl]-4-carboxamide (1) Operations similar to those of Example 1 were conducted using methyl 3-methyl-6-nitroimidazo[1,2-a]pyridine-2-carboxylate and 4'-(trifluoromethyl)[1,1'-biphenyl]-4-carboxylic acid, to provide methyl 3-methyl-6-({[4'-(trifluoromethyl)[1,1'-biphenyl]-4-yl]-carbonyl}amino)-imidazo[1,2-a]pyridine-2-carboxylate as white solid.

(2) The compound (698 mg) as obtained in (1) was dissolved in THF solution (140 ml), to which lithiumaluminum hydride (58.4 mg) was added under cooling with ice, followed by 30 minutes' stirring. Further lithiumaluminum hydride (58.4 mg) was added and stirred for 15 minutes, followed by addition of 4N aqueous sodium hydroxide solution (500 µl), addition of water, and extraction with ethyl acetate. The extract was dried over anhydrous sodium sulfate. The organic layer was concentrated under reduced pressure, and the residue was purified on silica gel column chromatography (chloroform/methanol=90/1-50/1) to provide the title compound (484 mg) as white solid.

1H-NMR (400 MHz, DMSO-d6, δppm): 2.47 (3H, s), 4.57 (2H, d, J=5.9 Hz), 4.97 (1H, t, J=5.9 Hz), 7.45 (1H, dd, J=9.5, 1.5 Hz), 7.51 (1H, d, J=9.5 Hz), 7.85 (2H, d, J=8.4 Hz), 7.93 (2H, d, J=8.1 Hz), 7.99 (2H, d, J=8.1 Hz), 8.12 (2H, d, J=8.1 Hz), 8.96 (1H, s), 10.44 (1H, s)

EXAMPLE 35

N-(2,3-dimethylimidazo[1,2-a]pyridin-6-yl)-N-methyl-4'-(trifluoromethyl)[1,1'-biphenyl]-4-carboxamide The compound (68 mg) as obtained in Example 3 was dissolved in DMF solution (10 ml), and to which sodium hydride (60% oil-like, 10 mg) was added under cooling with ice, followed by 30 minutes' stirring, addition of methyl iodide (20 µl) and further an hour's stirring at the same temperature. Then the reaction liquid was poured into water. The reaction mixture was extracted with ethyl acetate, and the extract was washed with water and saturated brine, and dried over anhydrous sodium sulfate. The organic layer was concentrated under reduced pressure, and the residue was purified on silica gel column chromatography (chloroform/methanol=90/1) to provide the title compound (12 mg) as white solid.

1H-NMR (400 MHz, CDCl3, δppm): 2.23 (3H, s), 2.37 (3H, s), 3.52 (3H, s), 7.02 (1H, dd, J=9.6, 2.0 Hz), 7.40-7.50 (6H, m), 7.57 (2H, d, J=8.0 Hz), 7.63 (2H, d, J=8.0 Hz)

EXAMPLE 36

N-[2-cyclopropyl-3-(hydroxymethyl)imidazo[1,2-a]pyridin-6-yl]-4'-(trifluoromethyl)[1,1'-biphenyl]-4-carboxamide 1) Operations similar to those of Example 1 were conducted using 2-cyclopropyl-6-nitroimidazo[1,2-a]pyridine hydrobromide and 4'-(trifluoromethyl)[1,1'-biphenyl]-4-carboxylic acid, to provide N-(2-cyclopropylimidazo[1,2-a]pyridin-6-yl)-4'-(trifluoromethyl)[1,1'-biphenyl]-4-carboxamide as white solid.

1H-NMR (400 MHz, CDCl3, δppm): 0.92-1.02 (4H, m), 2.00-2.08 (1H, m), 6.91 (1H, dd, J=9.6, 2.0 Hz), 7.37 (1H, s), 7.44 (1H, d, J=9.6 Hz), 7.68-7.73 (6H, m), 7.90 (1H, brs), 7.96 (2H, d, J=8.0 Hz), 9.18 (1H, s)

2) To a THF suspension (1 ml) of the compound (84 mg) as obtained in above 1), sodium acetate (132 mg), acetic acid (60 μl) and formaline (500 μl) were added and stirred for 9 hours at room temperature. Water was added to the reaction liquid which then was extracted with ethyl acetate. The organic layer was washed with saturated aqueous sodium hydrogencarbonate solution and saturated brine, and dried over anhydrous sodium sulfate. The organic layer was concentrated under reduced pressure and crystallized from ethyl acetate, to provide the title compound (32 mg) as white solid.

1H-NMR (400 MHz, DMSO-d6, δppm): 0.89-0.92 (4H, m), 2.10-2.11 (1H, m), 4.84 (2H, d, J=5.1 Hz), 5.15 (1H, t, J=5.1 Hz), 7.41-7.48 (2H, m), 7.85 (2H, d, J=8.8 Hz), 7.92 (2H, d, J=8.4 Hz), 7.99 (2H, d, J=8.4 Hz), 8.11 (2H, d, J=8.4 Hz), 9.13 (1H, s), 10.42 (1H, s)

EXAMPLE 37

4-(5-Chloro-2-pyridyl)-N-[2-cyclopropyl-3-(hydroxymethyl)imidazo[1,2-a]pyridin-6-yl]benzamide Operations similar to those of Example 1 were conducted using 2-cyclopropyl-6-nitroimidazo[1,2-a]pyridine and 4-(5-chloro-2-pyridyl)benzenecarboxylic acid, to provide 4-(5-chloro-2-pyridyl)-N-(2-cyclopropylimidazo[1,2-a]pyridine-6-yl)benzamide as white solid. Further treating the resulting compound in the manner similar to Example 36, the title compound was obtained as white solid.

1H-NMR (400 MHz, DMSO-d6, δppm): 0.89-0.92 (4H, m), 2.09-2.13 (1H, m), 4.84 (2H, d, J=4.8 Hz) 5.15 (1H, t, J=4.8 Hz), 7.41-7.49 (2H, m), 8.05-8.15 (4H, m), 8.25 (2H, d, J=8.4 Hz), 8.75 (1H, dd, J=2.6, 0.7 Hz), 9.12 (1H, s), 10.43 (1H, s)

EXAMPLE 38

N-{3-methyl-2-[(2-oxopyrrolidin-1-yl)methyl]imidazo[1,2-a]-pyridin-6-yl}-4'-(trifluoromethyl)[1,1'-biphenyl]-4-carboxamide (1) Phosphorus oxychloride (112 μl) was added to DMF solution (5 ml) and stirred for 3 hours at 80° C. Allowing the reaction liquid to cool off, N-[2-(hydroxymethyl)-3-methylimidazo-[1,2-a]pyridin-6-yl]-4'-(trifluoromethyl)[1,1'-biphenyl]-4-carboxamide (170 mg) which was obtained in Example 34 was added at room temperature, followed by an hour's stirring at 80° C. An aqueous sodium hydrogencarbonate solution was added to the reaction liquid which then was extracted with ethyl acetate. The organic layer was washed with water and saturated brine, and dried over anhydrous sodium sulfate. Concentrating the organic layer under reduced pressure, N-[2-(chloromethyl)-3-methylimidazo[1,2-a]pyridin-6-yl]-4'-(trifluoromethyl)[1,1'-biphenyl]-4-carboxamide (119 mg) was obtained.

(2) To a DMF solution (2.0 ml) of the compound (24 mg) as obtained in above (1) and 2-pyrrolidone (77 μl), sodium hydride (60% oil-like, 40 mg) was added and stirred for 4 hours at room temperature. Water was added to the reaction liquid which then was extracted with ethyl acetate. The organic layer was washed with water and saturated brine, dried over anhydrous sodium sulfate and concentrated under reduced pressure. The residue was purified on silica gel chromatography (chloroform/methanol=90/1-30/1) to provide the title compound (6 mg) as white solid.

1H-NMR (400 MHz, CDCl3, δppm): 1.93-2.02 (2H, m), 2.38 (2H, t, J=8.0 Hz), 2.49 (3H, s), 3.46 (2H, t, J=7.0 Hz), 4.60 (2H, s), 7.03 (1H, dd, J=9.5, 1.8 Hz), 7.46 (1H, d, J=9.2 Hz), 7.70-7.73 (6H, m), 8.02 (2H, d, J=8.1 Hz), 8.30 (1H, brs), 8.96 (1H, s)

EXAMPLE 39

N-(2-{[acetyl(methyl)amino]methyl}-3-methylimidazo[1,2-a]-pyridin-6-yl)-4'-(trifluoromethyl)[1,1'-biphenyl]-4-carboxamide To a THF-DMF mixed solution (3 ml; 1:1 by weight) of Example 34 compound (39 mg), triethylamine (193 μl) and methanesulfonyl chloride (53 mg) were added under cooling with ice, followed by 3 hours' stirring at the same temperature. Then a methanol solution (5 ml) of 2M methylamine was added and stirred for an additional hour. Concentrating the reaction mixture under reduced pressure, the residue was dissolved in THF-chloroform mixed solution (5 ml), and to the solution triethylamine (400 μl) and acetyl chloride (50 mg) were added, followed by stirring for a day and night at room temperature. Water was added to the reaction liquid which then was extracted with chloroform, dried over anhydrous sodium sulfate, and concentrated under reduced pressure. The residue was purified on silica gel chromatography (chloroform/methanol=90/1-30/1), to provide the title compound (2 mg) as white solid.

1H-NMR (300 MHz, CDCl3, δppm): 1.98 (2H, s), 2.12 (1H, s), 2.35 (1H, s), 2.54 (2H, s), 2.95 (1H, s), 3.12 (2H, s), 4.64 (2/3H, s), 4.74 (4/3H, s), 7.00 (1H, m), 7.55 (1H, m), 7.75 (5H, m), 8.04 (3H, m), 8.99 (1H, m)

EXAMPLE 40

N-{2-[(dimethylamino)methyl]-3-methylimidazo[1,2-a]-pyridin-6-yl}-4'-(trifluoromethyl)[1,1'-biphenyl]-4-carboxamide trifluoroacetate To a THF-DMF mixed solution (5 ml; 1:1 by weight) of Example 34 compound (210 mg), triethylamine (1.0 ml) and methanesulfonyl chloride (290 mg) were added under cooling with ice, followed by 1 hour's stirring at the same temperature. Then a THF solution (5 ml) of 2M dimethylamine was added and stirred for an additional hour. Concentrating the reaction mixture under reduced pressure, water was added to the residue, followed by extraction with chloroform and drying over anhydrous sodium sulfate. After concentration under reduced pressure, the residue was purified on silica gel chromatography (chloroform/methanol=90/1-30/1) and then on reversed phase HPLC [acetonitrile/water (0.1% trifluoroacetic acid)=10/90-90/10], to provide the title compound (10 mg) as white solid.

1H-NMR (400 MHz, DMSO-d6, δppm): 2.56 (3H, s), 2.82 (6H, s), 4.86 (2H, s), 7.73 (2H, s), 7.88 (2H, d, J=8.2 Hz), 7.97 (2H, d, J=8.3 Hz), 8.01 (2H, d, J=8.2 Hz), 8.16 (2H, d, J=8.3 Hz), 9.13 (1H, s), 10.64 (1H, s)

EXAMPLE 41

N-{2-[acetyl(methyl)amino]-3-methylimidazo[1,2-a] pyridin-6-yl}-4'-(trifluoromethyl)[1,1'-biphenyl]-4-carboxamide (1) Operations similar to Example 1 were conducted using 2,2,2-trifluoro-N-methyl-N-(3-methyl-6-nitroimidazo[1,2-a]pyridin-2-yl)acetamide (580 mg) and 4'-(trifluoromethyl)

[1,1'-biphenyl]-4-carboxylic acid (510 mg), to provide N-{3-methyl-2-[methyl(2,2,2-trifluoroacetyl)amino]imidazo[1,2-a]pyridin-6-yl}-4'(trifluoromethyl)-[1,1'-biphenyl]-4-carboxamide (610 mg) as white solid.

(2) The compound (600 mg) as obtained in above (1) was added to a mixed solution of methanol (25 ml)-diisopropylethylamine (5 ml), and stirred for a day and night at 80° C. The reaction liquid was concentrated under reduced pressure, ethyl acetate was added to the concentrate, the organic layer was washed with saturated aqueous sodium hydrogencarbonate solution and saturated brine, and dried over anhydrous sodium sulfate. The solid precipitated after concentration under reduced pressure was washed with ethyl acetate to provide N-[3-methyl-2-(methylamino)imidazo[1,2-a]pyridin-6-yl]-4'-(trifluoromethyl)[1,1'-biphenyl]-4-carboxamide (132 mg) as white solid.

(3) The compound (20 mg) as obtained in above (2) was suspended in THF-acetonitrile mixed solution (3 ml; 1:1 by weight). To the suspension diisopropylethylamine (500 μl) and acetyl chloride (40 μl) were added and stirred for an hour at room temperature. After concentrating the reaction liquid under reduced pressure, the residue was purified on silica gel chromatography (chloroform/methanol=90/1-30/1) to provide the title compound (3 mg) as white solid.

1H-NMR (400 MHz, DMSO-d6, δppm): 1.90 (3H, s), 2.44 (3H, s), 3.30 (3H, s), 7.08 (1H, d, J=9.6 Hz), 7.55 (1H, d, J=9.6 Hz), 7.70-7.80 (6H, m), 7.97-8.05 (3H, m), 9.10 (1H, s)

EXAMPLE 42

4-(4-Chlorophenyl)-N-(2-cyclopropyl-3-methylimidazo[1,2-a]-pyridin-6-yl)-4-hydroxytetrahydro-1(2H)-pyridinecarboxamide (1) To a methanol solution (40 ml) of 2-cyclopropyl-3-methyl-6-nitroimidazo[1,2-a]pyridine (500 mg), 10% palladium-on-carbon (50 mg) was added. After substituting the atmosphere of the reaction system with hydrogen, the system was stirred for an hour at room temperature. Filtering the reaction liquid through Celite®, the filtrate was concentrated under reduced pressure. The resulting residue was dissolved in THF, and to the solution triethylamine (321 μl) and phenyl chloroformate (290 μl) were added under cooling with ice, followed by an hour's stirring. Water was added to the reaction liquid which was then extracted with ethyl acetate. The organic layer was washed with water and saturated brine and dried over anhydrous sodium sulfate. Concentrating the organic layer under reduced pressure, the resulting solid was washed with diethyl ether to provide phenyl N-(2-cyclopropyl-3-methyl-6-nitroimidazo[1,2-a]pyridin-6-yl)carbamate (480 mg).

1H-NMR (400 MHz, CDCl3, δppm): 0.92-1.00 (2H, m), 1.00-1.06 (2H, m), 1.92-2.00 (1H, m), 2.44 (3H, s), 6.81 (1H, d, J=9.6 Hz), 6.99 (1H, brs), 7.16-7.20 (2H, m), 7.24-7.27 (1H, m), 7.37-7.44 (3H, m), 8.50 (1H, brs)

(2) To a THF solution of the compound (50 mg) as obtained in above (1), 4-(4-chlorophenyl)-4-hydroxypiperidine (34 mg) and 1,8-diazabicyclo[5.4.0]unde-7-cene (24 μl) were added and stirred for an hour at 70° C. Water was added to the reaction liquid which was then extracted with ethyl acetate. The organic layer was washed with water and saturated brine and dried over anhydrous sodium sulfate. Concentrating the organic layer under reduced pressure, the residue was purified on silica gel column chromatography (chloroform/methanol=80/1) to provide the title compound (42 mg) as white solid.

1H-NMR (400 MHz, DMSO-d6, δppm): 0.82-0.90 (4H, m), 1.58-1.65 (2H, m), 1.82-1.93 (2H, m), 1.98-2.05 (1H, m), 2.40 (3H, s), 3.17-3.26 (2H, m), 4.00-4.08 (2H, m), 5.20 (1H, s), 7.18 (1H, dd, J=9.6, 1.6 Hz), 7.27 (1H, d, J=9.6 Hz), 7.35 (2H, d, J=8.0 Hz), 7.50 (2H, d, J=8.0 Hz), 8.42 (1H, s), 8.48 (1H, s)

Other than the foregoing Examples, the compounds as shown in Table 5 or Table 6 were synthesized according to the Examples. Their molecular weights were measured by electrospray ionizing (ESI) method.

TABLE 5

| No | Formula | [M + H]+ |
|---|---|---|
| 43 | | 376 |
| 44 | | 440 |

TABLE 5-continued

| No | Formula | [M + H]+ |
|----|---------|----------|
| 45 | | 422 |
| 46 | | 425 |
| 47 | | 396 |
| 48 | | 365 |
| 49 | | 438 |
| 50 | | 376 |

TABLE 5-continued

| No | Formula | [M + H]+ |
|---|---|---|
| 51 | | 375 |
| 52 | | 426 |
| 53 | | 412 |
| 54 | | 467 |
| 55 | | 439 |
| 56 | | 374 |

TABLE 5-continued

| No | Formula | [M + H]+ |
|----|---------|----------|

TABLE 6

| No | Formula | [M + H]+ |
|----|---------|----------|
| 57 | | 438 |
| 58 | | 406 |
| 59 | | 425 |
| 60 | | 389 |
| 61 | | 450 |

TABLE 6-continued

| No | Formula | [M + H]+ |
|---|---|---|
| 62 | | 503 |
| 63 | | 390 |
| 64 | | 426 |
| 65 | | 397 |
| 66 | | 412 |
| 67 | | 434 |

TABLE 6-continued
| No | Formula | [M + H]+ |
|---|---|---|
| 68 | 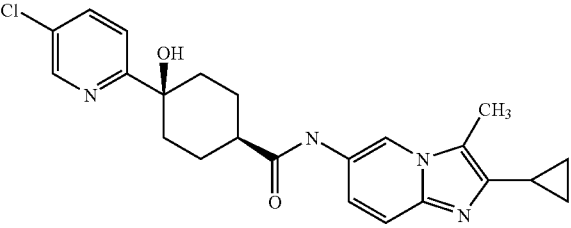 | 425 |
| 69 | 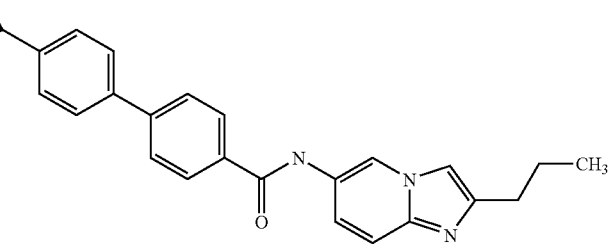 | 424 |
| 70 | 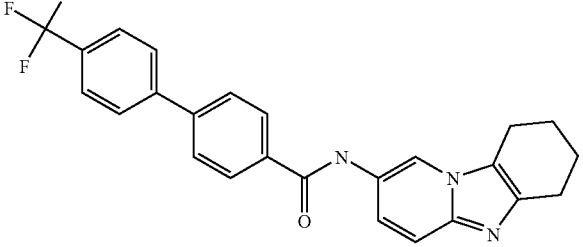 | 438 |
| 71 | 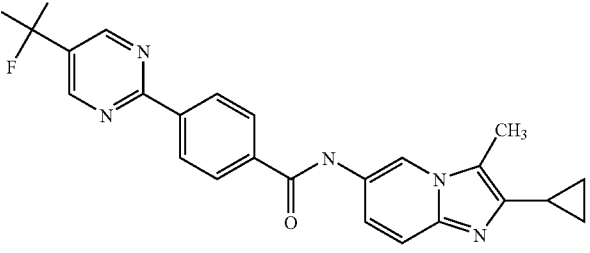 | 438 |
| 72 | 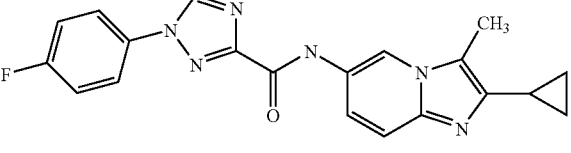 | 377 |
| 73 | 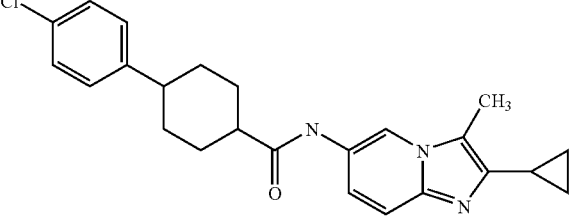 | 408 |

TABLE 6-continued

| No | Formula | [M + H]+ |
|---|---|---|
| 74 | 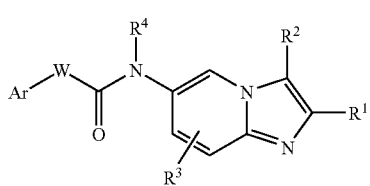 | 450 |

INDUSTRIAL APPLICABILITY

Those compounds of the present invention exhibit MCH-IR antagonism, and are useful as preventing or treating agents of metabolic disorders, such as obesity, diabetes, hormone disorder, hyperlipidemia, gout, fatty liver and the like; cardiovascular disorders such as stenocardia, acute or congestive heart failure, myocardial infarction coronary atherosclerosis, hypertension, renal diseases, electrolyte abnormality and the like; central nervous system or peripheral nervous system disorders such as bulimia, emotional disturbance, depression, anxiety, epilepsy, delirium, dementia, schizophrenia, attention-deficit hyperactivity disorder, memory impairment, sleep disorders, cognitive failure, dyskinesia, paresthesia, smell disorders, morphine tolerance, drug dependence, alcoholism and the like; reproductive disorders such as infertility, preterm labor, sexual dysfunction; digestive disorders; respiratory disorders; cancer or pigmentation.

The invention claimed is:

1. A compound of formula [I]

[I]

wherein:
each $R^1$ and $R^2$ are independently selected from the group consisting of:
(1) hydrogen
(2) halogen
(3) $C_{1-6}$ alkyl
(4) $C_{3-8}$ cycloalkyl-$C_{0-4}$ alkyl
(5) $C_{1-6}$ alkylamino
(6) di-$C_{1-6}$ alkylamino
(7) $C_{1-6}$ alkylcarbonylamino
(8) $C_{1-6}$ alkylcarbonyl-($C_{1-6}$ alkyl)amino, and
(9) 3 to 8-membered heterocycloalkyl-$C_{0-4}$ alkyl,
wherein the $C_{1-6}$ alkyl moiety may be substituted with $R^5$, the cycloalkyl or heterocycloalkyl moiety may be substituted with $R^6$, and $R^1$ and $R^2$ are not hydrogen at the same time, or $R^1$ and $R^2$ together form —$(CH_2)_m$—, m standing for an integer of 3-6, wherein 1 or 2 hydrogen atoms constituting methylene may be substituted with $R^6$;
$R^3$ is hydrogen, halogen, $C_{1-6}$ alkyl or $C_{1-6}$ alkyloxy;

$R^4$ is hydrogen or $C_{1-6}$ alkyl;
each $R^5$ is independently selected from the group consisting of halogen, cyano, hydroxyl, amino, optionally fluorine- or hydroxyl-substituted $C_{1-6}$ alkyl, mono-$C_{1-6}$ alkylamino, di-$C_{1-6}$ alkylamino, optionally fluorine-substituted $C_{1-6}$ alkyloxy, $C_{1-6}$ alkyloxy-$C_{1-6}$ alkyl, $C_{1-6}$ alkyloxycarbonyl, $C_{1-6}$ alkyloxy-carbonylamino, $C_{1-6}$ alkyloxycarbonyl-($C_{1-6}$ alkyl)amino, $C_{1-6}$ alkylcarbonyl, $C_{1-6}$ alkylcarbonyloxy, $C_{1-6}$ alkylcarbonylamino, $C_{1-6}$ alkylcarbonyl-($C_{1-6}$ alkyl)amino, carbamoyl, mono-$C_{1-6}$ alkylcarbamoyl, di-$C_{1-6}$ alkylcarbamoyl, carbamoylamino, mono-$C_{1-6}$ alkylcarbamoylamino, di-$C_{1-6}$ alkylcarbamoylamino, mono-$C_{1-6}$ alkylcarbamoyl-($C_{1-6}$ alkyl)amino, di-$C_{1-6}$ alkylcarbamoyl-($C_{1-6}$ alkyl)amino, carbamoyloxy, mono-$C_{1-6}$ alkylcarbamoyloxy, di-$C_{1-6}$ alkylcarbamoyloxy, $C_{1-6}$ alkylsulfonyl, $C_{1-6}$ alkylsulfonylamino, $C_{1-6}$ alkylsulfonyl-($C_{1-6}$ alkyl)amino, sulfamoyl, mono-$C_{1-6}$ alkylsulfamoyl, di-$C_{1-6}$ alkylsulfamoyl, sulfamoylamino, mono-$C_{1-6}$ alkylsulfamoylamino, di-$C_{1-6}$ alkylsulfamoylamino, mono-$C_{1-6}$ alkylsulfamoyl-($C_{1-6}$ alkyl)amino, di-$C_{1-6}$ alkylsulfamoyl-($C_{1-6}$ alkyl)amino and pyridone;
$R^6$ is $R^5$ or oxo;
W is:
(1) 1,4-piperidin-di-yl,
(2) mono- or bi-cyclic, 3 to 8-membered aromatic heterocyclic group,
(3) mono- or bi-cyclic, 3 to 8 membered aromatic or aliphatic carbocyclic group,
(4) $C_{2-4}$ alkylene in which the carbon in the main chain may be substituted with oxygen, or
(5) $C_{2-4}$ alkenylene in which the carbon in the main chain may be substituted with oxygen,
wherein those substituents in above (2) through (5) may be optionally substituted with $R^5$; and
Ar is an $R^7$-substituted aromatic carbocyclic group or aromatic heterocyclic group, said aromatic carbocyclic group or aromatic heterocyclic group selected from the group consisting of:
(1) phenyl,
(2) naphthyl,
(3) pyridinyl,
(4) pyrimidinyl,
(5) pyridazinyl,
(6) pyrazyl,
(7) pyrazole,
(8) pyrrolyl,
(9) imidazolyl,
(10) triazolyl,
(11) oxazolyl,

(12) isoxazolyl,
(13) oxadiazolyl,
(14) thiazolyl,
(15) isothiazolyl,
(16) thiadiazolyl, and
(17) tetrazolyl;
wherein $R^7$ is selected from $R^5$;
or a pharmaceutically acceptable salt thereof.

2. The compound according to claim 1 of formula [I-1]

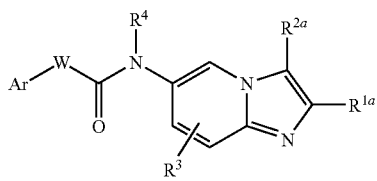

[I-1]

wherein:
$R^{1a}$ and $R^{2a}$ are each independently selected from the group consisting of:
(1) hydrogen,
(2) halogen,
(3) $C_{1-6}$ alkyl,
(4) $C_{3-8}$ cycloalkyl-$C_{0-4}$ alkyl,
(5) $C_{1-6}$ alkylamino,
(6) di-$C_{1-6}$ alkylamino,
(7) $C_{1-6}$ alkylcarbonylamino,
(8) $C_{1-6}$ alkylcarbonyl-($C_{1-6}$ alkyl)amino, and
(9) 3 to 8-membered heterocycloalkyl,
wherein the $C_{1-6}$ alkyl moiety may be substituted with $R^{5a}$, the cycloalkyl or heterocycloalkyl moiety may be substituted with $R^6$, and $R^{1a}$ and $R^{2a}$ are not hydrogen at the same time, or
$R^{1a}$ and $R^{2a}$ together form —(CH$_2$)m-, wherein m is an integer from 3 to 6, and wherein 1 or 2 hydrogen atoms constituting methylene may be substituted with $R^6$;
each $R^{5a}$ is independently selected from the group consisting of halogen, cyano, hydroxyl, optionally fluorine- or hydroxyl-substituted $C_{1-6}$ alkyl, optionally fluorine-substituted $C_{1-6}$ alkyloxy, $C_{1-6}$ alkyloxy-$C_{1-6}$ alkyl, $C_{1-6}$ alkyloxycarbonyl, $C_{1-6}$ alkyloxy-carbonylamino, $C_{1-6}$ alkyloxycarbonyl-($C_{1-6}$ alkyl)amino, $C_{1-6}$ alkylcarbonyl, $C_{1-6}$ alkylcarbonyloxy, $C_{1-6}$ alkylcarbonylamino, $C_{1-6}$ alkylcarbonyl-($C_{1-6}$ alkyl)amino, carbamoyl, mono-$C_{1-6}$ alkylcarbamoyl, di-$C_{1-6}$ alkylcarbamoyl, carbamoylamino, mono-$C_{1-6}$ alkylcarbamoylamino, di-$C_{1-6}$ alkylcarbamoylamino, mono-$C_{1-6}$ alkylcarbamoyl-($C_{1-6}$ alkyl)amino, di-$C_{1-6}$ alkylcarbamoyl-($C_{1-6}$ alkyl)amino, carbamoyloxy, mono-$C_{1-6}$ alkylcarbamoyloxy, di-$C_{1-6}$ alkylcarbamoyloxy, $C_{1-6}$ alkylsulfonyl, $C_{1-6}$ alkylsulfonylamino, $C_{1-6}$ alkylsulfonyl-($C_{1-6}$ alkyl) amino, sulfamoyl, mono-$C_{1-6}$ alkylsulfamoyl, di-$C_{1-6}$ alkylsulfamoyl, sulfamoylamino, mono-$C_{1-6}$ alkylsulfamoylamino, di-$C_{1-6}$ alkylsulfamoylamino, mono-$C_{1-6}$ alkylsulfamoyl-($C_{1-6}$ alkyl)amino, di-$C_{1-6}$ alkylsulfamoyl-($C_{1-6}$ alkyl)amino and pyridine, and
$R^3$, $R^4$, $R^6$, W and Ar are as defined in claim 1
or a pharmaceutically acceptable salt thereof.

3. The compound according to claim 1, wherein $R^1$ is $C_{1-6}$ alkyl, $C_{1-6}$ cycloalkyl, $C_{1-6}$ alkylamino, di-$C_{1-6}$ alkylamino or $C_{1-6}$ alkylcarbonyl-($C_{1-6}$ alkyl)amino, or a pharmaceutically acceptable salt thereof.

4. A compound according to claim 1, wherein $R^2$ is hydrogen, $C_{1-6}$ alkyl, $C_{1-6}$ cycloalkyl, $C_{1-6}$ alkylamino, di-$C_{1-6}$ alkylamino or $C_{1-6}$ alkylcarbonyl-($C_{1-6}$ alkyl)amino, or a pharmaceutically acceptable salt thereof.

5. A compound according to claim 2, wherein $R^{1a}$ is $C_{1-6}$ alkyl, $C_{1-6}$ cycloalkyl, $C_{1-6}$ alkylamino, di-$C_{1-6}$ alkylamino or $C_{1-6}$ alkylcarbonyl-($C_{1-6}$ alkyl)-amino, or a pharmaceutically acceptable salt thereof.

6. A compound according to claim 2, wherein $R^{2a}$ is hydrogen, $C_{1-6}$ alkyl, $C_{1-6}$ cycloalkyl, $C_{1-6}$ alkylamino, di-$C_{1-6}$ alkylamino or $C_{1-6}$ alkylcarbonyl-($C_{1-6}$ alkyl)-amino, or a pharmaceutically acceptable salt thereof.

7. A compound according to claim 1, wherein the 3 to 8-membered heterocycloalkyl moiety is selected from the group consisting of tetrahydrofuranyl, tetrahydropyranyl, pyrrolidinyl and piperidinyl.

8. A compound according to claim 1, wherein $R^3$ is hydrogen, methyl or methoxy, or a pharmaceutically acceptable salt thereof.

9. A compound according to claim 1, wherein $R^4$ is hydrogen or methyl, or a pharmaceutically acceptable salt thereof.

10. A compound according to claim 1, wherein W is selected from the group consisting of 1,2-dimethylene, 1,4-phenylene, 2-fluoro-1,4-phenylene, pyridin-2,5-di-yl, pyrimidin-2,5-di-yl, pyrazin-2,5-di-yl, 1,4-piperidin-di-yl, 1,2,4-triazol-1,3-di-yl, 1,4-cyclohexylene and oxymethylene, or a pharmaceutically acceptable salt thereof.

11. A compound according to claim 1, in which Ar is selected from the group consisting of pyrrol-1-yl, phenyl, 2-fluorophenyl, 3-fluorophenyl, 4-fluoropheny,4-chlorophenyl, 3,4-difluorophenyl, 2,4-difluorophenyl, 2-trifluoromethylphenyl, 3-trifluoromethylphenyl, 4-trifluoromethylphenyl, 4-methoxyphenyl, 4-methanesulfonylphenyl, pyridin-2-yl, 3-methylpyridin-6-yl, 2-fluoropyridin-5-yl, 3-fluoropyridin-6-yl, 3-chloropyridin-6-yl, 2-difluoromethylpyridin-5-yl, 3-difluoromethylpyridin-6-yl, 2-methoxypyridin-5-yl, 2-methoxypyridin -6-yl, 3-methoxypyridin-6-yl, 2-difluoromethoxypyridin-5-yl, 3-difluoromethoxypyridin-6-yl, 3-trifluoromethylpyridin-6-yl, 2-trifluoromethylpyridin-5-yl, 2-pyrimidinyl, 2-pyrazinyl and 3-pyridazinyl, or a pharmaceutically acceptable salt thereof.

12. A compound according to claim 1, which is N-(2,3-dimethylimidazo [1,2-a]-pyridin-6-yl)-4'-(trifluoromethyl) [1,1'-biphenyl]-4-carboxamide, or a pharmaceutically acceptable salt thereof.

13. A compound according to claim 1, which is N-(2-cyclopropyl-3-methylimidazo[1,2-a]-pyridin-6-yl)-4-(2-pyridyl)benzamide, or a pharmaceutically acceptable salt thereof.

14. A compound according to claim 1, which is N-(2-cyclopropyl-3-methylimidazo[1,2-a]pyridin-6-yl)-4-(1H-pyrro-1-lyl)benzamide, or a pharmaceutically acceptable salt thereof.

15. The method of inhibiting binding of melanin concentrating hormone to a melanin concentrating hormone receptor comprising administering to a patient a therapeutically effective amount of a melanin concentrating hormone receptor antagonist compound according to claim 1, or a pharmaceutically acceptable salt thereof.

16. A pharmaceutical composition comprising a compound according to claim 1, or a pharmaceutically acceptable salt thereof, and a pharmaceutically acceptable carrier.

17. The method of treating obesity in a patient in need thereof comprising administering to said patient a therapeutically effective amount of a compound according to claim 1, or a pharmaceutically acceptable salt thereof.

18. A method for producing a compound according to claim 1 of formula [I] which comprises the steps of:

(1) amidating a compound represented by a general formula [II], wherein Ar and W are as defined in claim 1, with a compound represented by a general formula [III] wherein $R^1$, $R^2$ and $R^3$ are as defined in claim 1; and (2) optionally condensing, where $R^4$ is not hydrogen, the compound as obtained in the above step with a compound represented by a general formula [IV], wherein $X_1$ is a leaving group and $R^4$ is defined in claim 1:

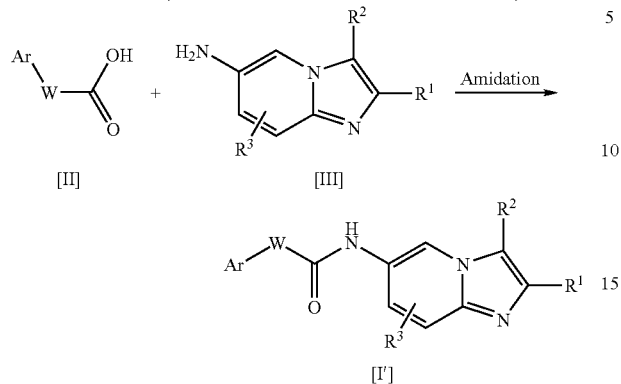

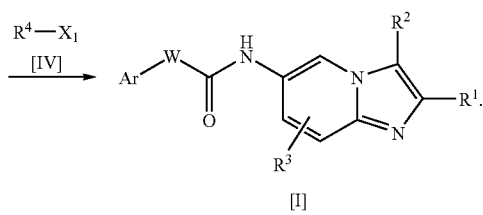

* * * * *